United States Patent
Meyer et al.

(10) Patent No.: US 10,449,324 B2
(45) Date of Patent: Oct. 22, 2019

(54) COMBINED RESPIRATORY MUSCLE TRAINING AND OSCILLATING POSITIVE EXPIRATORY PRESSURE DEVICE

(71) Applicant: Trudell Medical International, London (CA)

(72) Inventors: Adam Meyer, London (CA); Dan Engelbreth, London (CA)

(73) Assignee: Trudell Medical International, London, Ontario (CA)

( * ) Notice: Subject to any disclaimer, the term of this patent is extended or adjusted under 35 U.S.C. 154(b) by 587 days.

(21) Appl. No.: 15/223,564

(22) Filed: Jul. 29, 2016

(65) Prior Publication Data

US 2017/0028161 A1 Feb. 2, 2017

Related U.S. Application Data

(60) Provisional application No. 62/199,113, filed on Jul. 30, 2015.

(51) Int. Cl.
*A61M 16/20* (2006.01)
*A61M 16/00* (2006.01)
(Continued)

(52) U.S. Cl.
CPC ...... *A61M 16/208* (2013.01); *A61M 16/0006* (2014.02); *A61M 16/06* (2013.01); *A61M 16/0866* (2014.02); *A61M 16/20* (2013.01); *A63B 21/00069* (2013.01); *A63B 21/023* (2013.01); *A63B 23/18* (2013.01);
(Continued)

(58) Field of Classification Search
CPC .............. A63B 23/18; A63B 21/00069; A63B 21/00196; A63B 21/023; A61B 5/0086; A61B 5/087; A61B 5/0871; A61B 5/0876; A61B 5/09; A61M 16/00; A61M 16/0003; A61M 16/0006; A61M 16/049; A61M 16/06; A61M 16/0866; A61M 16/20; A61M 16/208; A61M 11/00; A61M 15/00; A61M 2205/056; A61M 2206/20; A61M 2230/40
See application file for complete search history.

(56) References Cited

U.S. PATENT DOCUMENTS 393,869 A 12/1888 Warren
938,808 A 11/1909 Yount
(Continued)

FOREIGN PATENT DOCUMENTS

EP 0 372 148 A1 6/1990
EP 0 678 306 A2 10/1995
(Continued)

OTHER PUBLICATIONS

Written Opinion of related application No. PCT/IB2016/054577 (8 pgs).
(Continued)

*Primary Examiner* — Joseph D. Boecker
(74) *Attorney, Agent, or Firm* — Brinks Gilson & Lione

(57) ABSTRACT

A respiratory treatment device for the combined administration of respiratory muscle training ("RMT") and oscillating positive expiratory pressure ("OPEP") therapy, and administration of RMT using pressure threshold resistors and flow resistors with respiratory treatment devices, such as OPEP devices.

21 Claims, 75 Drawing Sheets

(51) Int. Cl.
  *A61M 16/06* (2006.01)
  *A63B 23/18* (2006.01)
  *A61M 16/08* (2006.01)
  *A63B 21/02* (2006.01)
  *A63B 21/00* (2006.01)
  *A61M 11/00* (2006.01)
  *A61M 15/00* (2006.01)
  *A63B 71/06* (2006.01)

(52) U.S. Cl.
  CPC .............. *A61M 11/00* (2013.01); *A61M 15/00* (2013.01); *A63B 2071/0694* (2013.01)

(56) References Cited

U.S. PATENT DOCUMENTS

| | | | |
|---|---|---|---|
| 2,670,739 | A | 3/1954 | NcNeill |
| 2,918,917 | A | 12/1959 | Emerson |
| 3,710,780 | A | 1/1973 | Milch |
| 3,908,987 | A | 9/1975 | Boehringer |
| 4,037,595 | A * | 7/1977 | Elam ............... A61M 16/208 128/205.11 |
| 4,054,134 | A * | 10/1977 | Kritzer ............... A61M 16/00 128/204.18 |
| 4,062,358 | A | 12/1977 | Kritzer |
| 4,182,366 | A | 1/1980 | Boehringer |
| 4,198,969 | A | 4/1980 | Virag |
| 4,221,381 | A | 9/1980 | Ericson |
| 4,226,233 | A | 10/1980 | Kritzer |
| 4,231,375 | A | 11/1980 | Boehringer et al. |
| 4,267,832 | A | 5/1981 | Hakkinen |
| 4,275,722 | A | 6/1981 | Sorensen |
| 4,298,023 | A | 11/1981 | McGinnis |
| 4,327,740 | A | 5/1982 | Shuman |
| 4,403,616 | A | 9/1983 | King |
| 4,436,090 | A | 3/1984 | Darling |
| 4,470,412 | A | 9/1984 | Nowacki et al. |
| 4,601,465 | A | 7/1986 | Roy |
| 4,611,591 | A | 9/1986 | Inui et al. |
| 4,635,631 | A | 1/1987 | Izumi |
| 4,651,731 | A | 3/1987 | Vicenzi et al. |
| 4,739,987 | A | 4/1988 | Nicholson |
| 4,770,413 | A | 9/1988 | Green |
| 4,973,047 | A | 11/1990 | Norell |
| 4,981,295 | A | 1/1991 | Belman et al. |
| 5,018,517 | A | 5/1991 | Liardet |
| 5,042,467 | A | 8/1991 | Foley |
| 5,065,746 | A | 11/1991 | Steen |
| 5,193,529 | A | 3/1993 | Labaere |
| 5,345,930 | A | 9/1994 | Cardinal et al. |
| 5,372,128 | A | 12/1994 | Haber et al. |
| 5,381,789 | A | 1/1995 | Marquardt |
| 5,451,190 | A | 9/1995 | Liardet |
| 5,479,920 | A | 1/1996 | Piper et al. |
| 5,540,220 | A | 7/1996 | Gropper et al. |
| 5,569,122 | A | 10/1996 | Cegla |
| 5,570,682 | A | 11/1996 | Johnson |
| 5,598,839 | A | 2/1997 | Niles et al. |
| 5,613,489 | A | 3/1997 | Miller |
| 5,645,049 | A | 7/1997 | Foley et al. |
| 5,647,345 | A | 7/1997 | Saul |
| 5,655,520 | A | 8/1997 | Howe |
| 5,658,221 | A | 8/1997 | Hougen |
| 5,727,546 | A | 3/1998 | Clarke et al. |
| 5,791,339 | A | 8/1998 | Winter |
| 5,829,429 | A | 11/1998 | Hughes |
| 5,848,588 | A | 12/1998 | Foley et al. |
| 5,862,802 | A | 1/1999 | Bird |
| 5,890,998 | A | 4/1999 | Hougen |
| 5,893,361 | A | 4/1999 | Hughes |
| 5,899,832 | A | 5/1999 | Hougen |
| 5,910,071 | A | 6/1999 | Hougen |
| 5,925,831 | A | 7/1999 | Storsved |
| 6,026,807 | A | 2/2000 | Puderbaugh et al. |
| 6,029,661 | A | 2/2000 | Whaley et al. |
| 6,044,841 | A | 4/2000 | Verdun et al. |
| 6,058,932 | A | 5/2000 | Hughes |
| 6,066,101 | A | 5/2000 | Johnson |
| 6,067,984 | A | 5/2000 | Piper |
| 6,083,141 | A | 7/2000 | Hougen |
| 6,089,105 | A | 7/2000 | Ricciardelli |
| 6,102,038 | A | 8/2000 | DeVries |
| 6,167,881 | B1 | 1/2001 | Hughes |
| 6,176,235 | B1 | 1/2001 | Benarrouch et al. |
| 6,182,657 | B1 | 2/2001 | Brydon et al. |
| D440,651 | S | 4/2001 | Foran |
| 6,240,917 | B1 | 6/2001 | Andrade |
| 6,253,766 | B1 | 7/2001 | Niles |
| 6,269,839 | B1 | 8/2001 | Wickham et al. |
| 6,293,279 | B1 | 9/2001 | Schmidt et al. |
| 6,340,025 | B1 | 1/2002 | Van Brunt |
| 6,345,617 | B1 | 2/2002 | Engelbreth et al. |
| 6,412,481 | B1 | 7/2002 | Bienvenu et al. |
| 6,446,629 | B1 | 9/2002 | Takaki et al. |
| 6,447,459 | B1 | 9/2002 | Larom |
| 6,500,095 | B1 | 12/2002 | Hougen |
| 6,557,549 | B2 | 5/2003 | Schmidt et al. |
| 6,581,595 | B1 | 6/2003 | Murdock et al. |
| 6,581,596 | B1 | 6/2003 | Truitt |
| 6,581,598 | B1 | 6/2003 | Foran et al. |
| 6,581,600 | B2 | 6/2003 | Bird |
| 6,595,203 | B1 | 7/2003 | Bird |
| 6,606,989 | B1 | 8/2003 | Brand |
| 6,607,008 | B1 | 8/2003 | Yoshimoto et al. |
| 6,615,831 | B1 | 9/2003 | Truitt |
| 6,631,721 | B1 | 10/2003 | Salter et al. |
| 6,659,100 | B2 | 12/2003 | O'Rourke |
| 6,702,769 | B1 | 3/2004 | Fowler-Hawkins |
| 6,708,690 | B1 | 3/2004 | Hete et al. |
| 6,708,691 | B1 | 3/2004 | Hayek |
| 6,726,598 | B1 | 4/2004 | Jarvis |
| D490,519 | S | 5/2004 | Pelerossi et al. |
| 6,776,159 | B2 | 8/2004 | Pelerossi et al. |
| 6,848,443 | B2 | 2/2005 | Schmidt et al. |
| 6,851,425 | B2 | 2/2005 | Jaffre |
| 6,904,906 | B2 | 6/2005 | Salter |
| 6,923,181 | B2 | 8/2005 | Tuck |
| 6,929,007 | B2 | 8/2005 | Emerson |
| 6,984,214 | B2 | 1/2006 | Fowler-Hawkins |
| 7,059,324 | B2 | 6/2006 | Pelerossi et al. |
| 7,096,866 | B2 | 8/2006 | Be'eri et al. |
| 7,134,434 | B2 | 11/2006 | Truitt et al. |
| 7,165,547 | B2 | 1/2007 | Truitt et al. |
| 7,188,621 | B2 | 3/2007 | DeVries |
| 7,191,776 | B2 | 3/2007 | Niles |
| 7,191,780 | B2 | 3/2007 | Faram |
| 7,214,170 | B2 | 5/2007 | Sumners et al. |
| 7,383,740 | B2 | 6/2008 | Krasilchikov et al. |
| 7,617,821 | B2 | 11/2009 | Hughes |
| 7,699,054 | B2 | 4/2010 | Pelerossi et al. |
| 7,717,847 | B2 | 5/2010 | Smith |
| 7,771,472 | B2 | 8/2010 | Hendricksen |
| 7,779,841 | B2 | 8/2010 | Dunsmore et al. |
| 7,798,148 | B2 | 9/2010 | Doshi |
| 7,856,979 | B2 | 12/2010 | Doshi |
| 7,909,033 | B2 | 3/2011 | Faram |
| 8,006,922 | B2 | 8/2011 | Katzer |
| 8,025,051 | B2 | 9/2011 | Dagsland |
| 8,025,054 | B2 | 9/2011 | Dunsmore et al. |
| 8,043,236 | B2 | 10/2011 | Abrammerovich et al. |
| 8,051,854 | B2 | 11/2011 | Faram |
| RE43,174 | E | 2/2012 | Schmidt et al. |
| 8,118,024 | B2 | 2/2012 | DeVries et al. |
| 8,118,713 | B2 | 2/2012 | Foley et al. |
| 8,225,785 | B2 | 7/2012 | Richards et al. |
| 8,327,849 | B2 | 12/2012 | Grychowski et al. |
| 8,460,223 | B2 | 6/2013 | Huster et al. |
| 8,469,029 | B2 | 6/2013 | Brown et al. |
| 8,485,179 | B1 | 7/2013 | Meyer |
| 8,539,179 | B1 | 9/2013 | Meyer et al. |
| 8,539,951 | B1 | 9/2013 | Meyer et al. |
| 8,985,111 | B2 | 3/2015 | Grychowski et al. |
| D731,050 | S | 6/2015 | Meyer |
| 9,149,589 | B2 | 10/2015 | Meyer et al. |

(56) References Cited

U.S. PATENT DOCUMENTS

| | | |
|---|---|---|
| 9,220,855 B2 | 12/2015 | Meyer |
| 2003/0015195 A1 | 1/2003 | Haaije de Boer et al. |
| 2007/0089740 A1 | 4/2007 | Baumert et al. |
| 2007/0259759 A1 | 11/2007 | Sumners et al. |
| 2008/0053456 A1 | 3/2008 | Brown et al. |
| 2008/0078383 A1 | 4/2008 | Richards et al. |
| 2008/0141363 A1 | 6/2008 | White |
| 2008/0257348 A1 | 10/2008 | Piper |
| 2009/0241949 A1 | 10/2009 | Smutney et al. |
| 2010/0139655 A1 | 7/2010 | Genosar |
| 2010/0307487 A1 | 12/2010 | Dunsmore et al. |
| 2012/0097164 A1 | 4/2012 | Rozario et al. |
| 2012/0234323 A1* | 9/2012 | Connor ............ A61M 16/0066 128/204.21 |
| 2012/0304988 A1* | 12/2012 | Meyer ................ A61M 16/208 128/203.12 |
| 2013/0133649 A1 | 5/2013 | Grychowski et al. |
| 2013/0184619 A1 | 7/2013 | Von Hollen et al. |
| 2013/0312746 A1 | 11/2013 | Grychowski |
| 2014/0041657 A1* | 2/2014 | Meyer ............... A61M 16/0066 128/203.12 |
| 2014/0150790 A1* | 6/2014 | Meyer ............... A61M 16/0057 128/204.18 |
| 2015/0013671 A1 | 1/2015 | Costella et al. |
| 2015/0053209 A1 | 2/2015 | Meyer et al. |
| 2015/0151060 A1 | 2/2015 | Grychowski et al. |
| 2015/0224269 A1 | 8/2015 | Alizoti et al. |
| 2015/0297848 A1 | 10/2015 | Meyer et al. |
| 2015/0374939 A1 | 12/2015 | Meyer et al. |
| 2016/0136369 A1 | 5/2016 | Meyer et al. |
| 2016/0310695 A1 | 10/2016 | Meyer et al. |
| 2017/0035986 A1* | 2/2017 | Quintero Osorio ......................... A61M 16/209 |
| 2017/0049979 A1 | 2/2017 | Meyer et al. |
| 2017/0157346 A1* | 6/2017 | Bennett ............ A61M 16/0866 |

FOREIGN PATENT DOCUMENTS

| | | |
|---|---|---|
| EP | 1435251 | 12/2003 |
| EP | 1 464 357 A1 | 10/2004 |
| EP | 1 435 251 B1 | 6/2006 |
| EP | 1 103 287 B1 | 6/2007 |
| EP | 1 897 576 A1 | 3/2008 |
| EP | 1 908 489 A1 | 4/2008 |
| EP | 2444114 | 4/2012 |
| EP | 2455137 | 5/2012 |
| GB | 2 425 488 A | 11/2006 |
| WO | WO 1989/03707 A1 | 5/1989 |
| WO | WO 1996/40376 | 12/1996 |
| WO | WO 1999/16490 | 4/1999 |
| WO | WO 2000/27455 | 5/2000 |
| WO | WO 2007/061648 A3 | 5/2007 |
| WO | WO 2007/119104 A3 | 10/2007 |
| WO | WO 2008/063966 A1 | 5/2008 |
| WO | WO 2008/122045 A1 | 10/2008 |
| WO | WO 2009/131965 | 10/2009 |
| WO | WO 2011/058470 | 5/2011 |
| WO | WO 2012/038864 A2 | 3/2012 |
| WO | WO 2016/012740 | 1/2016 |

OTHER PUBLICATIONS

International Search Report for related application No. PCT/IB2016/054577 (7 pgs).
U.S. Appl. No. 15/415,524, filed Jan. 25, 2017, Meyer et al.
U.S. Appl. No. 15/453,767, filed Mar. 8, 2017, Meyer et al.
U.S. Appl. No. 14/329,011, filed Jul. 11, 2014, Costella, et al.
U.S. Appl. No. 14/674,494, filed Mar. 31, 2015, Meyer et al.
U.S. Appl. No. 29/524,678, filed Apr. 22, 2015, Meyer et al.
U.S. Appl. No. 29/538,317, filed Sep. 2, 2015, Engelbreth et al.
U.S. Appl. No. 29/538,323, filed Sep. 2, 2015, Engelbreth et al.
Web page entitled Bronchial Hygiene, acapella Vibratory PEP Therapy System accessed from http://www.smiths-medical.com/catalog/bronchial-hygiene/acapella/acapella.html on Jul. 7, 2009.
Web page entitled Thayer Quake accessed from http://www.thayermedical.com/quake9.htm on Jul. 7, 2009.
Human growth hormone, cortisol, and acid-base balance changes after hyperventilation and breath-holding; PubMed—indexed for MEDLINE; Int J Sports Med., Dec. 1986; 7(6):311-5, Djarova T.
Bosco C, Cardinale M. & Tsarpela O (1999). Influence of vibration on mechanical power and electromyogram activity in human arm flexor muscles. Eur J Appl Physiol 79, 306-311.
David Sumners; Power Breathing and Strength; http://EzineArticles.com/972576 Published: Feb. 7, 2008.
Good Vibrations blog; http://vibrotraining.blogspot.com, Earliest posting Jan. 17, 2008.
Breathtaking News; More Youbreathe; Aug. 10, 2007.
PCT International Search Report for PCT/IB2012/001089, dated Oct. 5, 2012.
PCT International Written Opinion for PCT/IB2012/001089, dated Oct. 5, 2012.
International Preliminary Report on Patentability for related application No. PCT/IB2016/054577 (11 pgs), dated Feb. 8, 2018.

* cited by examiner

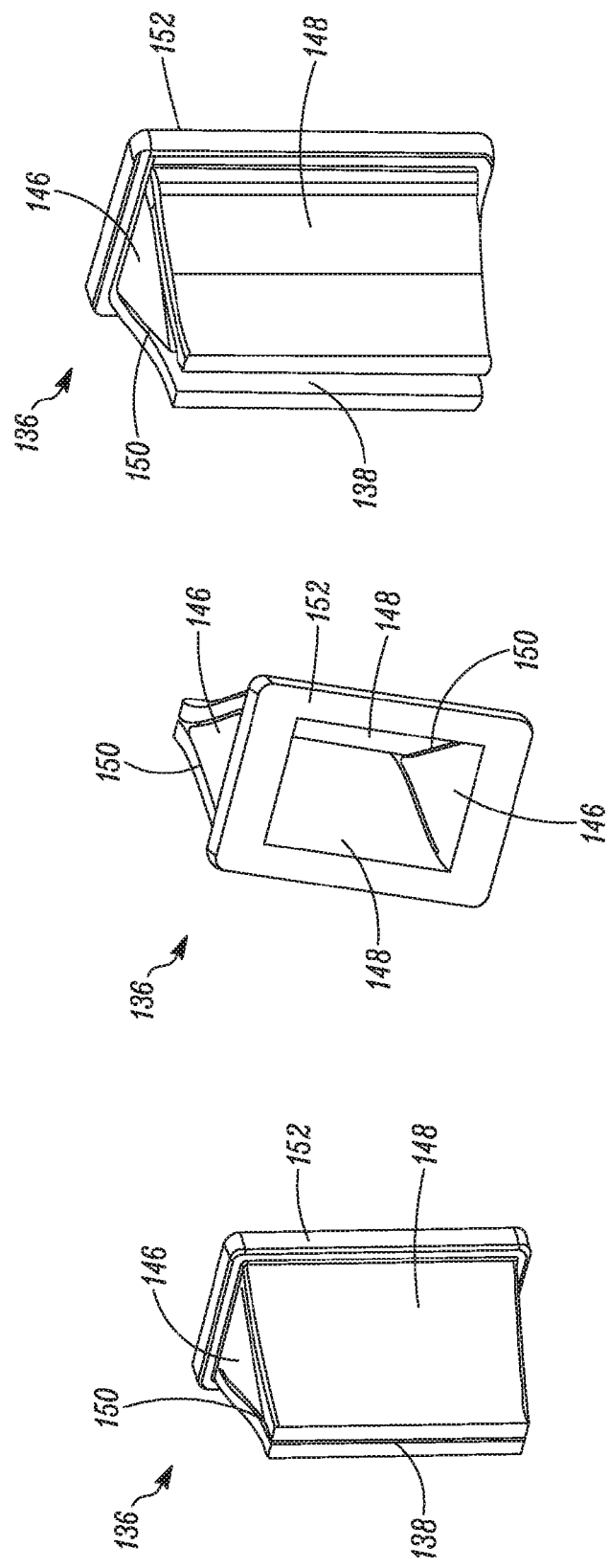

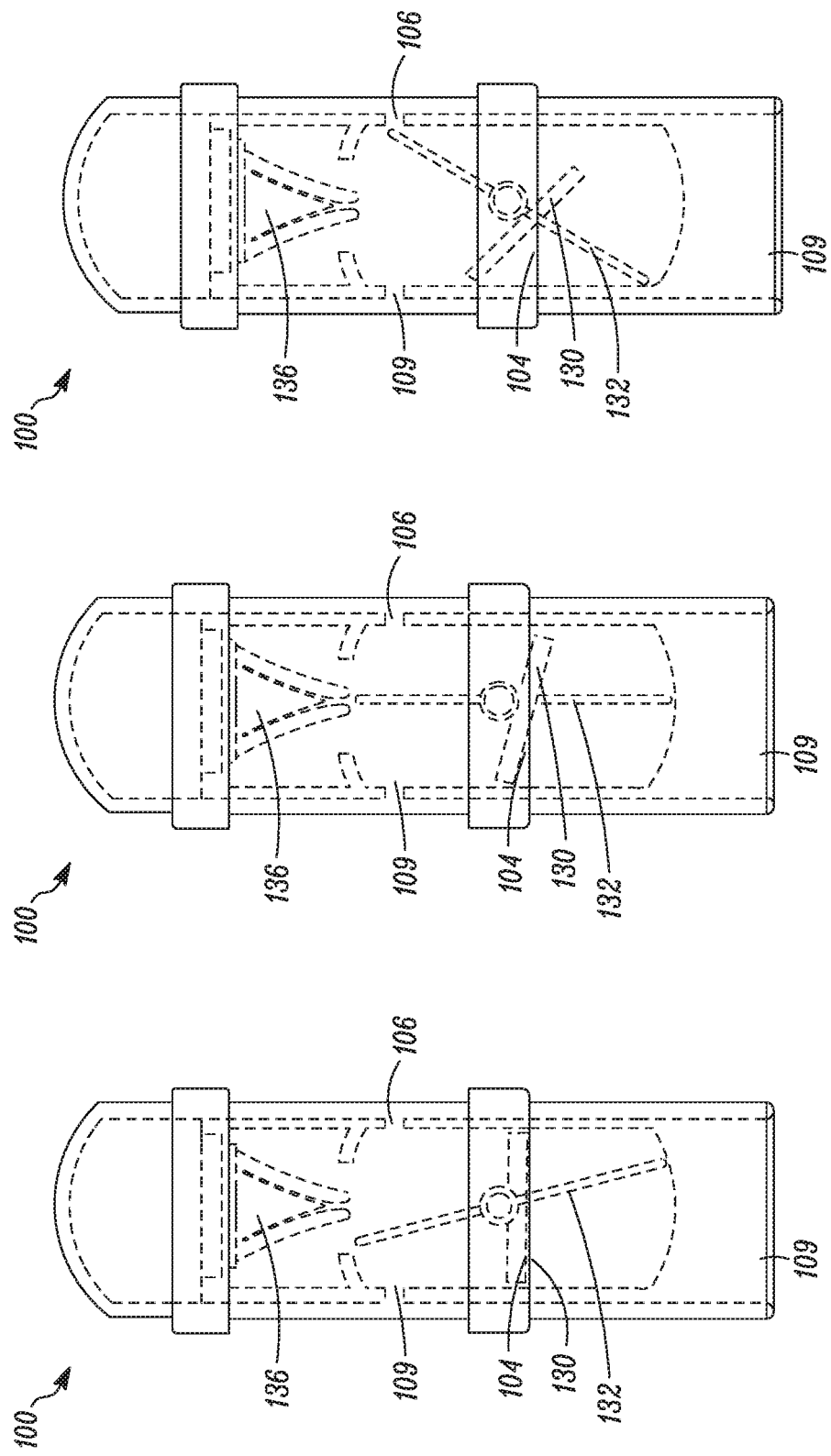

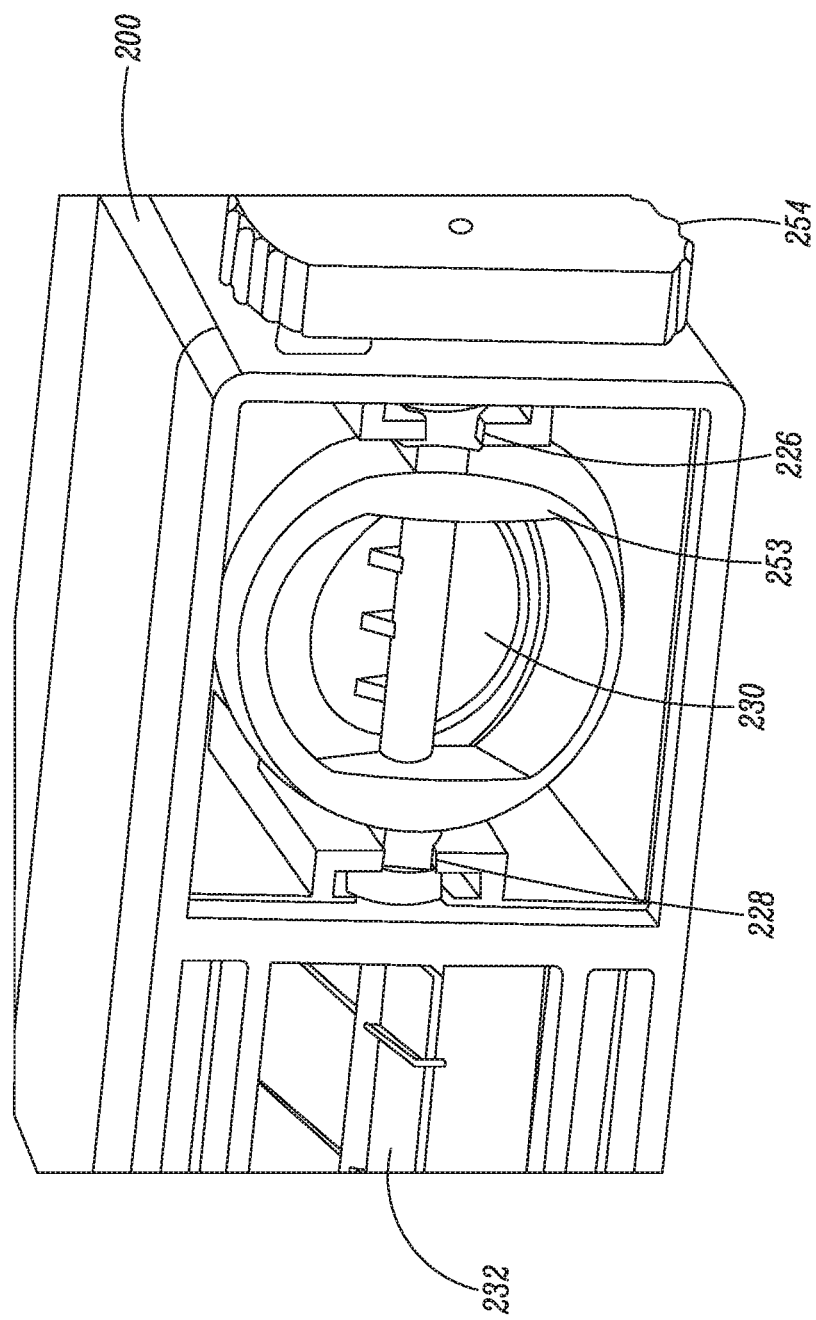

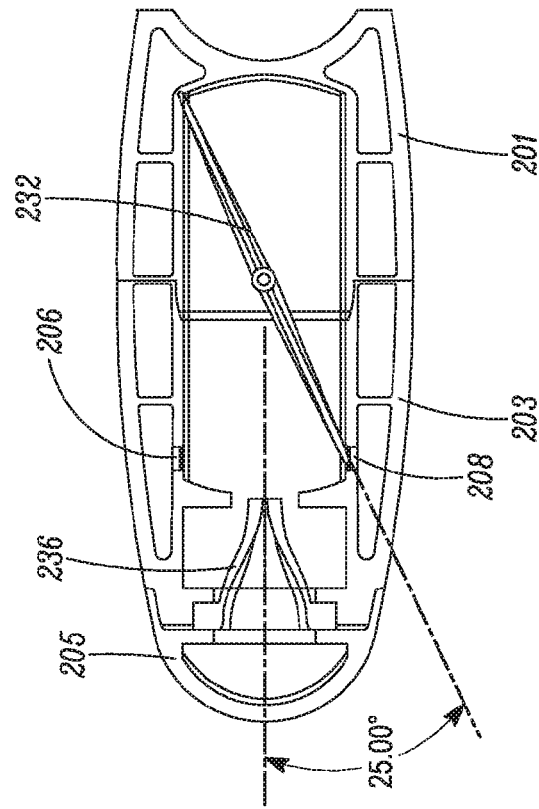
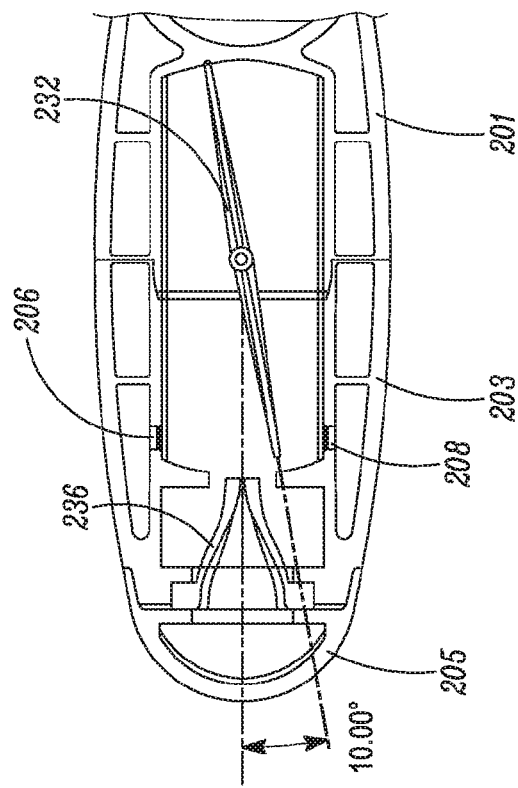

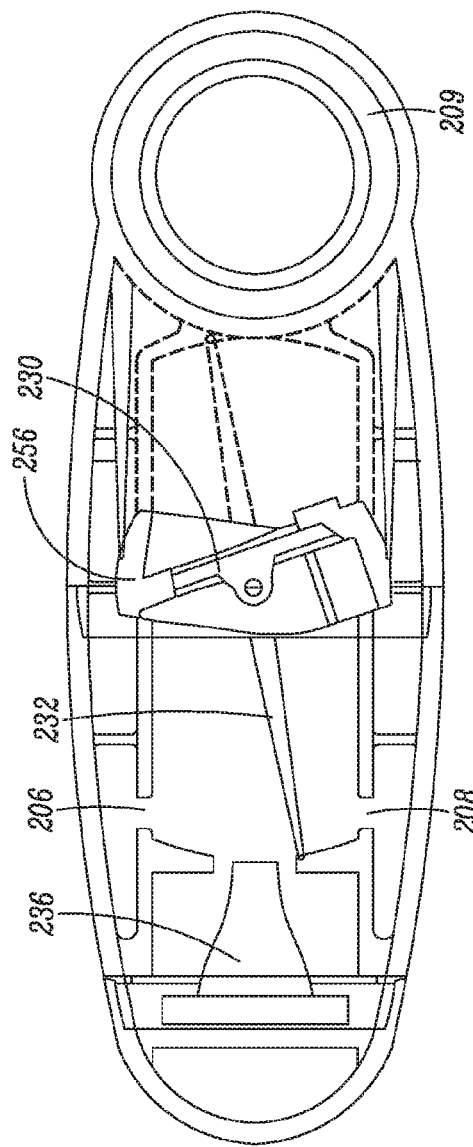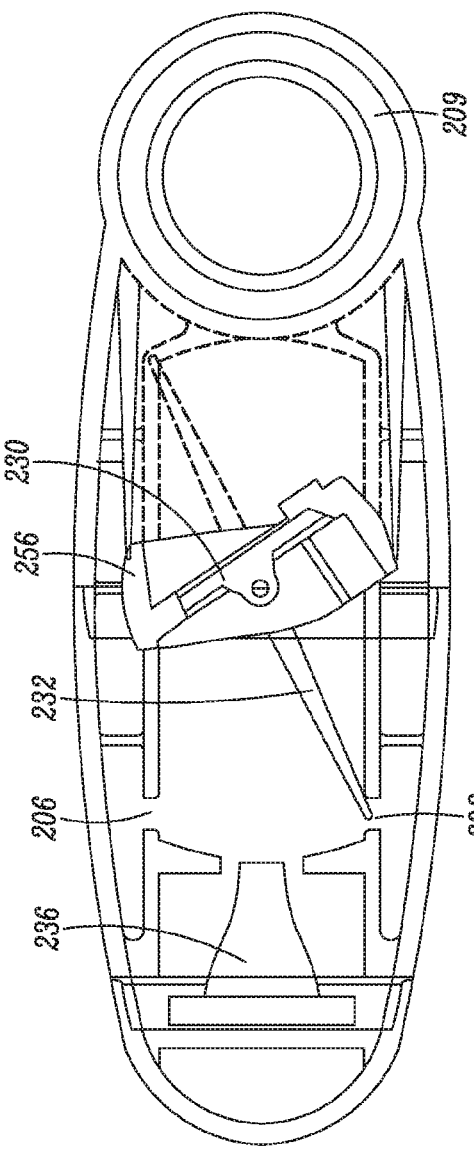

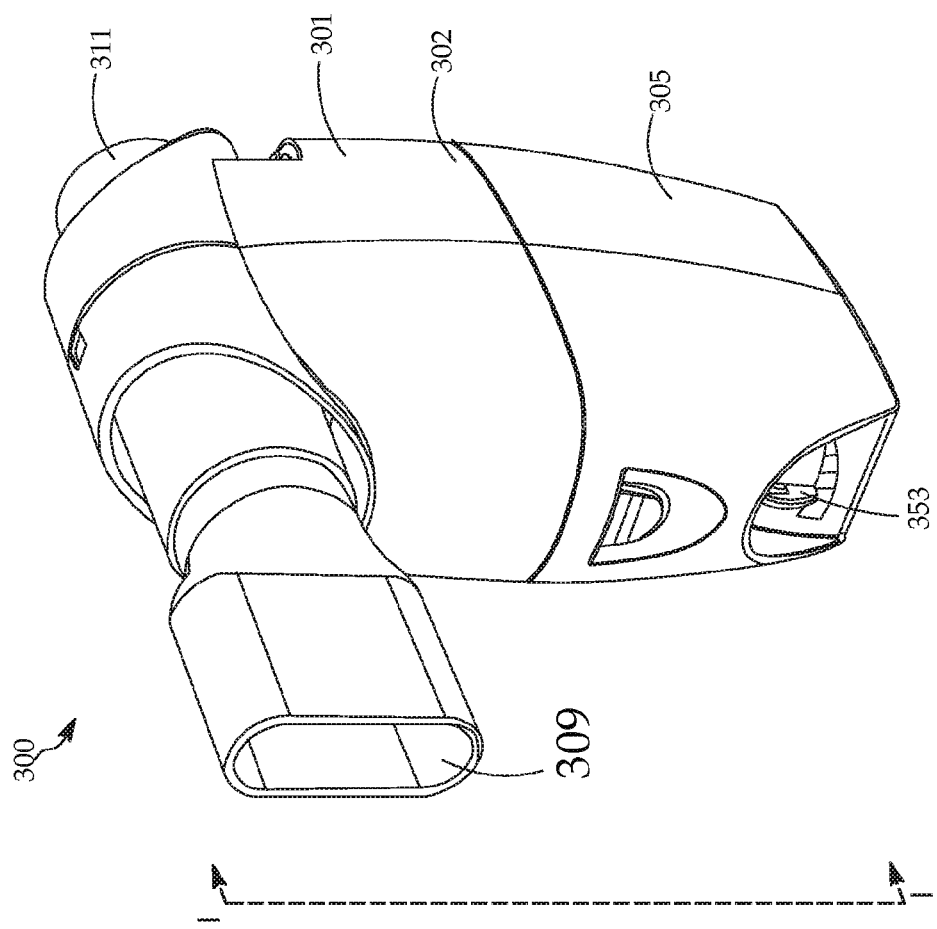

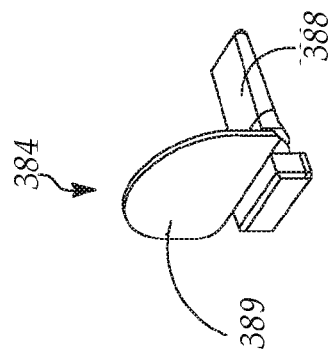
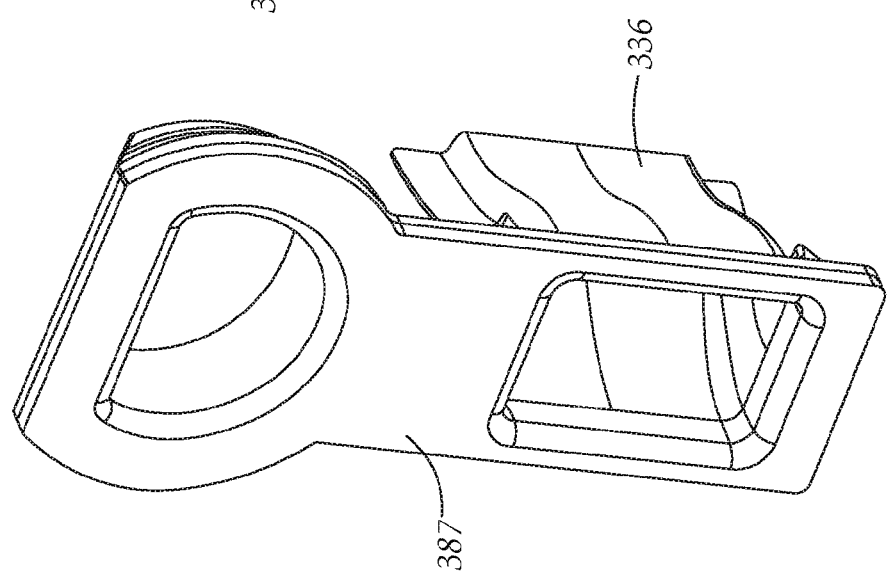
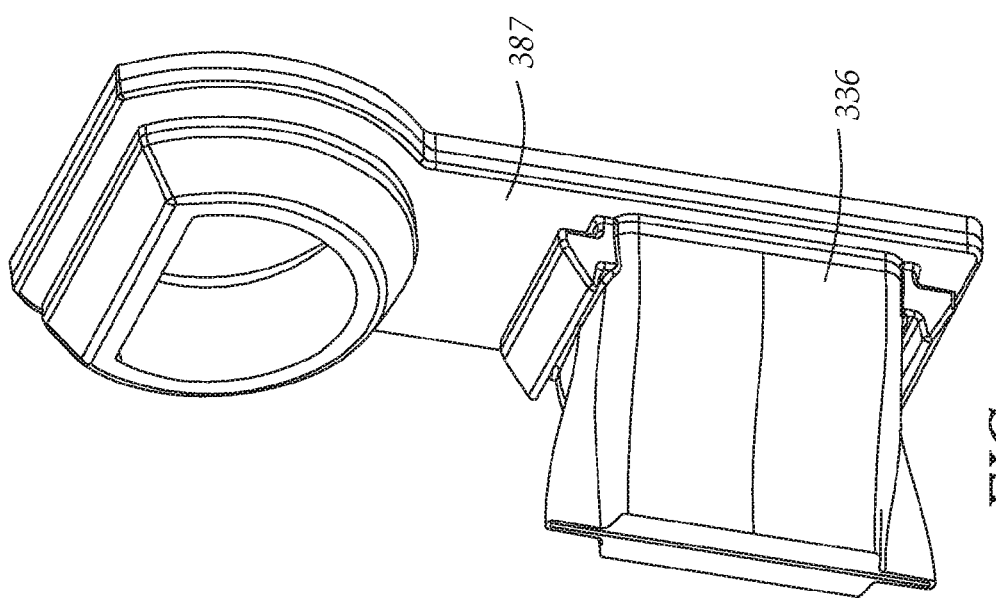

SECTION A-A

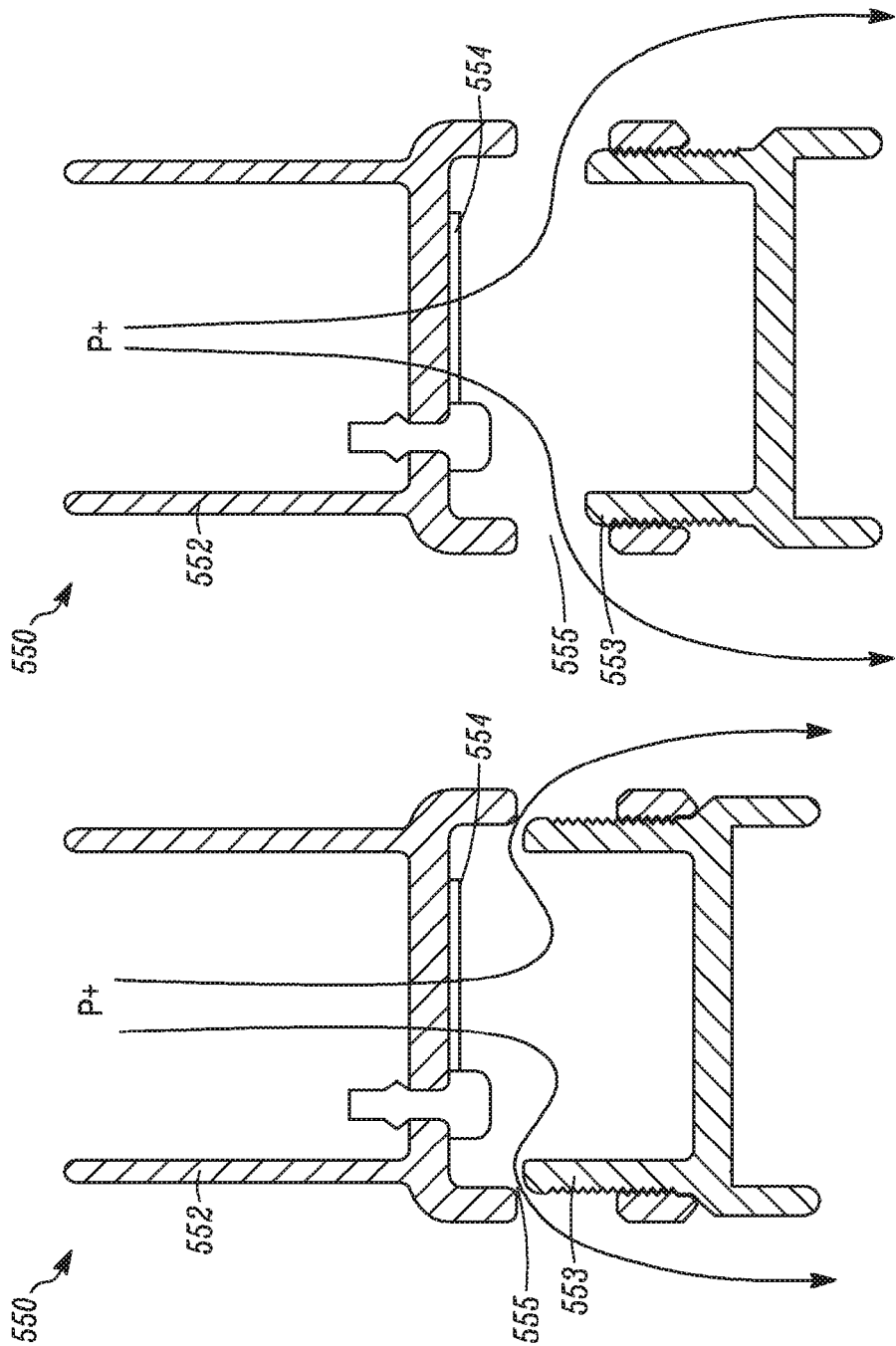

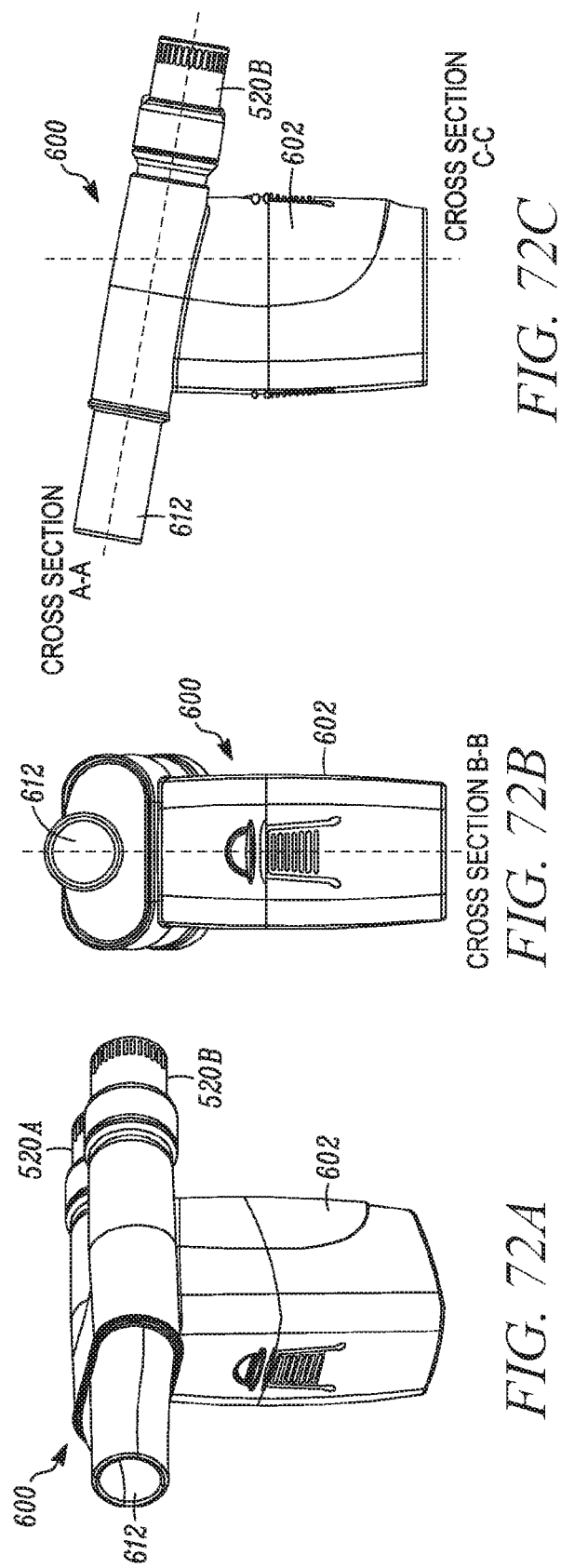

COMBINED RESPIRATORY MUSCLE TRAINING AND OSCILLATING POSITIVE EXPIRATORY PRESSURE DEVICE

RELATED APPLICATIONS

This application claims the benefit of U.S. Provisional Application No. 62/199,113, filed on Jul. 30, 2015, pending, the entirety of which is incorporated herein by reference.

TECHNICAL FIELD

The present disclosure relates to respiratory treatment devices, and in particular, to combined respiratory muscle training ("RMT") and oscillating positive expiratory pressure ("OPEP") devices.

BACKGROUND

Each day, humans may produce upwards of 30 milliliters of sputum, which is a type of bronchial secretion. Normally, an effective cough is sufficient to loosen secretions and clear them from the body's airways. However, for individuals suffering from more significant bronchial obstructions, such as collapsed airways, a single cough may be insufficient to clear the obstructions.

OPEP therapy represents an effective bronchial hygiene technique for the removal of bronchial secretions in the human body and is an important aspect in the treatment and continuing care of patients with bronchial obstructions, such as those suffering from chronic obstructive lung disease. It is believed that OPEP therapy, or the oscillation of exhalation pressure at the mouth during exhalation, effectively transmits an oscillating back pressure to the lungs, thereby splitting open obstructed airways and loosening the secretions contributing to bronchial obstructions. The benefits of OPEP therapy include decrease in sputum viscoelasticity, increase in forces disconnecting sputum from airway passages, and increase in sputum expectoration.

OPEP therapy is an attractive form of treatment because it can be easily taught to most patients, and such patients can assume responsibility for the administration of OPEP therapy throughout a hospitalization and also from home. To that end, a number of portable OPEP devices have been developed.

Like OPEP therapy, RMT has been shown to improve lung hygiene in both healthy individuals and patients with a variety of lung diseases. RMT includes pressure threshold resistance, which requires a user to achieve and maintain a set pressure during inhalation or exhalation, and flow resistance, which restricts the flow of air during inhalation or exhalation. The benefits of RMT include increased respiratory muscle strength, reduced dyspnea (breathlessness), increased exercise performance, and improved quality of life.

Like OPEP therapy, RMT is an attractive form of treatment because it can be easily taught to most patients, and such patients can assume responsibility for the administration of RMT therapy throughout a hospitalization and also from home.

In this regard, there is a need for a single device that performs both OPEP therapy and RMT, while maintaining the performance of individual devices that deliver only OPEP therapy or only RMT.

BRIEF SUMMARY

In one aspect, a respiratory treatment device includes a housing enclosing a plurality of chambers, with a first opening in the housing configured to transmit air exhaled into and air inhaled from the housing, a second opening in the housing configured to permit air exhaled into the first opening to exit the housing, and a third opening in the housing configured to permit air outside the housing to enter the housing upon inhalation at the first opening. An exhalation flow path is defined between the first opening and the second opening, and an inhalation flow path is defined between the third opening and the first opening. A restrictor member is positioned in the exhalation flow path and the inhalation flow path and is movable between a closed position, where a flow of air along the exhalation flow path or the inhalation flow path is restricted, and an open position, where the flow of exhaled air along the exhalation flow path or the inhalation flow path is less restricted. A vane is in fluid communication with the exhalation flow path and the inhalation flow path, and is connected to the restrictor member and configured to reciprocate between a first position and a second position in response to a flow of exhaled air along the exhalation flow path or the inhalation flow path.

In another aspect, the second opening may include a one-way exhalation valve configured to permit air exhaled into the housing to exit the housing upon exhalation at the first opening. The one-way exhalation valve may be configured to open in response to a positive threshold pressure. The threshold pressure may be selectively adjustable. The one-way exhalation valve may include a spring configured to bias the one-way valve toward a closed position. A level of bias may be selectively adjustable. A cross-sectional area of the second opening may be selectively adjustable to control a resistance to the flow of air therethrough.

In another aspect, the third opening may include a one-way inhalation valve configured to permit air outside the housing to enter the housing upon inhalation at the first opening. The one-way inhalation valve may be configured to open in response to a negative threshold pressure. The threshold pressure may be selectively adjustable. The one-way inhalation valve may include a spring configured to bias the one-way valve toward a closed position. A level of bias may be selectively adjustable. A cross-sectional area of the second opening may be selectively adjustable to control a resistance to the flow of air therethrough.

In yet another aspect, a one-way valve is positioned along the exhalation flow path between the first opening and the second opening. The one-way valve may be configured to open in response to air exhaled into the first opening, and close in response to air inhaled through the first opening.

In another aspect, a one-way valve is positioned along the inhalation flow path between the third opening and the first opening. The one-way valve may be configured to open in response to air inhaled through the first opening, and close in response to air exhaled into the first opening.

In another aspect, the restrictor member is positioned in a first chamber of the plurality of chambers, and the vane is positioned in a second chamber of the plurality of chambers. The flow of air through the first chamber is restricted when the restrictor member is in the closed position, and the flow of air through the first chamber is less restricted when the restrictor member is in the open position. The first chamber and the second chamber may be connected by an orifice. The vane is positioned adjacent the orifice and may be configured to move the restrictor member between the closed position and the open position in response to an increased pressure adjacent the vane.

In another aspect, the exhalation flow path and the inhalation flow path form an overlapping portion. The flow of air along the exhalation flow path and the inhalation flow path along the overlapping portion may be in the same direction. The restrictor member may be positioned in the overlapping portion, and the vane may be in fluid communication with the overlapping portion.

In another aspect, a size of the orifice is configured to increase in response to the flow of exhaled air through the orifice. The orifice may be formed within a variable nozzle. The orifice may be configured to close in response to a negative pressure from the flow of inhaled air along the inhalation flow path.

In another aspect, the vane is operatively connected to the restrictor member by a shaft. A face of the restrictor member is rotatable about an axis of rotation.

In yet another aspect, a flow resistor for a respiratory device includes a conduit for transmitting a flow of air. The conduit has a cross sectional area. A one-way valve is positioned within the conduit and is configured to open in response to the flow of air in a first direction, and close in response to the flow of air in a second direction. The one-way valve may have a cross-sectional area less than the cross sectional area of the conduit. An adjustment plate is positioned within the conduit forming an open section and a blocking section. The blocking section may have a cross-sectional area less than the cross-sectional area of the conduit. An orientation of the adjustment plate relative to the conduit may be selectively adjustable. The orientation of the open section relative to the cross-sectional area of the one-way valve is selectively adjustable. The adjustment plate may be positioned within the conduit adjacent to the one-way valve. A flow of air in the second direction may be permitted to flow around the one-way valve through the open section. The adjustment plate may be positioned within the conduit adjacent to the one-way valve. The one-way valve may be configured to open in response to inhalation by a user at a first end of the conduit, and close in response to exhalation by a user at the first end of the conduit.

In yet another aspect, a flow resistor for a respiratory device includes a housing defining a conduit for the flow of air therethrough, and a one-way valve positioned in the conduit. The one-way valve is configured to open in response to the flow of air through the conduit in a first direction and close in response to the flow of air through the conduit in a second direction. An opening in the conduit permits the flow of air into or out of the conduit. A cross-sectional area of the opening is selectively adjustable. The housing may include a first section and a second section, wherein a position of the first section of the housing relative to a position of the second section of the housing is selectively adjustable. Selective adjustment of the first section relative to the second section adjusts a cross-sectional area of the opening. The one-way valve may be positioned in the first section of the housing. The opening may be positioned in the first section of the housing.

In yet another aspect, a pressure threshold resistor includes a housing having a first section and a second section, the first section and the second section defining a conduit for the flow of air therethrough. A one-way valve is positioned in the conduit and is movable between a closed position, where the flow of air through the conduit is blocked, and an open position, where air is permitted to flow through the conduit. A biasing member may be configured to bias the one-way valve toward the closed position. The one-way valve may be configured to move from the closed position to an open position when a pressure in the conduit exceeds a threshold pressure.

In another aspect, the biasing member is a spring. A position of the first section of the housing relative to the second section of the housing may be selectively adjustable. Adjustment of the position of the first section of the housing relative to the second section of the housing may adjust the bias on the one-way valve. Adjustment of the position of the first section of the housing relative to the second section of the housing may adjust the threshold pressure. The biasing member may be a spring, and adjustment of the position of the first section of the housing relative to the second section may adjust a compression of the spring.

In yet another aspect, a respiratory treatment device includes a housing enclosing at least one chamber, a first opening in the housing configured to transmit air exhaled into and air inhaled from the housing, a second opening in the housing configured to permit air exhaled into the first opening to exit the housing, and a third opening in the housing configured to permit air outside the housing to enter the housing upon inhalation at the first opening. An exhalation flow path is defined between the first opening and the second opening, and an inhalation flow path defined between the third opening and the first opening. A restrictor member is positioned in the exhalation flow path and is movable between a closed position, where a flow of air along the exhalation flow path or is restricted, and an open position, where the flow of exhaled air along the exhalation flow path is less restricted.

In another aspect, a vane is in fluid communication with the exhalation flow path, is operatively connected to the restrictor member, and is configured to reciprocate between a first position and a second position in response to a flow of exhaled air along the exhalation flow path. The restrictor member may not be positioned in the inhalation flow path.

In another aspect, the third opening comprises a one-way inhalation valve configured to permit air outside the housing to enter the housing upon inhalation at the first opening. The one-way inhalation valve may be configured to open in response to a negative threshold pressure. The threshold pressure may be selectively adjustable. The one-way inhalation valve may include a spring configured to bias the one-way valve toward a closed position. The level of bias may be selectively adjustable. A cross-sectional area of the third opening may be selectively adjustable to control a resistance to the flow of air therethrough.

BRIEF DESCRIPTION OF THE DRAWINGS

FIG. 12 is a front perspective view of a variable nozzle shown without the flow of exhaled air therethrough;

FIG. 13 is a rear perspective view of the variable nozzle of FIG. 12 shown without the flow of exhaled air therethrough;

FIG. 14 is a front perspective view of the variable nozzle of FIG. 12 shown with a high flow of exhaled air therethrough;

FIGS. 15A-C are top phantom views of the OPEP device of FIG. 1 showing an exemplary illustration of the operation of the OPEP device of FIG. 1;

FIG. 28 is a partial cross-sectional view of the assembly of FIG. 27 within the OPEP device of FIG. 18;

FIGS. 32A-B are partial cross-sectional views taken along line III in FIG. 18 of the OPEP device, illustrating possible configurations of the OPEP device;

FIGS. 34A-B are top phantom views of the OPEP device of FIG. 18, illustrating the adjustability of the OPEP device;

FIG. 35 is a front perspective view of another embodiment of an OPEP device;

FIG. 50 is a front perspective view of a variable nozzle of the OPEP device of FIG. 35;

FIG. 51 is a rear perspective view of the variable nozzle of FIG. 50;

FIG. 52 is a front perspective view of the one-way valve of the OPEP device of FIG. 35;

FIGS. 69A-E are perspective and cross-sectional views of a flow resistor;

FIGS. 72A-C are perspective, front, and side views of a combined RMT and OPEP device;

DETAILED DESCRIPTION

OPEP Therapy

Figure 1:
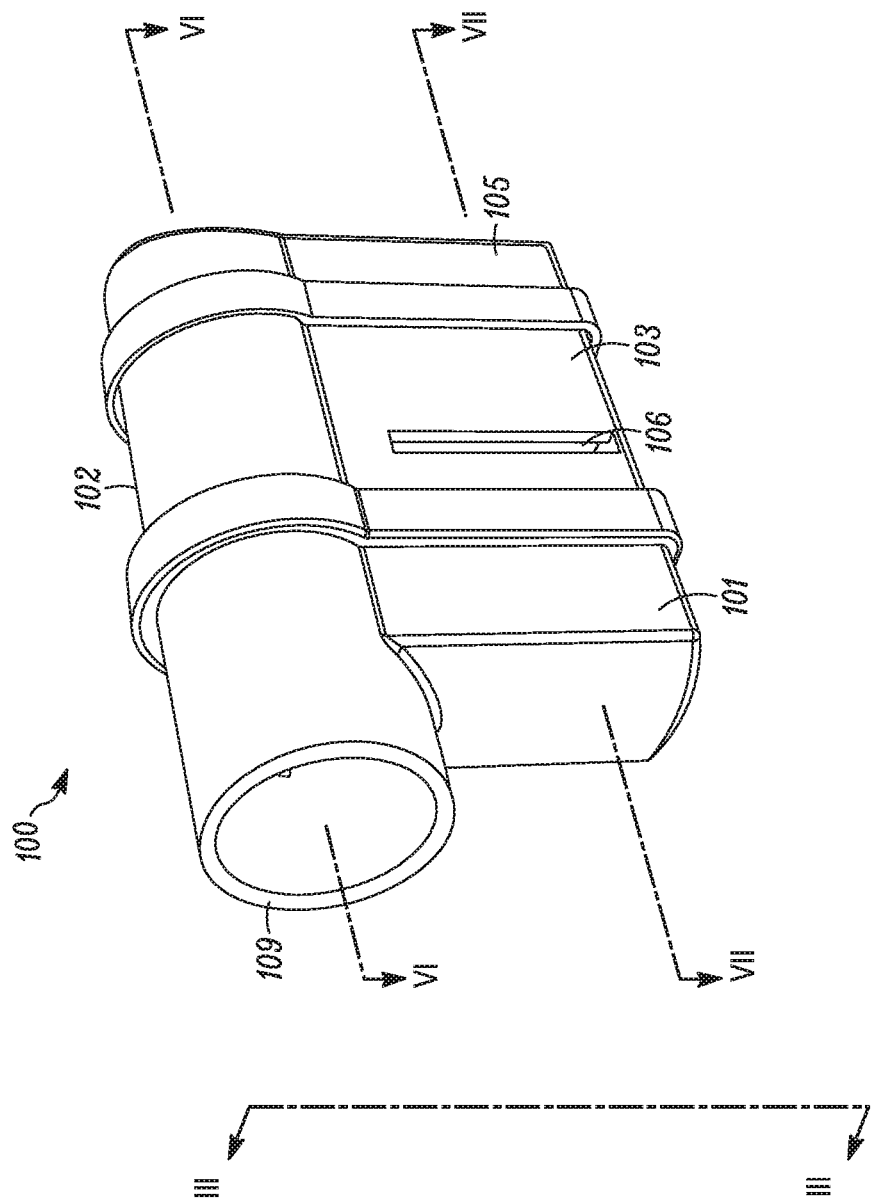
FIG. 1 is a front perspective view of an OPEP device.
Figure 2:
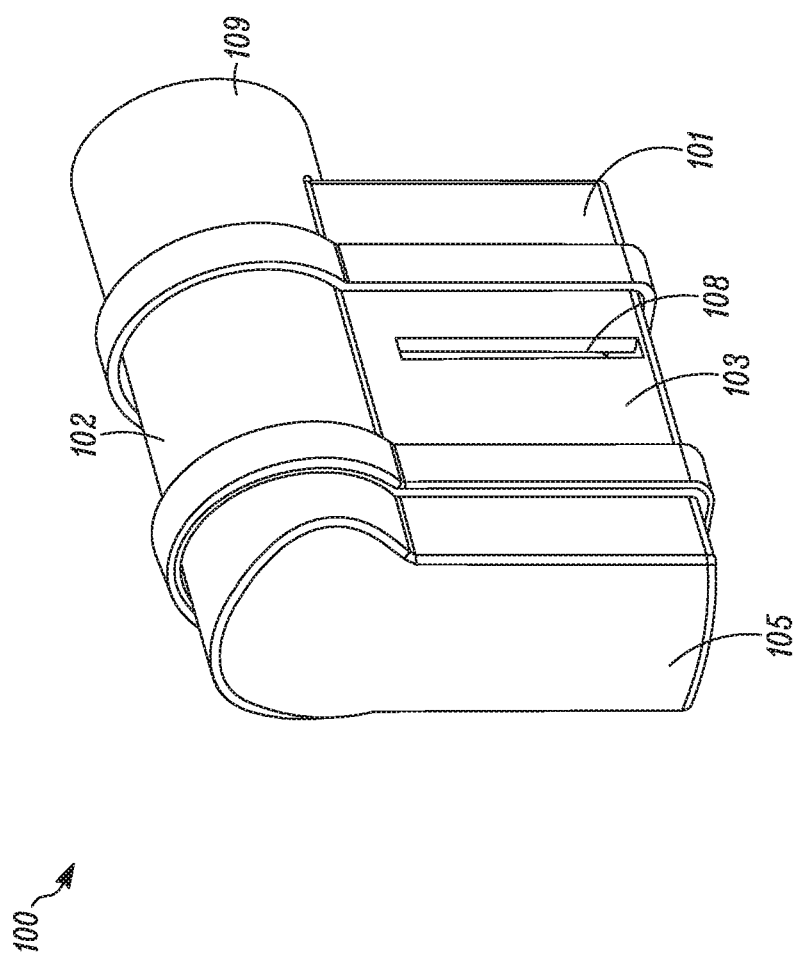
FIG. 2 is a rear perspective view of the OPEP device of FIG. 1.

OPEP therapy is effective within a range of operating conditions. For example, an adult human may have an exhalation flow rate ranging from 10 to 60 liters per minute, and may maintain a static exhalation pressure in the range of 8 to 18 cm $H_2O$. Within these parameters, OPEP therapy is believed to be most effective when changes in the exhalation pressure (i.e., the amplitude) range from 5 to 20 cm $H_2O$ oscillating at a frequency of 10 to 40 Hz. In contrast, an adolescent may have a much lower exhalation flow rate, and may maintain a lower static exhalation pressure, thereby altering the operating conditions most effective for the administration of OPEP therapy. Likewise, the ideal operating conditions for someone suffering from a respiratory illness, or in contrast, a healthy athlete, may differ from those of an average adult. As described below, the components of the disclosed OPEP devices are selectable and/or adjustable so that ideal operating conditions (e.g., amplitude and frequency of oscillating pressure) may be identified and maintained. Each of the various embodiments described herein achieve frequency and amplitude ranges that fall within the desired ranges set forth above. Each of the various embodiments described herein may also be configured to achieve frequencies and amplitudes that fall outside the ranges set forth above.

First OPEP Embodiment

Referring first to FIGS. 1-4, a front perspective view, a rear perspective view, a cross-sectional front perspective view, and an exploded view of an OPEP device 100 are shown. For purposes of illustration, the internal components of the OPEP device 100 are omitted in FIG. 3. The OPEP device 100 generally comprises a housing 102, a chamber inlet 104, a first chamber outlet 106, a second chamber outlet 108 (best seen in FIGS. 2 and 7), and a mouthpiece 109 in fluid communication with the chamber inlet 104. While the mouthpiece 109 is shown in FIGS. 1-4 as being integrally formed with the housing 102, it is envisioned that the mouthpiece 109 may be removable and replaceable with a mouthpiece 109 of a different size or shape, as required to maintain ideal operating conditions. In general, the housing 102 and the mouthpiece 109 may be constructed of any durable material, such as a polymer. One such material is Polypropylene. Alternatively, acrylonitrile butadiene styrene (ABS) may be used.

Alternatively, other or additional interfaces, such as breathing tubes or gas masks (not shown) may be attached in fluid communication with the mouthpiece 109 and/or associated with the housing 102. For example, the housing 102 may include an inhalation port (not shown) having a separate one-way inhalation valve (not shown) in fluid communication with the mouthpiece 109 to permit a user of the OPEP device 100 both to inhale the surrounding air through the one-way valve, and to exhale through the chamber inlet 104 without withdrawing the mouthpiece 109 of the OPEP device 100 between periods of inhalation and exhalation. In addition, any number of aerosol delivery devices may be connected to the OPEP device 100, for example, through the inhalation port mentioned above, for the simultaneous administration of aerosol and OPEP therapies. As such, the inhalation port may include, for example, an elastomeric adapter, or other flexible adapter, capable of accommodating the different mouthpieces or outlets of the particular aerosol delivery device that a user intends to use with the OPEP device 100. As used herein, the term aerosol delivery devices should be understood to include, for example, without limitation, any nebulizer, soft mist inhaler, pressurized metered dose inhaler, dry powder inhaler, combination of a holding chamber a pressurized metered dose inhaler, or the like. Suitable commercially available aerosol delivery devices include, without limitation, the AEROECLIPSE nebulizer, RESPIMAT soft mist inhaler, LC Sprint nebulizer, AEROCHAMBER PLUS holding chambers, MICRO MIST nebulizer, SIDESTREAM nebulizers, Inspiration Elite nebulizers, FLOVENT pMDI, VENTOLIN pMDI, AZMACORT pMDI, BECLOVENT pMDI, QVAR pMDI and AEROBID PMDI, XOPENEX pMDI, PROAIR pMDI, PROVENT pMDI, SYMBICORT pMDI, TURBOHALER DPI, and DISKHALER DPI. Descriptions of suitable aerosol delivery devices may be found in U.S. Pat. Nos. 4,566,452; 5,012,803; 5,012,804; 5,312,046; 5,497,944; 5,622,162; 5,823,179; 6,293,279; 6,435,177; 6,484,717; 6,848,443; 7,360,537; 7,568,480; and, 7,905,228, the entireties of which are herein incorporated by reference.

In FIGS. 1-4, the housing 102 is generally box-shaped. However, a housing 102 of any shape may be used. Furthermore, the chamber inlet 104, the first chamber outlet 106, and the second chamber outlet 108 could be any shape or series of shapes, such as a plurality (i.e., more than one) of circular passages or linear slots. More importantly, it should be appreciated that the cross-sectional area of the chamber inlet 104, the first chamber outlet 106, and the second chamber outlet 108 are only a few of the factors influencing the ideal operating conditions described above.

Preferably, the housing 102 is openable so that the components contained therein can be periodically accessed, cleaned, replaced, or reconfigured, as required to maintain the ideal operating conditions. As such, the housing 102 is shown in FIGS. 1-4 as comprising a front section 101, a middle section 103, and a rear section 105. The front section 101, the middle section 103, and the rear section 105 may be removably connected to one another by any suitable means, such as a snap-fit, a compression fit, etc., such that a seal forms between the relative sections sufficient to permit the OPEP device 100 to properly administer OPEP therapy.

Figure 3:
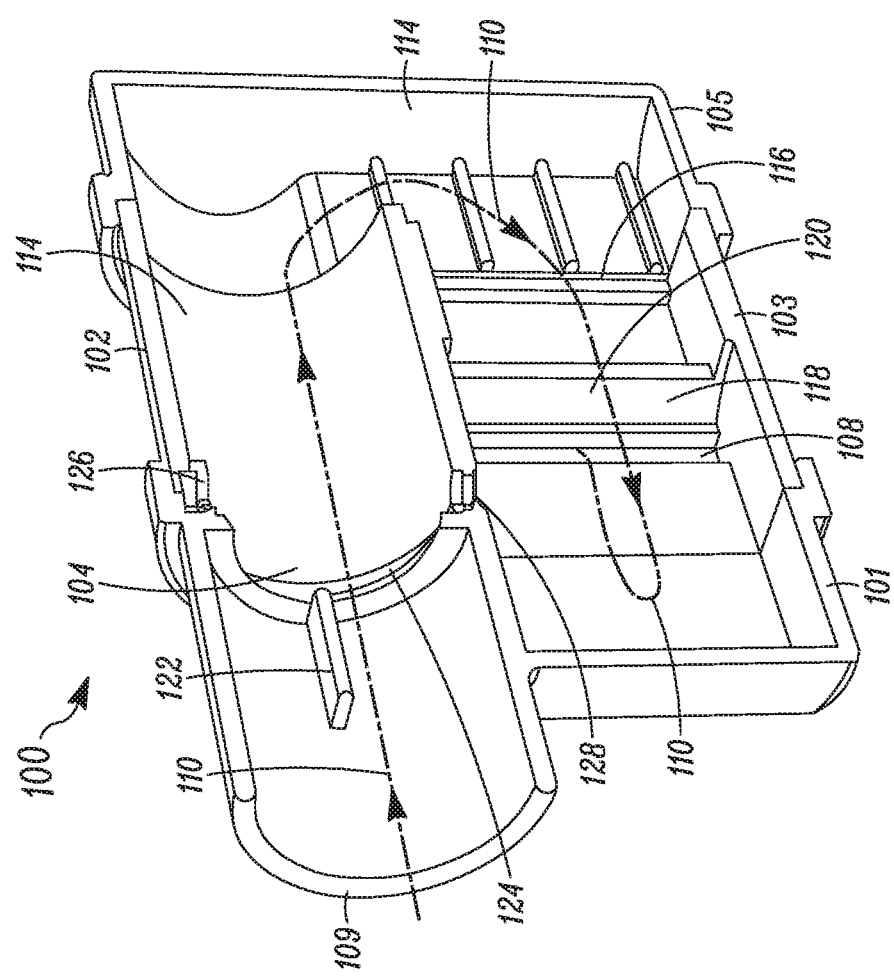
FIG. 3 is a cross-sectional perspective view taken along line III in FIG. 1 of the OPEP device shown without the internal components of the OPEP device.
Figure 7:
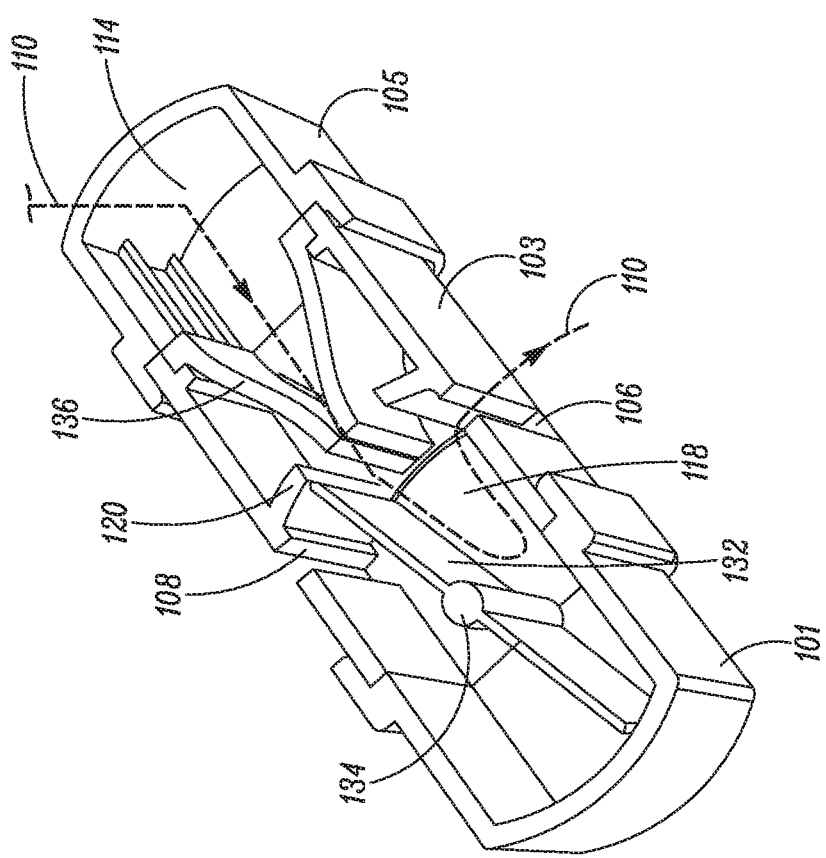
FIG. 7 is a different cross-sectional perspective view taken along line VII in FIG. 1 of the OPEP device shown with the internal components of the OPEP device.

As shown in FIG. 3, an exhalation flow path 110, identified by a dashed line, is defined between the mouthpiece 109 and at least one of the first chamber outlet 106 and the second chamber outlet 108 (best seen in FIG. 7). More specifically, the exhalation flow path 110 begins at the mouthpiece 109, passes through the chamber inlet 104, and enters into a first chamber 114, or an entry chamber. In the first chamber 114, the exhalation flow path makes a 180-degree turn, passes through a chamber passage 116, and enters into a second chamber 118, or an exit chamber. In the second chamber 118, the exhalation flow path 110 may exit the OPEP device 100 through at least one of the first chamber outlet 106 and the second chamber outlet 108. In this way, the exhalation flow path 110 is "folded" upon itself, i.e., it reverses longitudinal directions between the chamber inlet 104 and one of the first chamber outlet 106 or the second chamber outlet 108. However, those skilled in the art will appreciate that the exhalation flow path 110 identified by the dashed line is exemplary, and that air exhaled into the OPEP device 100 may flow in any number of directions or paths as it traverses from the mouthpiece 109 or chamber inlet 104 and the first chamber outlet 106 or the second chamber outlet 108.

FIG. 3 also shows various other features of the OPEP device 100 associated with the housing 102. For example, a stop 122 prevents a restrictor member 130 (see FIG. 5), described below, from opening in a wrong direction; a seat 124 shaped to accommodate the restrictor member 130 is formed about the chamber inlet 104; and, an upper bearing 126 and a lower bearing 128 are formed within the housing 102 and configured to accommodate a shaft rotatably mounted therebetween. One or more guide walls 120 are positioned in the second chamber 118 to direct exhaled air along the exhalation flow path 110.

Figure 5:
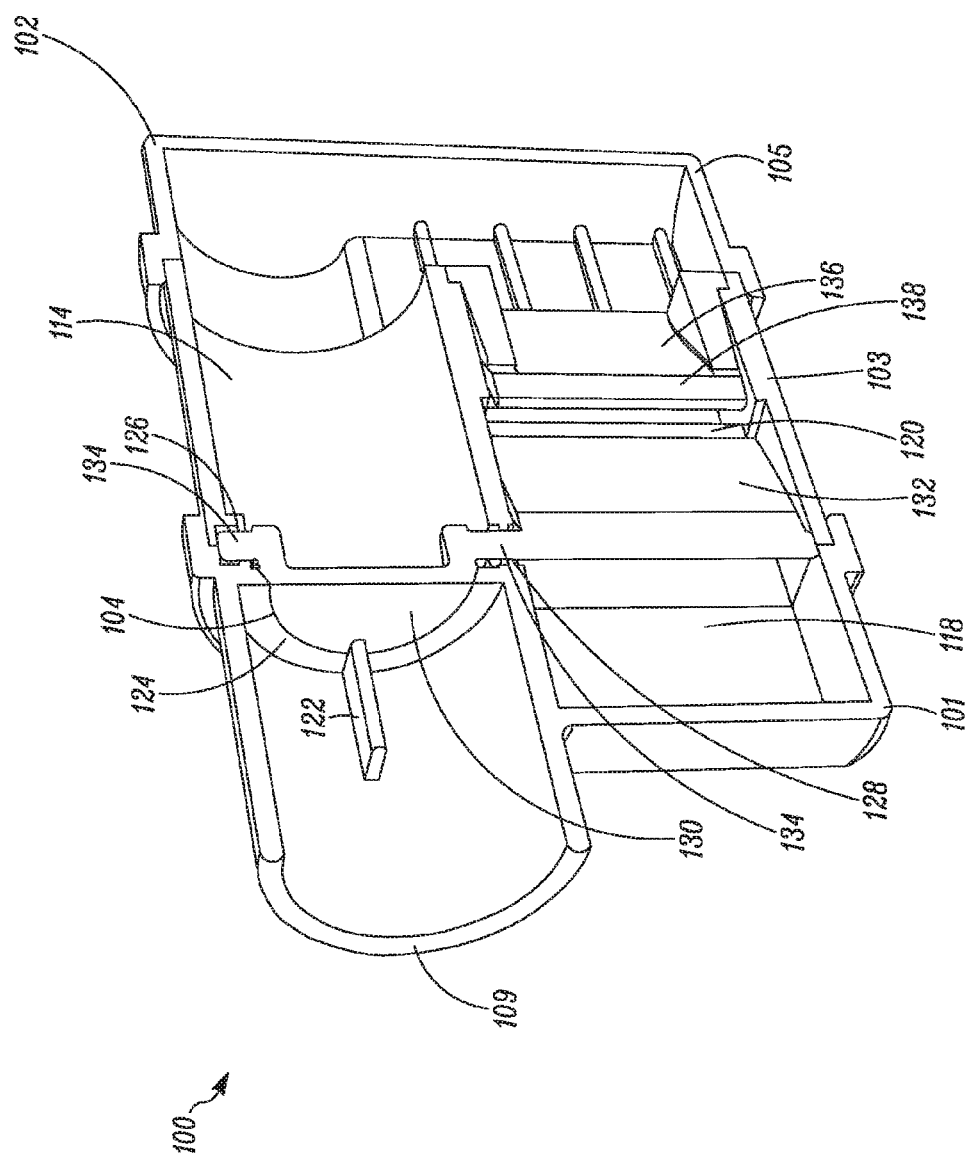
FIG. 5 is a cross-sectional perspective view taken along line III in FIG. 1 of the OPEP device shown with the internal components of the OPEP device.
Figure 6:
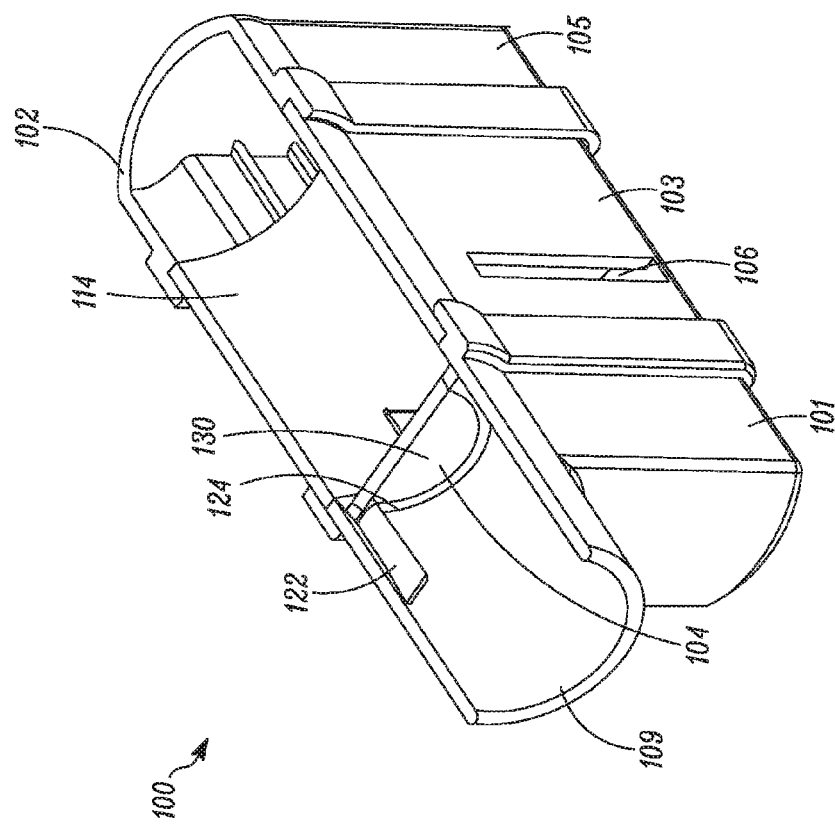
FIG. 6 is a different cross-sectional perspective view taken along line VI in FIG. 1 of the OPEP device shown with the internal components of the OPEP device.

Turning to FIGS. 5-7, various cross-sectional perspective views of the OPEP device 100 are shown with its internal components. The internal components of the OPEP device 100 comprise a restrictor member 130, a vane 132, and an optional variable nozzle 136. As shown, the restrictor member 130 and the vane 132 are operatively connected by means of a shaft 134 rotatably mounted between the upper bearing 126 and the lower bearing 128, such that the restrictor member 130 and the vane 132 are rotatable in unison about the shaft 134. As described below in further detail, the variable nozzle 136 includes an orifice 138 configured to increase in size in response to the flow of exhaled air therethrough.

Figure 4:
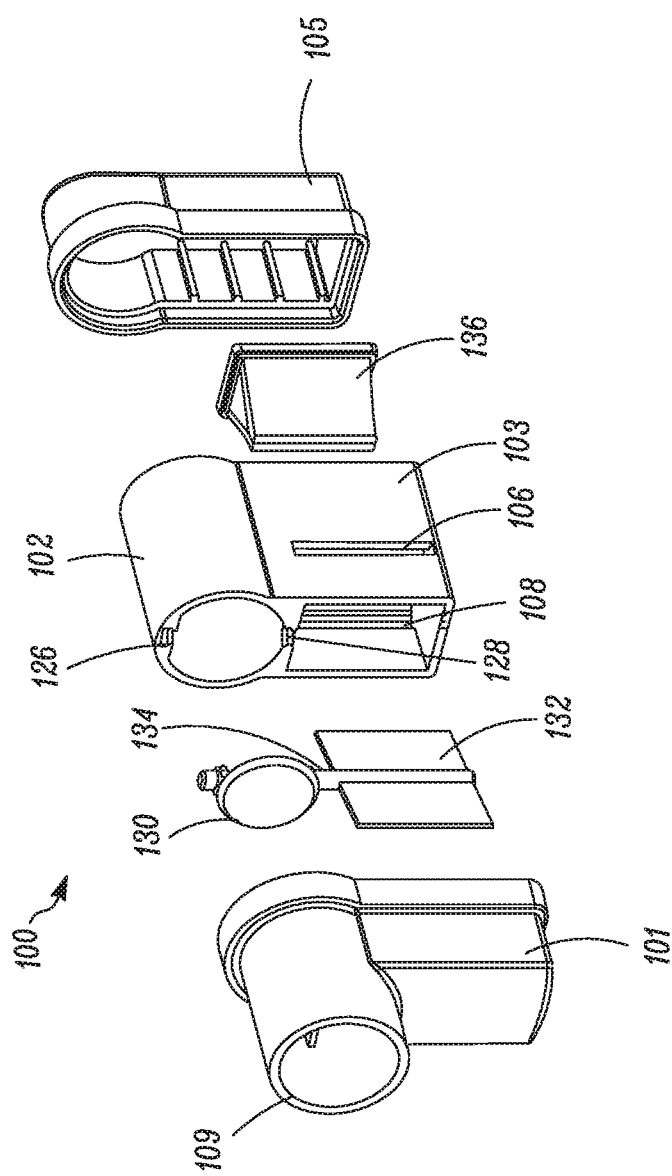
FIG. 4 is an exploded view of the OPEP device of FIG. 1, shown with the internal components of the OPEP device.

FIGS. 4-6 further illustrate the division of the first chamber 114 and the second chamber 118 within the housing 102. As previously described, the chamber inlet 104 defines an entrance to the first chamber 114. The restrictor member 130 is positioned in the first chamber 114 relative to a seat 124 about the chamber inlet 104 such that it is moveable between a closed position, where a flow of exhaled air along the exhalation flow path 110 through the chamber inlet 104 is restricted, and an open position, where the flow of exhaled air through the chamber inlet 104 is less restricted. Likewise, the variable nozzle 136, which is optional, is mounted about or positioned in the chamber passage 116, such that the flow of exhaled air entering the first chamber 114 exits the first chamber 114 through the orifice 138 of the variable nozzle 136. Exhaled air exiting the first chamber 114 through the orifice 138 of the variable nozzle 136 enters the second chamber, which is defined by the space within the housing 102 occupied by the vane 132 and the guide walls 120. Depending on the position of the vane 132, the exhaled air is then able to exit the second chamber 118 through at least one of the first chamber outlet 106 and the second chamber outlet 108.

Figure 8:
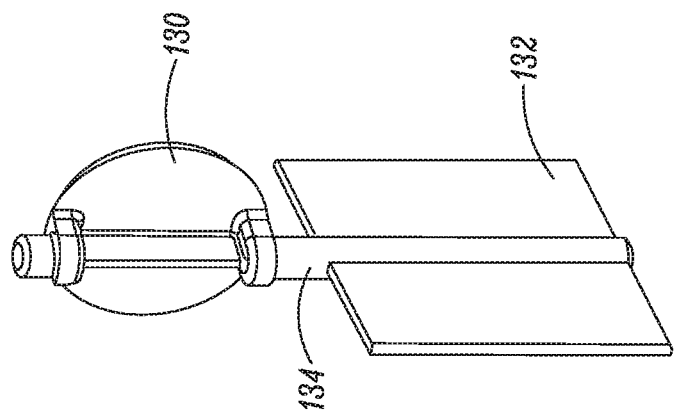
FIG. 8 is a front perspective view of a restrictor member operatively connected to a vane.
Figure 9:
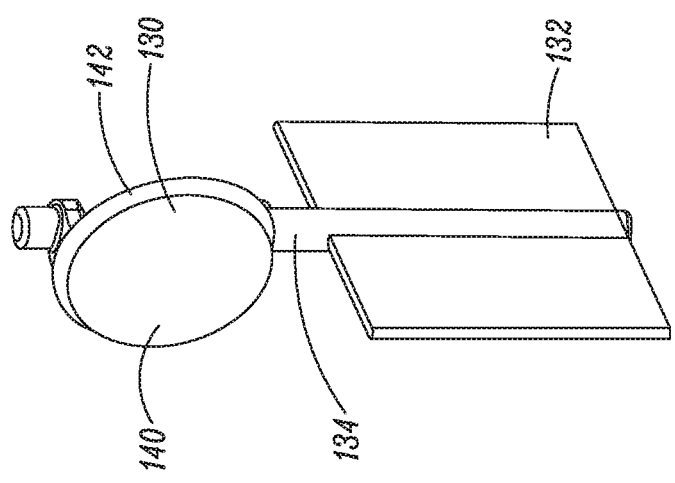
FIG. 9 is a rear perspective view of the restrictor member operatively connected to the vane shown in FIG. 8.

FIGS. 8-14 show the internal components of the OPEP device 100 in greater detail. Turning first to FIGS. 8-9, a front perspective view and a rear perspective view shows the restrictor member 130 operatively connected to the vane 132 by the shaft 134. As such, the restrictor member 130 and the vane 132 are rotatable about the shaft 134 such that rotation of the restrictor member 130 results in a corresponding rotation of the vane 132, and vice-versa. Like the housing 102, the restrictor member 130 and the vane 132 may be made of constructed of any durable material, such as a polymer. Preferably, they are constructed of a low shrink, low friction plastic. One such material is acetal.

As shown, the restrictor member 130, the vane 132, and the shaft 134 are formed as a unitary component. The restrictor member 130 is generally disk-shaped, and the vane 132 is planar. The restrictor member 130 includes a generally circular face 140 axially offset from the shaft 134 and a beveled or chamfered edge 142 shaped to engage the seat 124 formed about the chamber inlet 104. In this way, the restrictor member 130 is adapted to move relative to the chamber inlet 104 about an axis of rotation defined by the shaft 134 such that the restrictor member 130 may engage the seat 124 in a closed position to substantially seal and restrict the flow of exhaled air through the chamber inlet 104. However, it is envisioned that the restrictor member 130 and the vane 132 may be formed as separate components connectable by any suitable means such that they remain independently replaceable with a restrictor member 130 or a vane 132 of a different shape, size, or weight, as selected to maintain ideal operating conditions. For example, the restrictor member 130 and/or the vane 132 may include one or more contoured surfaces. Alternatively, the restrictor member 130 may be configured as a butterfly valve.

Figure 10:
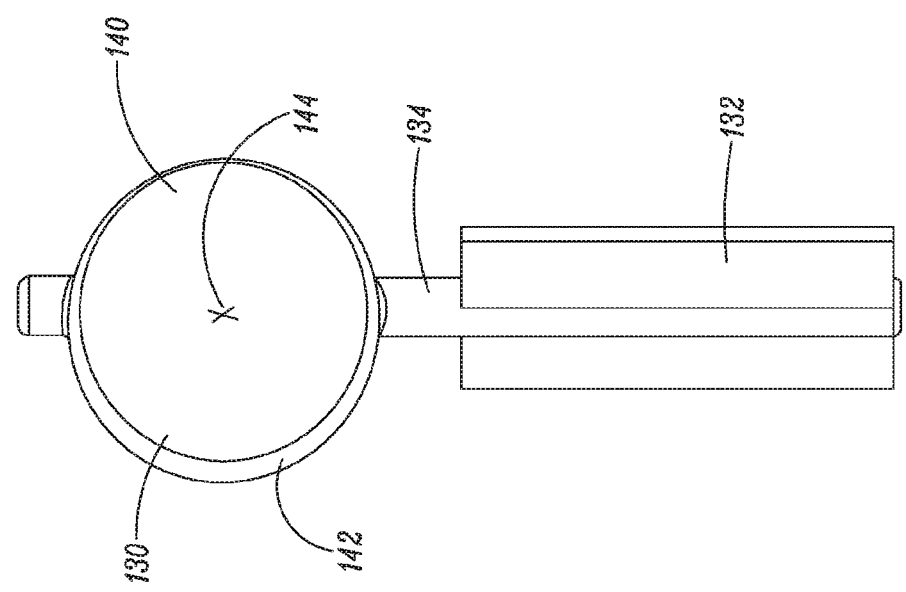
FIG. 10 is a front view of the restrictor member operatively connected to the vane shown in FIG. 8.

Turning to FIG. 10, a front view of the restrictor member 130 and the vane 132 is shown. As previously described, the restrictor member 130 comprises a generally circular face 140 axially offset from the shaft 134. The restrictor member 130 further comprises a second offset designed to facilitate movement of the restrictor member 130 between a closed position and an open position. More specifically, a center 144 of the face 140 of the restrictor member 130 is offset from the plane defined by the radial offset and the shaft 134, or the axis of rotation. In other words, a greater surface area of the face 140 of the restrictor member 130 is positioned on one side of the shaft 134 than on the other side of the shaft 134. Pressure at the chamber inlet 104 derived from exhaled air produces a force acting on the face 140 of the restrictor member 130. Because the center 144 of the face 140 of the restrictor member 130 is offset as described above, a resulting force differential creates a torque about the shaft 134. As further explained below, this torque facilitates movement of the restrictor member 130 between a closed position and an open position.

Figure 11:
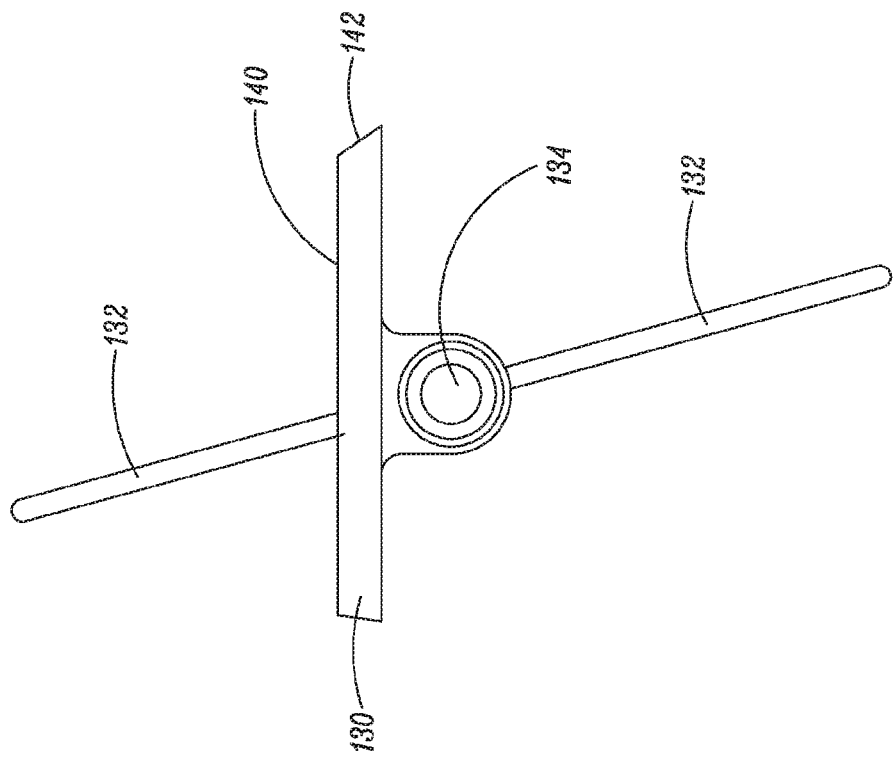
FIG. 11 is a top view of the restrictor member operatively connected to the vane shown in FIG. 8.

Turning to FIG. 11, a top view of the restrictor member 130 and the vane 132 is shown. As illustrated, the vane 132 is connected to the shaft 134 at a 75° angle relative to the face 140 of restrictor member 130. Preferably, the angle will remain between 60° and 80°, although it is envisioned that the angle of the vane 132 may be selectively adjusted to maintain the ideal operating conditions, as previously discussed. It is also preferable that the vane 132 and the restrictor member 130 are configured such that when the OPEP device 100 is fully assembled, the angle between a centerline of the variable nozzle 136 and the vane 132 is between 10° and 25° when the restrictor member 130 is in a closed position. Moreover, regardless of the configuration, it is preferable that the combination of the restrictor member 130 and the vane 132 have a center of gravity aligned with the shaft 134, or the axis of rotation. In full view of the present disclosure, it should be apparent to those skilled in the art that the angle of the vane 132 may be limited by the size or shape of the housing 102, and will generally be less than half the total rotation of the vane 132 and the restrictor member 130.

Turning to FIGS. 12 and 13, a front perspective view and a rear perspective view of the variable nozzle 136 is shown without the flow of exhaled air therethrough. In general, the variable nozzle 136 includes top and bottom walls 146, side walls 148, and V-shaped slits 150 formed therebetween. As shown, the variable nozzle is generally shaped like a duckbill type valve. However, it should be appreciated that nozzles or valves of other shapes and sizes may also be used. The variable nozzle 136 may also include a lip 152 configured to mount the variable nozzle 136 within the housing 102 between the first chamber 114 and the second chamber 118. The variable nozzle 136 may be constructed or molded of any material having a suitable flexibility, such as silicone, and preferably with a wall thickness of between 0.50 and 2.00 millimeters, and an orifice width between 0.25 to 1.00 millimeters, or smaller depending on manufacturing capabilities.

As previously described, the variable nozzle 136 is optional in the operation of the OPEP device 100. It should also be appreciated that the OPEP device 100 could alternatively omit both the chamber passage 116 and the variable nozzle 136, and thus comprise a single-chamber embodiment. Although functional without the variable nozzle 136, the performance of the OPEP device 100 over a wider range of exhalation flow rates is improved when the OPEP device 100 is operated with the variable nozzle 136. The chamber passage 116, when used without the variable nozzle 136, or the orifice 138 of the variable nozzle 136, when the variable nozzle 136 is included, serves to create a jet of exhaled air having an increased velocity. As explained in more detail below, the increased velocity of the exhaled air entering the second chamber 118 results in a proportional increase in the force applied by the exhaled air to the vane 132, and in turn, an increased torque about the shaft 134, all of which affect the ideal operating conditions.

Without the variable nozzle 136, the orifice between the first chamber 114 and the second chamber 118 is fixed according to the size, shape, and cross-sectional area of the chamber passage 116, which may be selectively adjusted by any suitable means, such as replacement of the middle section 103 or the rear section 105 of the housing. On the other hand, when the variable nozzle 136 is included in the OPEP device 100, the orifice between the first chamber 114 and the second chamber 118 is defined by the size, shape, and cross-sectional area of the orifice 138 of the variable nozzle 136, which may vary according to the flow rate of exhaled air and/or the pressure in the first chamber 114.

Turning to FIG. 14, a front perspective view of the variable nozzle 136 is shown with a flow of exhaled air therethrough. One aspect of the variable nozzle 136 shown in FIG. 14 is that, as the orifice 138 opens in response to the flow of exhaled air therethrough, the cross-sectional shape of the orifice 138 remains generally rectangular, which during the administration of OPEP therapy results in a lower drop in pressure through the variable nozzle 136 from the first chamber 114 (See FIGS. 3 and 5) to the second chamber 118. The generally consistent rectangular shape of the orifice 138 of the variable nozzle 136 during increased flow rates is achieved by the V-shaped slits 150 formed between the top and bottom walls 146 and the side walls 148, which serve to permit the side walls 148 to flex without restriction. Preferably, the V-shaped slits 150 are as thin as possible to minimize the leakage of exhaled air therethrough. For example, the V-shaped slits 150 may be approximately 0.25 millimeters wide, but depending on manufacturing capabilities, could range between 0.10 and 0.50 millimeters. Exhaled air that does leak through the V-shaped slits 150 is ultimately directed along the exhalation flow path by the guide walls 120 in the second chamber 118 protruding from the housing 102.

It should be appreciated that numerous factors contribute to the impact the variable nozzle 136 has on the performance of the OPEP device 100, including the geometry and material of the variable nozzle 136. By way of example only, in order to attain a target oscillating pressure frequency of between 10 to 13 Hz at an exhalation flow rate of 15 liters per minute, in one embodiment, a 1.0 by 20.0 millimeter passage or orifice may be utilized. However, as the exhalation flow rate increases, the frequency of the oscillating pressure in that embodiment also increases, though at a rate too quickly in comparison to the target frequency. In order to attain a target oscillating pressure frequency of between 18 to 20 Hz at an exhalation flow rate of 45 liters per minute, the same embodiment may utilize a 3.0 by 20.0 millimeter passage or orifice. Such a relationship demonstrates the desirability of a passage or orifice that expands in cross-sectional area as the exhalation flow rate increases in order to limit the drop in pressure across the variable nozzle 136.

Turning to FIGS. 15A-C, top phantom views of the OPEP device 100 show an exemplary illustration of the operation of the OPEP device 100. Specifically, FIG. 15A shows the restrictor member 130 in an initial, or closed position, where the flow of exhaled air through the chamber inlet 104 is restricted, and the vane 132 is in a first position, directing the flow of exhaled air toward the first chamber outlet 106. FIG. 15B shows this restrictor member 130 in a partially open position, where the flow of exhaled air through the chamber inlet 104 is less restricted, and the vane 132 is directly aligned with the jet of exhaled air exiting the variable nozzle 136. FIG. 15C shows the restrictor member 130 in an open position, where the flow of exhaled air through the chamber inlet 104 is even less restricted, and the vane 132 is in a second position, directing the flow of exhaled air toward the second chamber outlet 108. It should be appreciated that the cycle described below is merely exemplary of the operation of the OPEP device 100, and that numerous factors may affect operation of the OPEP device 100 in a manner that results in a deviation from the described cycle. However, during the operation of the OPEP device 100, the restrictor member 130 and the vane 132 will generally reciprocate between the positions shown in FIGS. 15A and 15C.

During the administration of OPEP therapy, the restrictor member 130 and the vane 132 may be initially positioned as shown in FIG. 15A. In this position, the restrictor member 130 is in a closed position, where the flow of exhaled air along the exhalation path through the chamber inlet 104 is substantially restricted. As such, an exhalation pressure at the chamber inlet 104 begins to increase when a user exhales into the mouthpiece 108. As the exhalation pressure at the chamber inlet 104 increases, a corresponding force acting on the face 140 of the restrictor member 130 increases. As previously explained, because the center 144 of the face 140 is offset from the plane defined by the radial offset and the shaft 134, a resulting net force creates a negative or opening torque about the shaft. In turn, the opening torque biases the restrictor member 130 to rotate open, letting exhaled air enter the first chamber 114, and biases the vane 132 away from its first position. As the restrictor member 130 opens and exhaled air is let into the first chamber 114, the pressure at the chamber inlet 104 begins to decrease, the force acting on the face 140 of the restrictor member begins to decrease, and the torque biasing the restrictor member 130 open begins to decrease.

As exhaled air continues to enter the first chamber 114 through the chamber inlet 104, it is directed along the exhalation flow path 110 by the housing 102 until it reaches the chamber passage 116 disposed between the first chamber 114 and the second chamber 118. If the OPEP device 100 is being operated without the variable nozzle 136, the exhaled air accelerates through the chamber passage 116 due to the decrease in cross-sectional area to form a jet of exhaled air. Likewise, if the OPEP device 100 is being operated with the variable nozzle 136, the exhaled air accelerates through the orifice 138 of the variable nozzle 136, where the pressure through the orifice 138 causes the side walls 148 of the variable nozzle 136 to flex outward, thereby increasing the size of the orifice 138, as well as the resulting flow of exhaled air thereth rough. To the extent some exhaled air leaks out of the V-shaped slits 150 of the variable nozzle 136, it is directed back toward the jet of exhaled air and along the exhalation flow path by the guide walls 120 protruding into the housing 102.

Then, as the exhaled air exits the first chamber 114 through the variable nozzle 136 and/or chamber passage 116 and enters the second chamber 118, it is directed by the vane 132 toward the front section 101 of the housing 102, where it is forced to reverse directions before exiting the OPEP device 100 through the open first chamber exit 106. As a result of the change in direction of the exhaled air toward the front section 101 of the housing 102, a pressure accumulates in the second chamber 118 near the front section 101 of the housing 102, thereby resulting in a force on the adjacent vane 132, and creating an additional negative or opening torque about the shaft 134. The combined opening torques created about the shaft 134 from the forces acting on the face 140 of the restrictor member 130 and the vane 132 cause the restrictor member 130 and the vane 132 to rotate about the shaft 134 from the position shown in FIG. 15A toward the position shown in FIG. 15B.

When the restrictor member 130 and the vane 132 rotate to the position shown in FIG. 15B, the vane 132 crosses the jet of exhaled air exiting the variable nozzle 136 or the chamber passage 116. Initially, the jet of exhaled air exiting the variable nozzle 136 or chamber passage 116 provides a force on the vane 132 that, along with the momentum of the vane 132, the shaft 134, and the restrictor member 130, propels the vane 132 and the restrictor member 130 to the position shown in FIG. 15C. However, around the position shown in FIG. 15B, the force acting on the vane 132 from the exhaled air exiting the variable nozzle 136 also switches from a negative or opening torque to a positive or closing torque. More specifically, as the exhaled air exits the first chamber 114 through the variable nozzle 136 and enters the second chamber 118, it is directed by the vane 132 toward the front section 101 of the housing 102, where it is forced to reverse directions before exiting the OPEP device 100 through the open second chamber exit 108. As a result of the change in direction of the exhaled air toward the front section 101 of the housing 102, a pressure accumulates in the second chamber 118 near the front section 101 of the housing 102, thereby resulting in a force on the adjacent vane 132, and creating a positive or closing torque about the shaft 134. As the vane 132 and the restrictor member 130 continue to move closer to the position shown in FIG. 15C, the pressure accumulating in the section chamber 118 near the front section 101 of the housing 102, and in turn, the positive or closing torque about the shaft 134, continues to increase, as the flow of exhaled air along the exhalation flow path 110 and through the chamber inlet 104 is even less restricted. Meanwhile, although the torque about the shaft 134 from the force acting on the restrictor member 130 also switches from a negative or opening torque to a positive or closing torque around the position shown in FIG. 15B, its magnitude is essentially negligible as the restrictor member 130 and the vane 132 rotate from the position shown in FIG. 15B to the position shown in FIG. 15C.

After reaching the position shown in FIG. 15C, and due to the increased positive or closing torque about the shaft 134, the vane 132 and the restrictor member 130 reverse directions and begin to rotate back toward the position shown in FIG. 15B. As the vane 132 and the restrictor member 130 approach the position shown in FIG. 15B, and the flow of exhaled through the chamber inlet 104 is increasingly restricted, the positive or closing torque about the shaft 134 begins to decrease. When the restrictor member 130 and the vane 132 reach the position 130 shown in FIG. 15B, the vane 132 crosses the jet of exhaled air exiting the variable nozzle 136 or the chamber passage 116, thereby creating a force on the vane 132 that, along with the momentum of the vane 132, the shaft 134, and the restrictor member 130, propels the vane 132 and the restrictor member 130 back to the position shown in FIG. 15A. After the restrictor member 130 and the vane 132 return to the position shown in FIG. 15A, the flow of exhaled air through the chamber inlet 104 is restricted, and the cycle described above repeats itself.

It should be appreciated that, during a single period of exhalation, the cycle described above will repeat numerous times. Thus, by repeatedly moving the restrictor member 130 between a closed position, where the flow of exhaled air through the chamber inlet 104 is restricted, and an open position, where the flow of exhaled air through the chamber inlet 104 is less restricted, an oscillating back pressure is transmitted to the user of the OPEP device 100 and OPEP therapy is administered.

Figure 17:
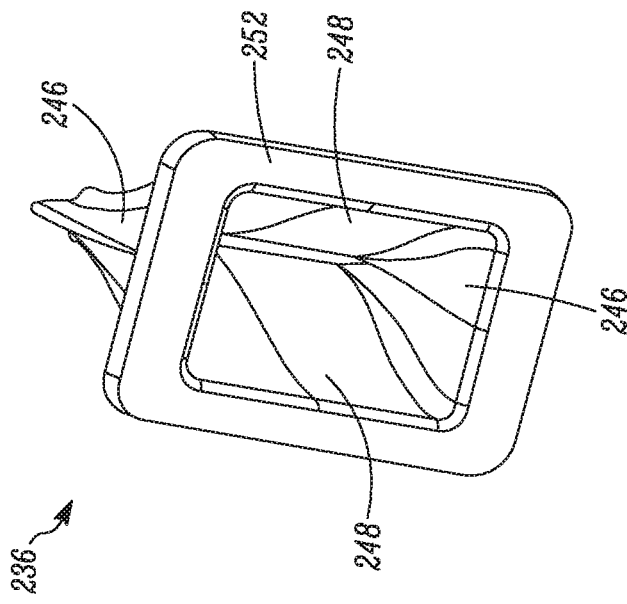
FIG. 17 is a rear perspective view of the variable nozzle of FIG. 16 shown without the flow of exhaled air therethrough.
Figure 16:
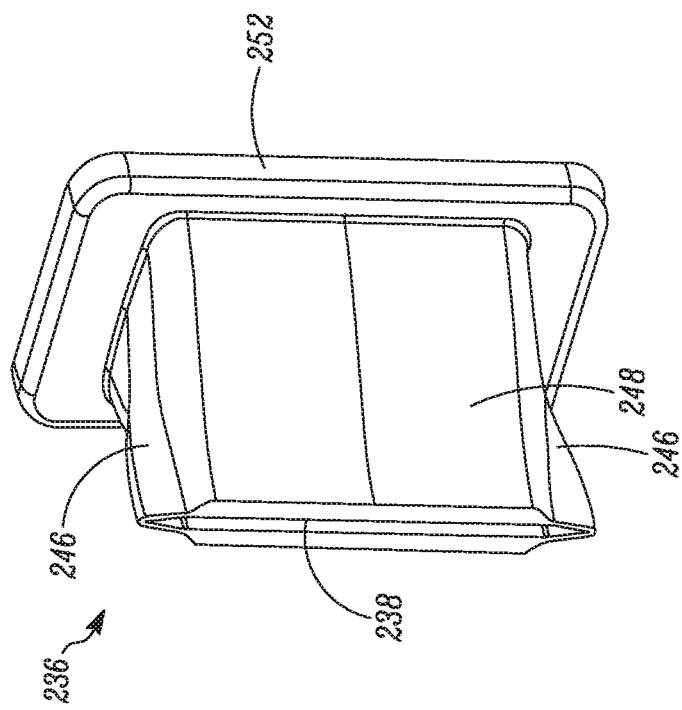
FIG. 16 is a front perspective view of a different embodiment of a variable nozzle shown without the flow of exhaled air therethrough.

Turning now to FIGS. 16-17, an alternative embodiment of a variable nozzle 236 is shown. The variable nozzle 236 may be used in the OPEP device 100 as an alternative to the variable nozzle 136 described above. As shown in FIGS. 16-17, the variable nozzle 236 includes an orifice 238, top and bottom walls 246, side walls 248, and a lip 252 configured to mount the variable nozzle 236 within the housing of the OPEP device 100 between the first chamber 114 and the second chamber 118 in the same manner as the variable nozzle 136. Similar to the variable nozzle 136 shown in FIGS. 12-13, the variable nozzle 236 may be constructed or molded of any material having a suitable flexibility, such as silicone.

During the administration of OPEP therapy, as the orifice 238 of the variable nozzle 236 opens in response to the flow of exhaled air therethrough, the cross-sectional shape of the orifice 238 remains generally rectangular, which results in a lower drop in pressure through the variable nozzle 236 from the first chamber 114 to the second chamber 118. The generally consistent rectangular shape of the orifice 238 of the variable nozzle 236 during increased flow rates is achieved by thin, creased walls formed in the top and bottom walls 246, which allow the side walls 248 to flex easier and with less resistance. A further advantage of this embodiment is that there is no leakage out of the top and bottom walls 246 while exhaled air flows through the orifice 238 of the variable nozzle 236, such as for example, through the V-shaped slits 150 of the variable nozzle 136 shown in FIGS. 12-13.

Those skilled in the art will also appreciate that, in some applications, only positive expiratory pressure (without oscillation) may be desired, in which case the OPEP device 100 may be operated without the restrictor member 130, but with a fixed orifice or manually adjustable orifice instead. The positive expiratory pressure embodiment may also comprise the variable nozzle 136, or the variable nozzle 236, in order to maintain a relatively consistent back pressure within a desired range.

Second OPEP Embodiment

Figure 18:
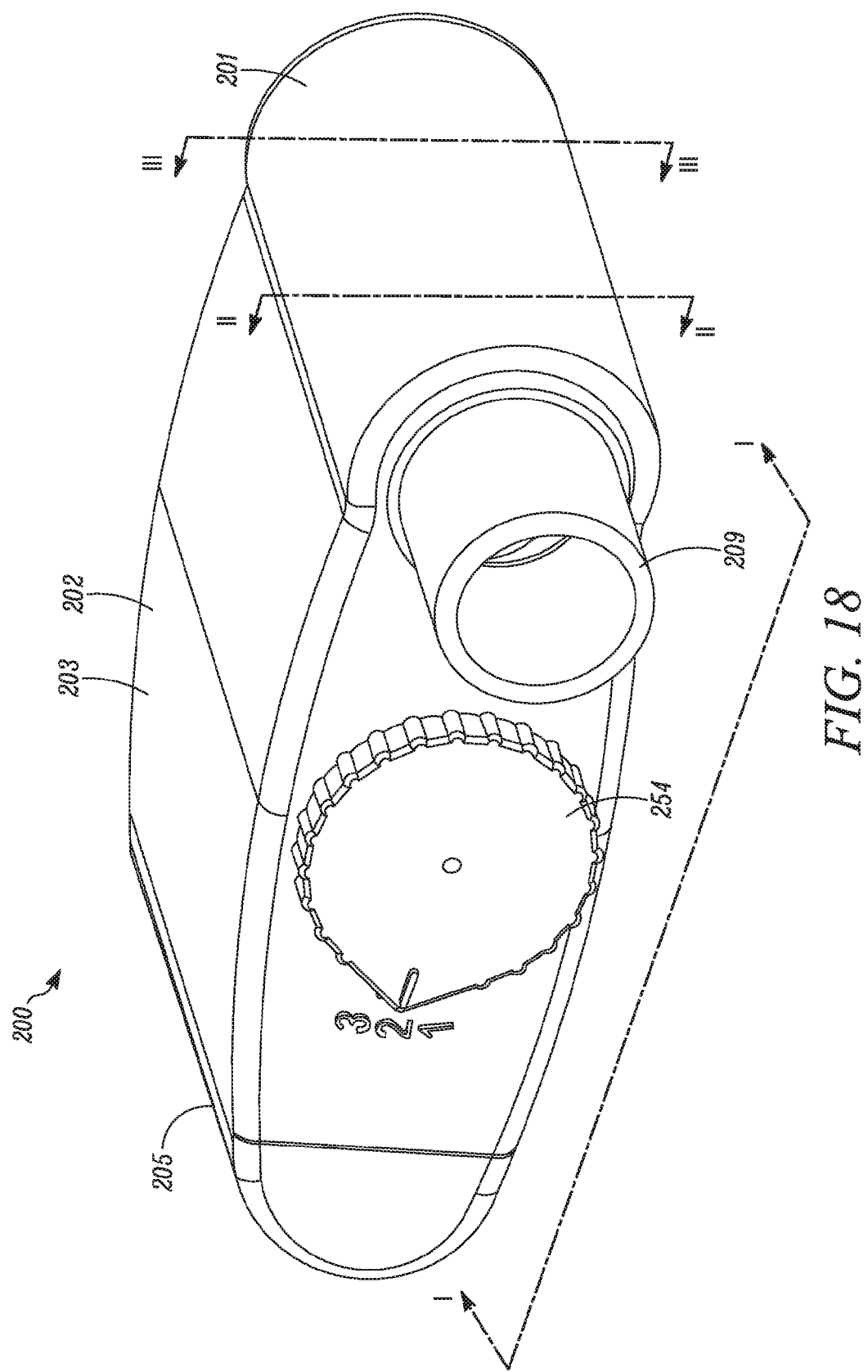
FIG. 18 is a front perspective view of a second embodiment of an OPEP device.
Figure 19:
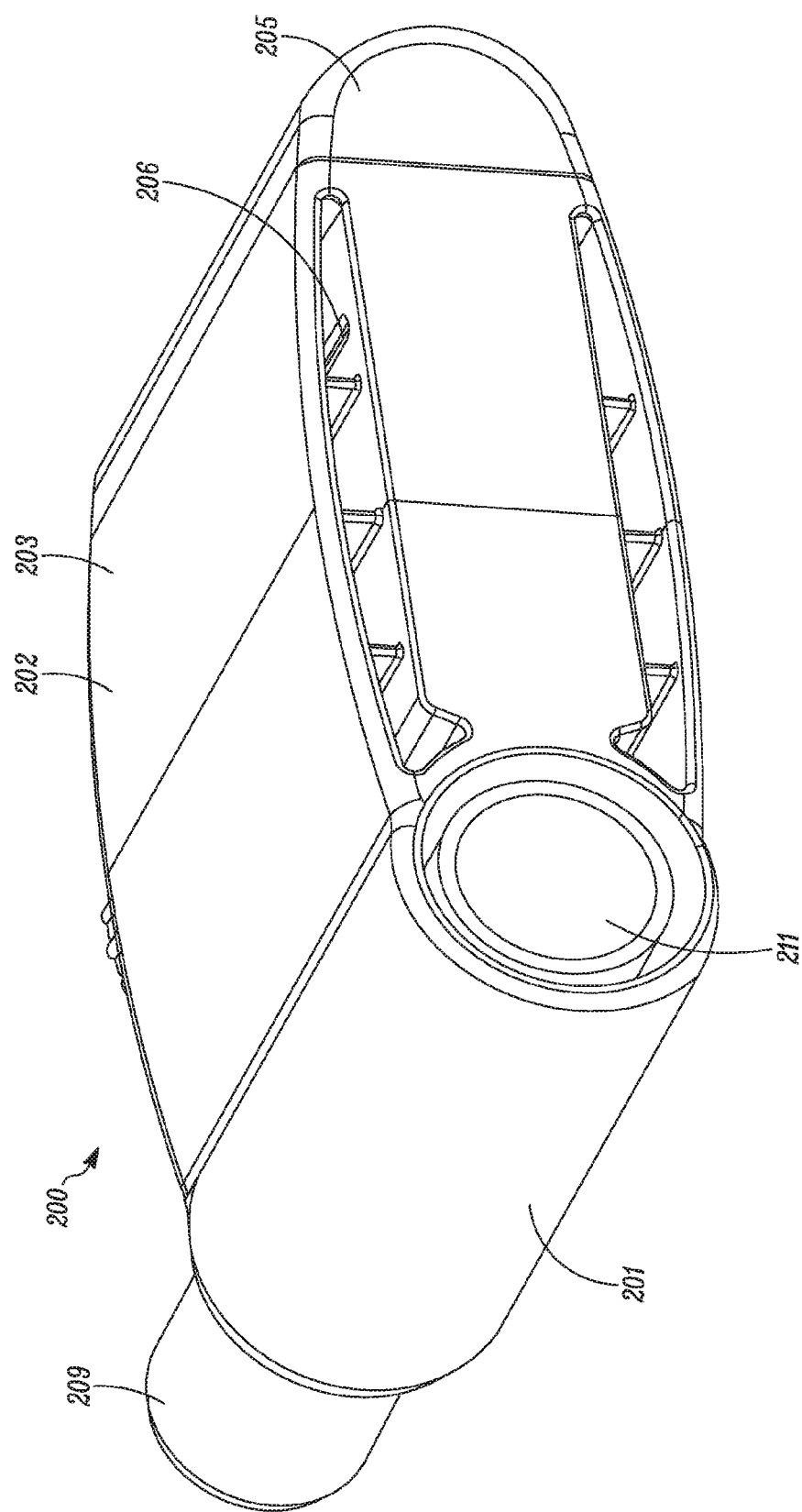
FIG. 19 is a rear perspective view of the OPEP device of FIG. 18.

Turning now to FIGS. 18-19, a front perspective view and a rear perspective view of a second embodiment of an OPEP device 200 is shown. The configuration and operation of the OPEP device 200 is similar to that of the OPEP device 100. However, as best shown in FIGS. 20-24, the OPEP device 200 further includes an adjustment mechanism 253 adapted to change the relative position of the chamber inlet 204 with respect to the housing 202 and the restrictor member 230, which in turn changes the range of rotation of the vane 232 operatively connected thereto. As explained below, a user is therefore able to conveniently adjust both the frequency and the amplitude of the OPEP therapy administered by the OPEP device 200 without opening the housing 202 and disassembling the components of the OPEP device 200.

The OPEP device 200 generally comprises a housing 202, a chamber inlet 204, a first chamber outlet 206 (best seen in FIGS. 23 and 32), a second chamber outlet 208 (best seen in FIGS. 23 and 32), and a mouthpiece 209 in fluid communication with the chamber inlet 204. As with the OPEP device 100, a front section 201, a middle section 203, and a rear section 205 of the housing 202 are separable so that the components contained therein can be periodically accessed, cleaned, replaced, or reconfigured, as required to maintain the ideal operating conditions. The OPEP device also includes an adjustment dial 254, as described below.

As discussed above in relation to the OPEP device 100, the OPEP device 200 may be adapted for use with other or additional interfaces, such as an aerosol delivery device. In this regard, the OPEP device 200 is equipped with an inhalation port 211 (best seen in FIGS. 19, 21, and 23) in fluid communication with the mouthpiece 209 and the chamber inlet 204. As noted above, the inhalation port may include a separate one-way valve (not shown) to permit a user of the OPEP device 200 both to inhale the surrounding air through the one-way valve and to exhale through the chamber inlet 204 without withdrawing the mouthpiece 209 of the OPEP device 200 between periods of inhalation and exhalation. In addition, the aforementioned aerosol delivery devices may be connected to the inhalation port 211 for the simultaneous administration of aerosol and OPEP therapies.

Figure 20:
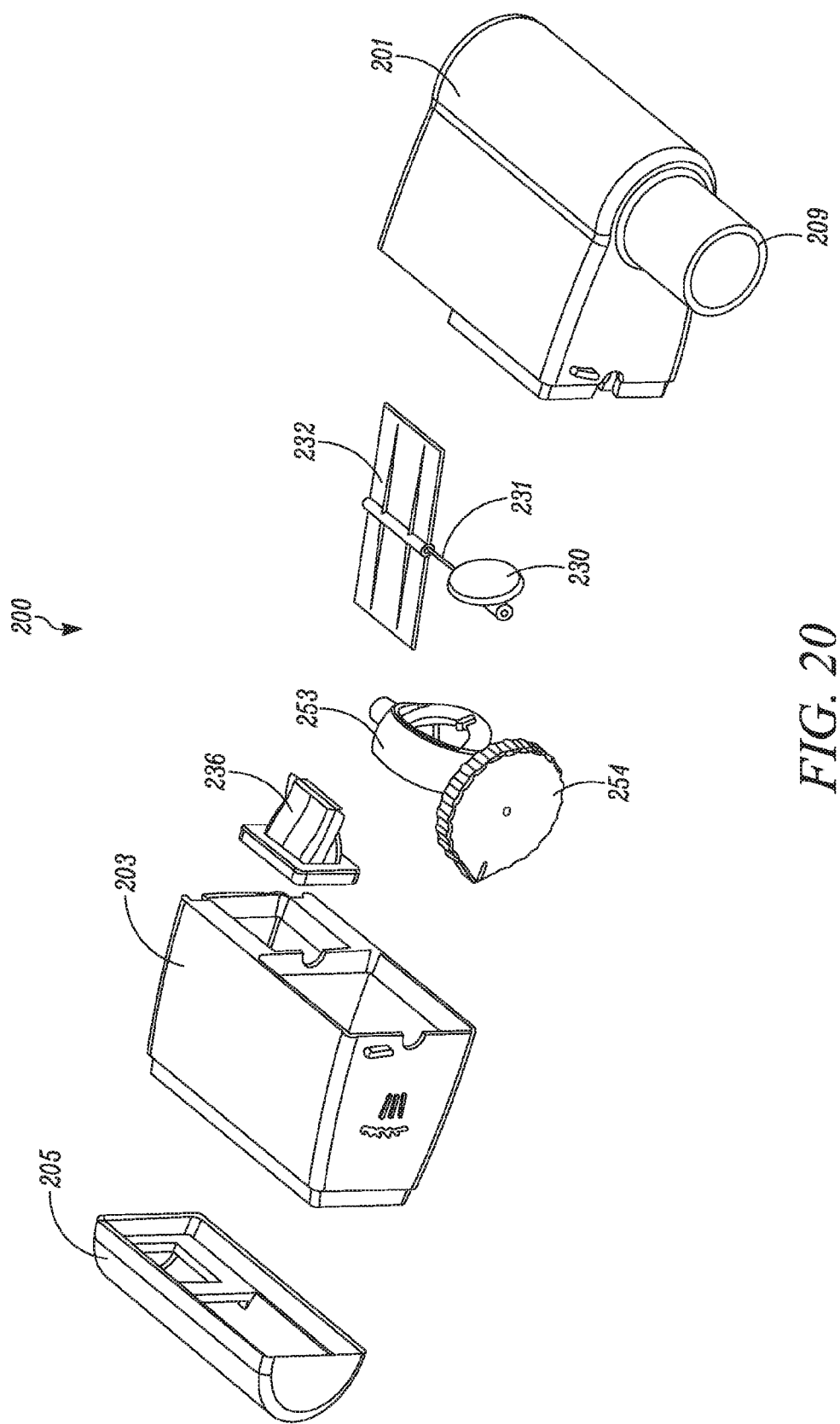
FIG. 20 is an exploded view of the OPEP device of FIG. 18, shown with the internal components of the OPEP device.

An exploded view of the OPEP device 200 is shown in FIG. 20. In addition to the components of the housing described above, the OPEP device 200 includes a restrictor member 230 operatively connected to a vane 232 by a pin 231, an adjustment mechanism 253, and a variable nozzle 236. As shown in the cross-sectional view of FIG. 21, when the OPEP device 200 is in use, the variable nozzle 236 is positioned between the middle section 203 and the rear section 205 of the housing 202, and the adjustment mechanism 253, the restrictor member 230, and the vane 232 form an assembly.

Figure 21:
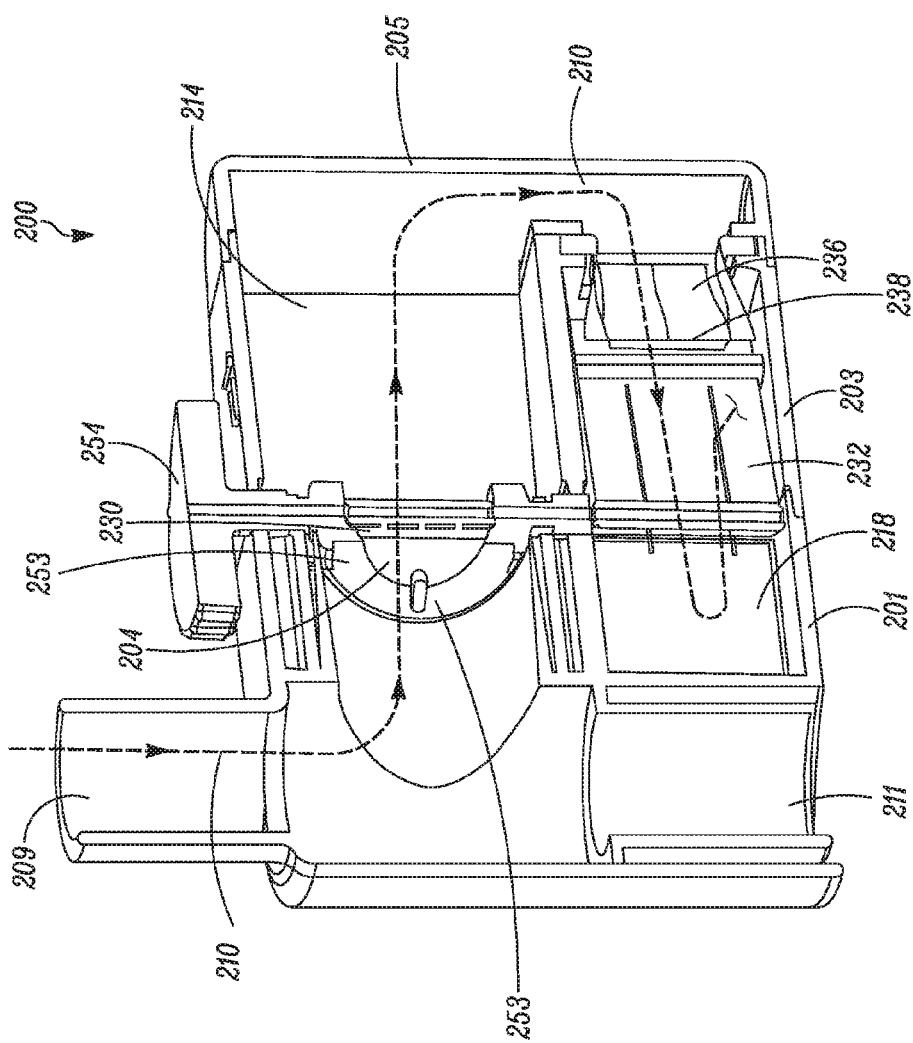
FIG. 21 is a cross-sectional view taken along line I in FIG. 18 of the OPEP device, shown with the internal components of the OPEP device.
Figure 22:
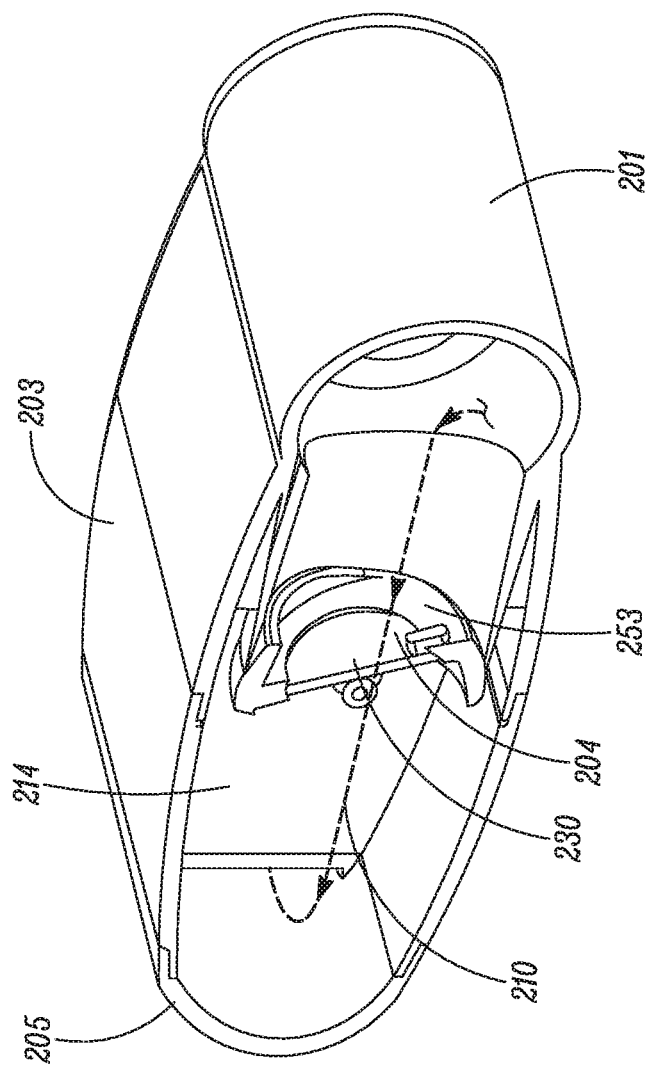
FIG. 22 is a cross-sectional view taken along line II in FIG. 18 of the OPEP device, shown with the internal components of the OPEP device.
Figure 23:
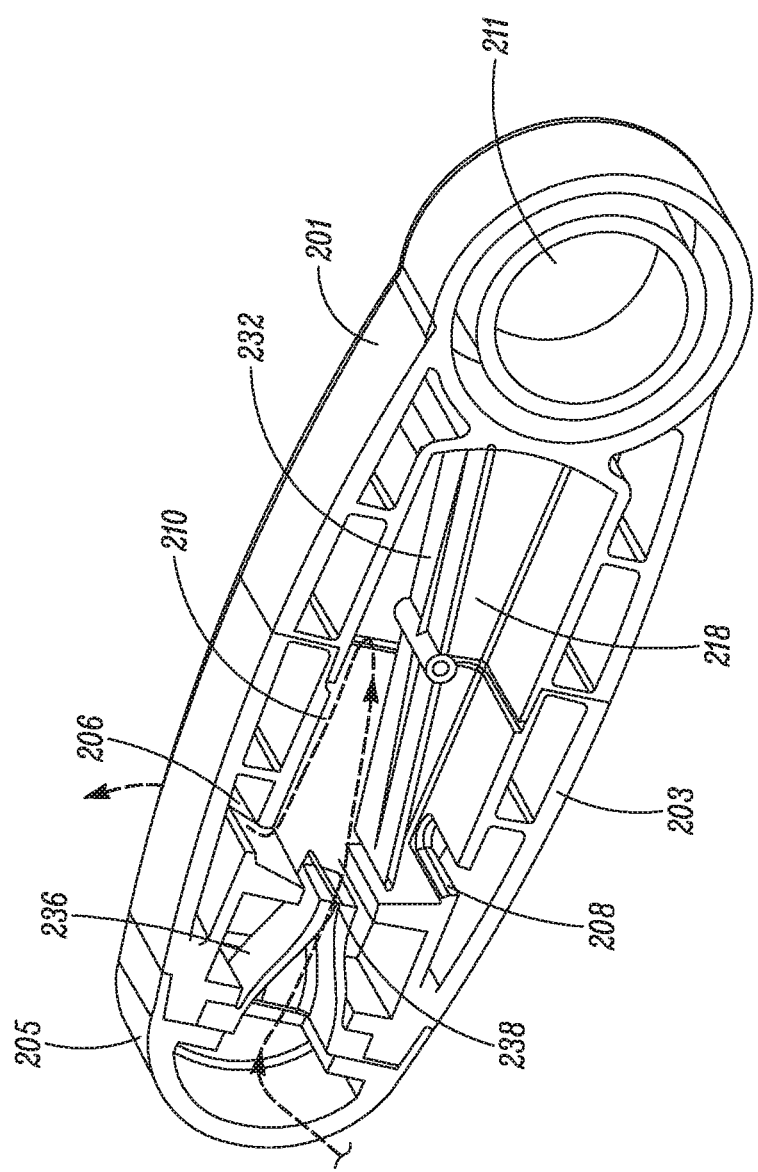
FIG. 23 is a cross-sectional view taken along line III in FIG. 18 of the OPEP device, shown with the internal components of the OPEP device.

Turning to FIGS. 21-23, various cross-sectional perspective views of the OPEP device 200 are shown. As with the OPEP device 100, an exhalation flow path 210, identified by a dashed line, is defined between the mouthpiece 209 and at least one of the first chamber outlet 206 and the second chamber outlet 208 (best seen in FIGS. 23 and 32). As a result of a one-way valve (not-shown) and/or an aerosol delivery device (not shown) attached to the inhalation port 211, the exhalation flow path 210 begins at the mouthpiece 209 and is directed toward the chamber inlet 204, which in operation may or may not be blocked by the restrictor member 230. After passing through the chamber inlet 204, the exhalation flow path 210 enters a first chamber 214 and makes a 180° turn toward the variable nozzle 236. After passing through the orifice 238 of the variable nozzle 236, the exhalation flow path 210 enters a second chamber 218. In the second chamber 218, the exhalation flow path 210 may exit the OPEP device 200 through at least one of the first chamber outlet 206 or the second chamber outlet 208. Those skilled in the art will appreciate that the exhalation flow path 210 identified by the dashed line is exemplary, and that air exhaled into the OPEP device 200 may flow in any number of directions or paths as it traverses from the mouthpiece 209 or chamber inlet 204 to the first chamber outlet 206 or the second chamber outlet 208.

Figure 25:
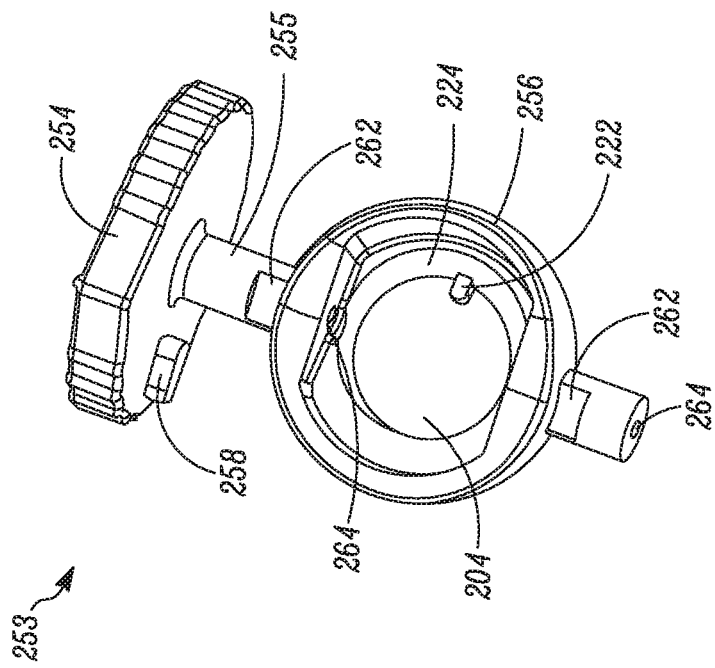
FIG. 25 is a rear perspective view of the adjustment mechanism of FIG. 24.
Figure 24:
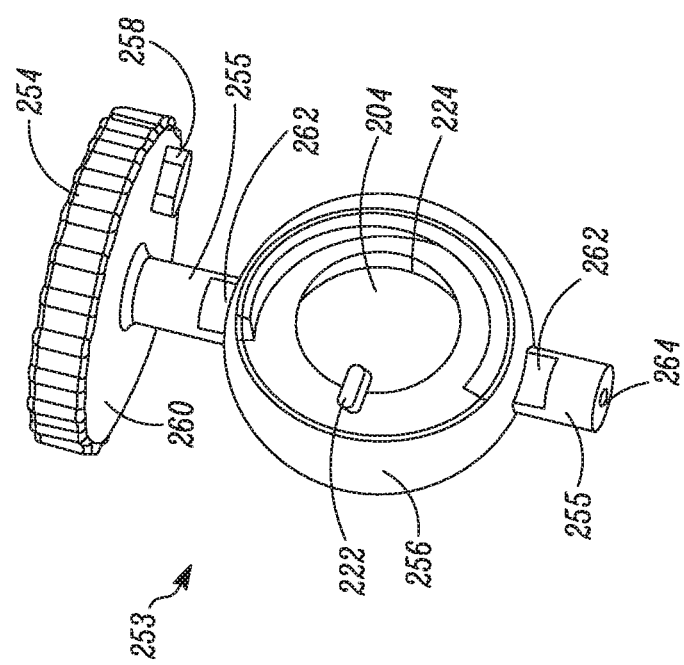
FIG. 24 is a front perspective view of an adjustment mechanism of the OPEP device of FIG. 18.

Referring to FIGS. 24-25, front and rear perspective views of the adjustment mechanism 253 of the OPEP device 200 are shown. In general, the adjustment mechanism 253 includes an adjustment dial 254, a shaft 255, and a frame 256. A protrusion 258 is positioned on a rear face 260 of the adjustment dial, and is adapted to limit the selective rotation of the adjustment mechanism 253 by a user, as further described below. The shaft 255 includes keyed portions 262 adapted to fit within upper and lower bearings 226, 228 formed in the housing 200 (see FIGS. 21 and 28-29). The shaft further includes an axial bore 264 configured to receive the pin 231 operatively connecting the restrictor member 230 and the vane 232. As shown, the frame 256 is spherical, and as explained below, is configured to rotate relative to the housing 202, while forming a seal between the housing 202 and the frame 256 sufficient to permit the administration of OPEP therapy. The frame 256 includes a circular opening defined by a seat 224 adapted to accommodate the restrictor member 230. In use, the circular opening functions as the chamber inlet 204. The frame 256 also includes a stop 222 for preventing the restrictor member 230 from opening in a wrong direction.

Figure 26:
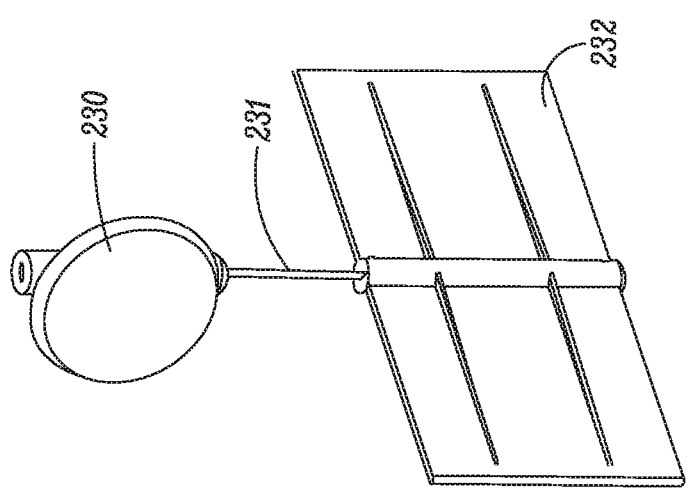
FIG. 26 is a front perspective view of a restrictor member operatively connected to a vane for use in the OPEP device of FIG. 18.

Turning to FIG. 26, a front perspective view of the restrictor member 230 and the vane 232 is shown. The design, materials, and configuration of the restrictor member 230 and the vane 232 may be the same as described above in regards to the OPEP device 100. However, the restrictor member 230 and the vane 232 in the OPEP device 200 are operatively connected by a pin 231 adapted for insertion through the axial bore 264 in the shaft 255 of the adjustment mechanism 253. The pin 231 may be constructed, for example, by stainless steel. In this way, rotation of the restrictor member 230 results in a corresponding rotation of the vane 232, and vice versa.

Figure 27:
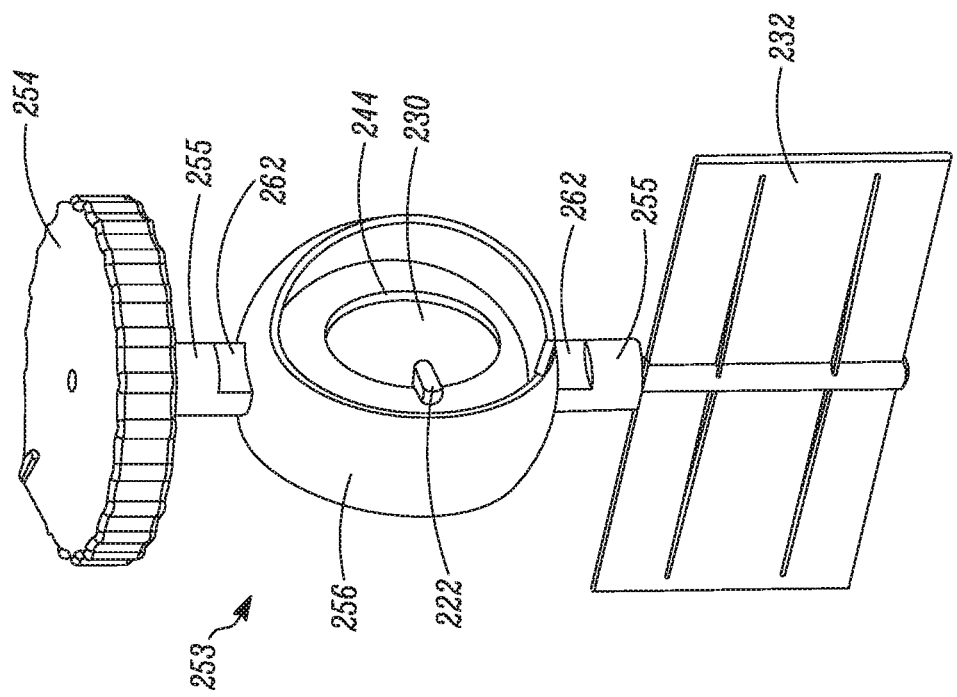
FIG. 27 is a front perspective view of the adjustment mechanism of FIG. 24 assembled with the restrictor member and the vane of FIG. 26.

Turning to FIG. 27, a front perspective view of the adjustment mechanism 253 assembled with the restrictor member 230 and the vane 232 is shown. In this configuration, it can be seen that the restrictor member 230 is positioned such that it is rotatable relative to the frame 256 and the seat 224 between a closed position (as shown), where a flow of exhaled air along the exhalation flow path 210 through the chamber inlet 204 is restricted, and an open position (not shown), where the flow of exhaled air through the chamber inlet 204 is less restricted. As previously mentioned the vane 232 is operatively connected to the restrictor member 230 by the pin 231 extending through shaft 255, and is adapted to move in unison with the restrictor member 230. It can further be seen that the restrictor member 230 and the vane 232 are supported by the adjustment mechanism 253, which itself is rotatable within the housing 202 of the OPEP device 200, as explained below.

Figure 29A:
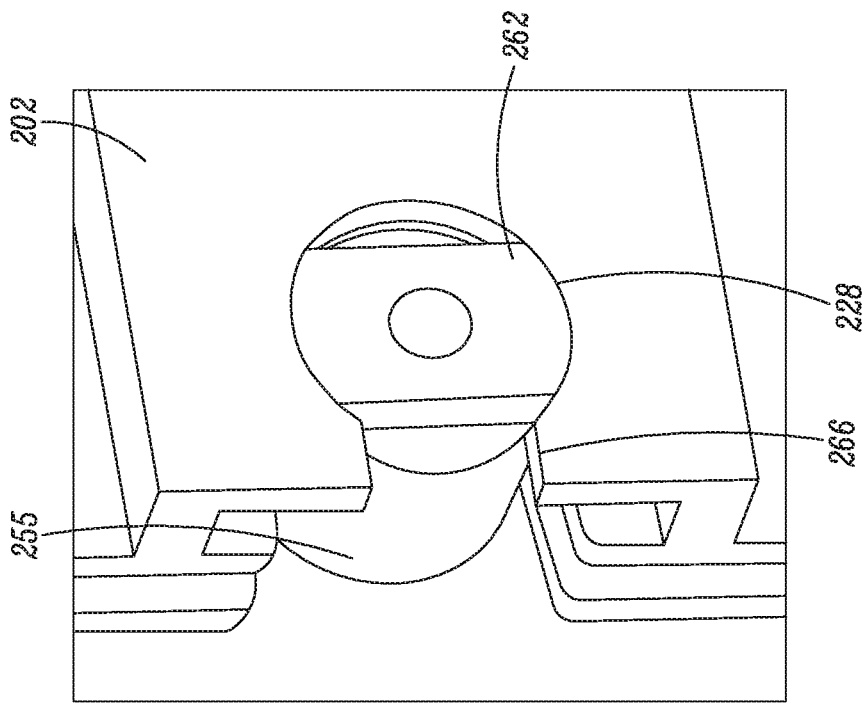
FIGS. 29A-B are partial cross-sectional views illustrating installation of the assembly of FIG. 27 within the OPEP device of FIG. 18.
Figure 29B:
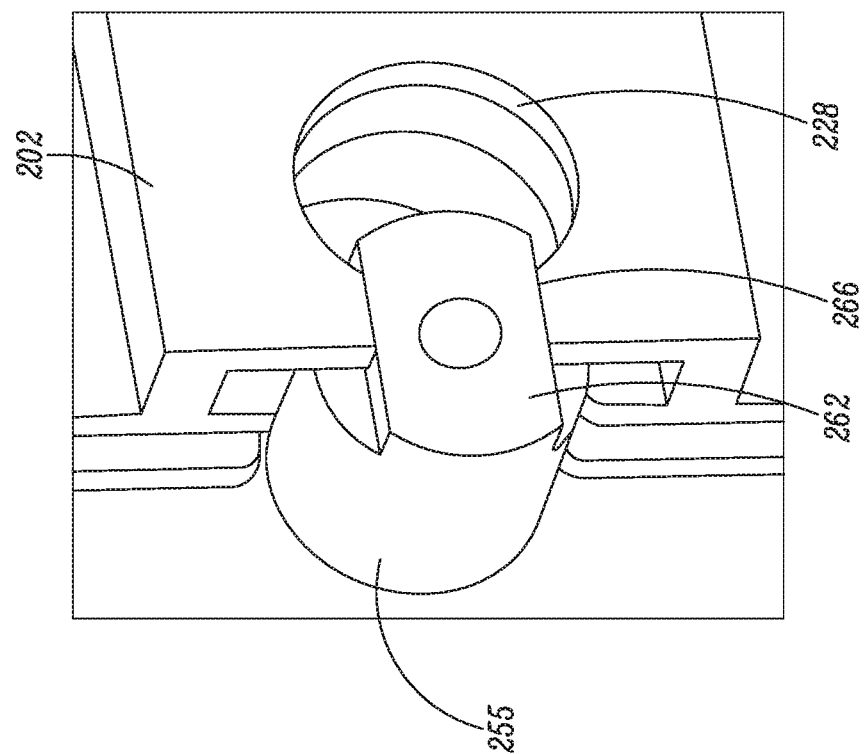

FIGS. 28 and 29A-B are partial cross-sectional views illustrating the adjustment mechanism 253 mounted within the housing 202 of the OPEP device 200. As shown in FIG. 28, the adjustment mechanism 253, as well as the restrictor member 230 and the vane 232, are rotatably mounted within the housing 200 about an upper and lower bearing 226, 228, such that a user is able to rotate the adjustment mechanism 253 using the adjustment dial 254. FIGS. 29A-29B further illustrates the process of mounting and locking the adjustment mechanism 253 within the lower bearing 228 of the housing 202. More specifically, the keyed portion 262 of the shaft 255 is aligned with and inserted through a rotational lock 166 formed in the housing 202, as shown in FIG. 29A. Once the keyed portion 262 of the shaft 255 is inserted through the rotational lock 266, the shaft 255 is rotated 90° to a locked position, but remains free to rotate. The adjustment mechanism 253 is mounted and locked within the upper bearing 226 in the same manner.

Figure 30:
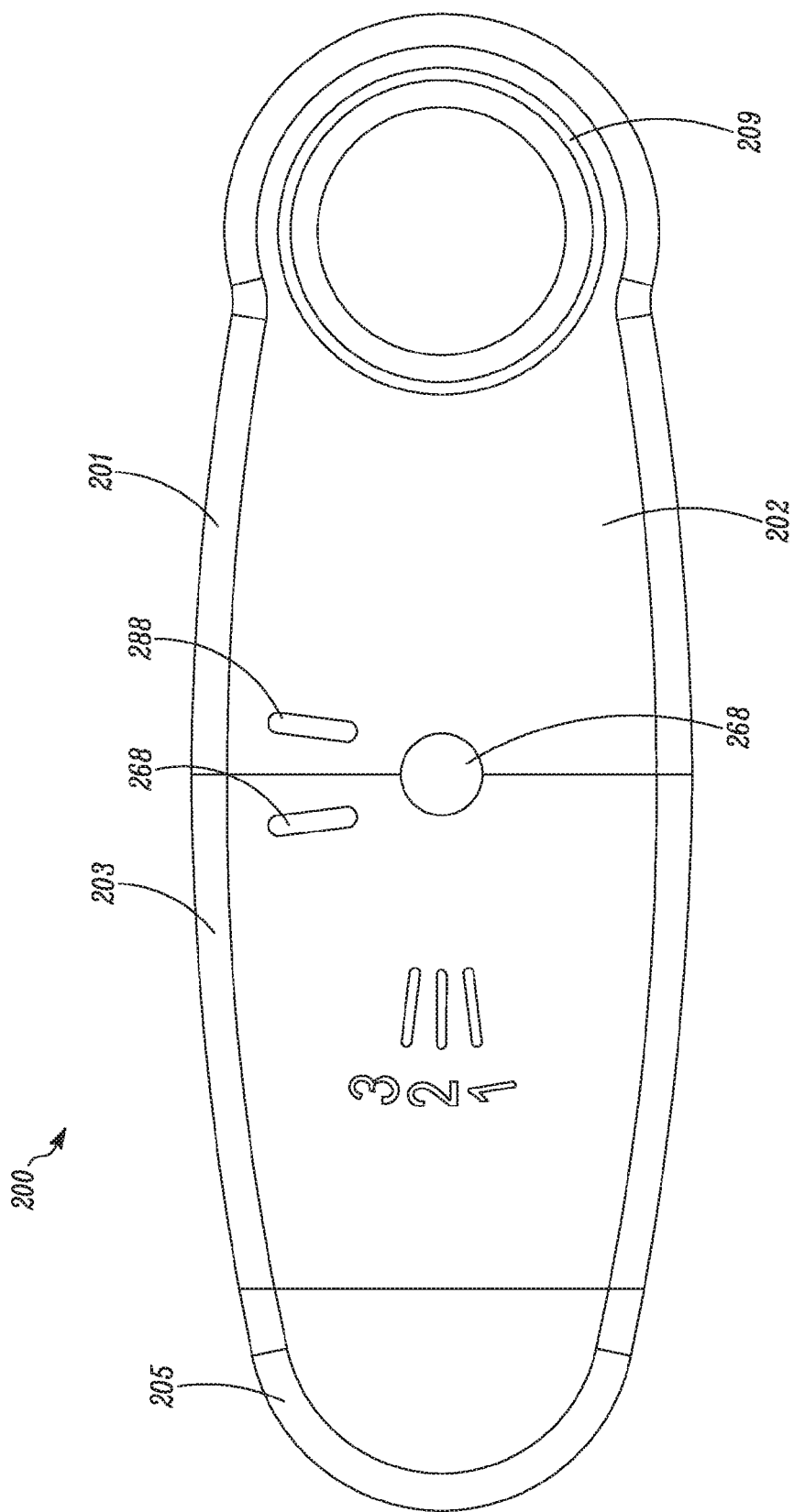
FIG. 30 is a front view of the OPEP device of FIG. 18 illustrating an aspect of the adjustability of the OPEP device.

Once the housing 200 and the internal components of the OPEP device 200 are assembled, the rotation of the shaft 255 is restricted to keep it within a locked position in the rotational lock 166. As shown in a front view of the OPEP device 200 in FIG. 30, two stops 268, 288 are positioned on the housing 202 such that they engage the protrusion 258 formed on the rear face 260 of the adjustment dial 254 when a user rotates the adjustment dial 254 to a predetermined position. For purposes of illustration, the OPEP device 200 is shown in FIG. 30 without the adjustment dial 254 or the adjustment mechanism 253, which would extend from the housing 202 through an opening 269. In this way, rotation of the adjustment dial 254, the adjustment mechanism 253, and the keyed portion 262 of the shaft 255 can be appropriately restricted.

Figure 31:
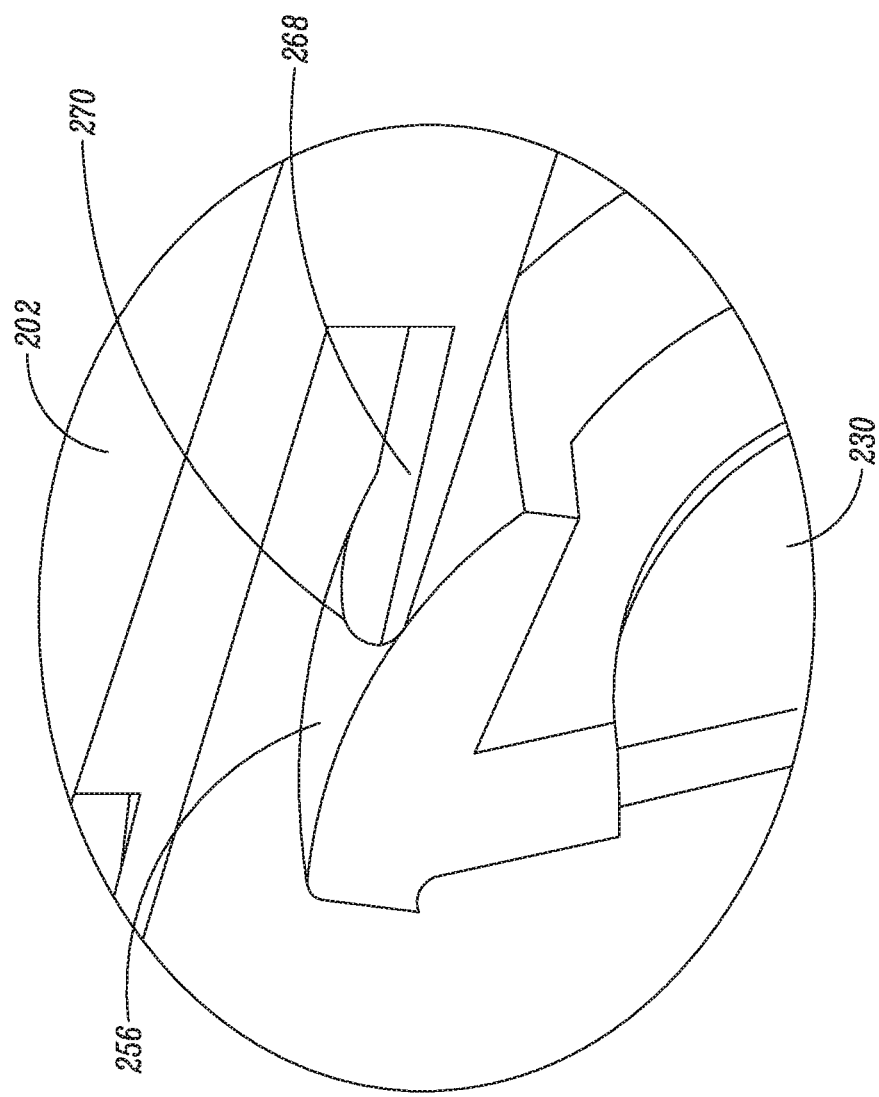
FIG. 31 is a partial cross-sectional view of the assembly of FIG. 27 within the OPEP device of FIG. 18.

Turning to FIG. 31, a partial cross-sectional view of the adjustment mechanism 253 mounted within the housing 200 is shown. As previously mentioned, the frame 256 of the adjustment mechanism 253 is spherical, and is configured to rotate relative to the housing 202, while forming a seal between the housing 202 and the frame 256 sufficient to permit the administration of OPEP therapy. As shown in FIG. 31, a flexible cylinder 271 extending from the housing 202 completely surrounds a portion of the frame 256 to form a sealing edge 270. Like the housing 202 and the restrictor member 230, the flexible cylinder 271 and the frame 256 may be constructed of a low shrink, low friction plastic. One such material is acetal. In this way, the sealing edge 270 contacts the frame 256 for a full 360° and forms a seal throughout the permissible rotation of the adjustment member 253.

Figure 33B:
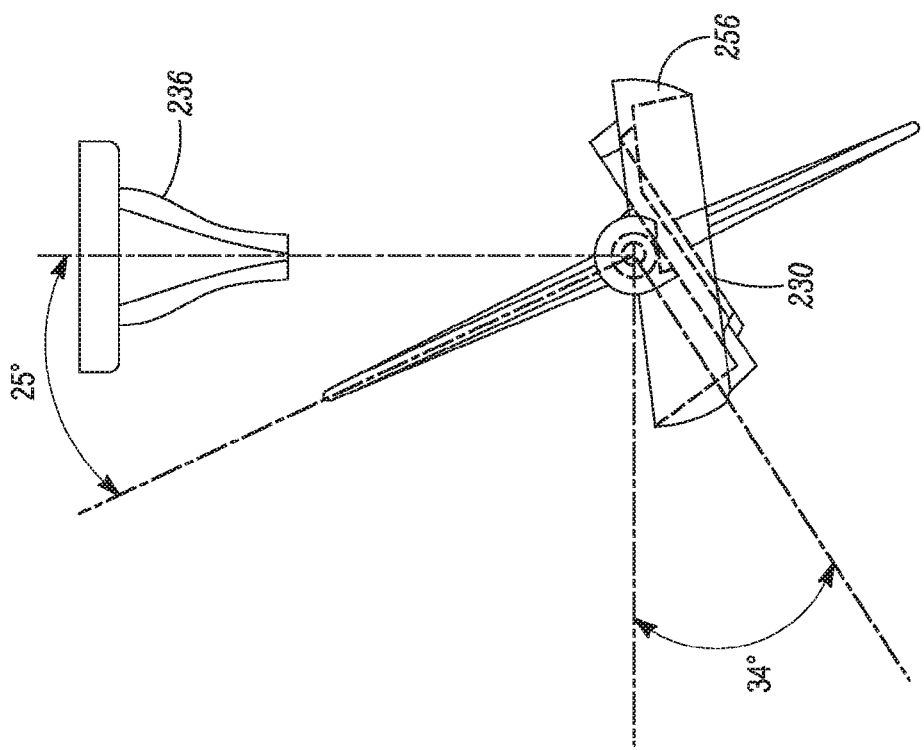
FIGS. 33A-B are top phantom views illustrating the adjustability of the OPEP device of FIG. 18.
Figure 33A:
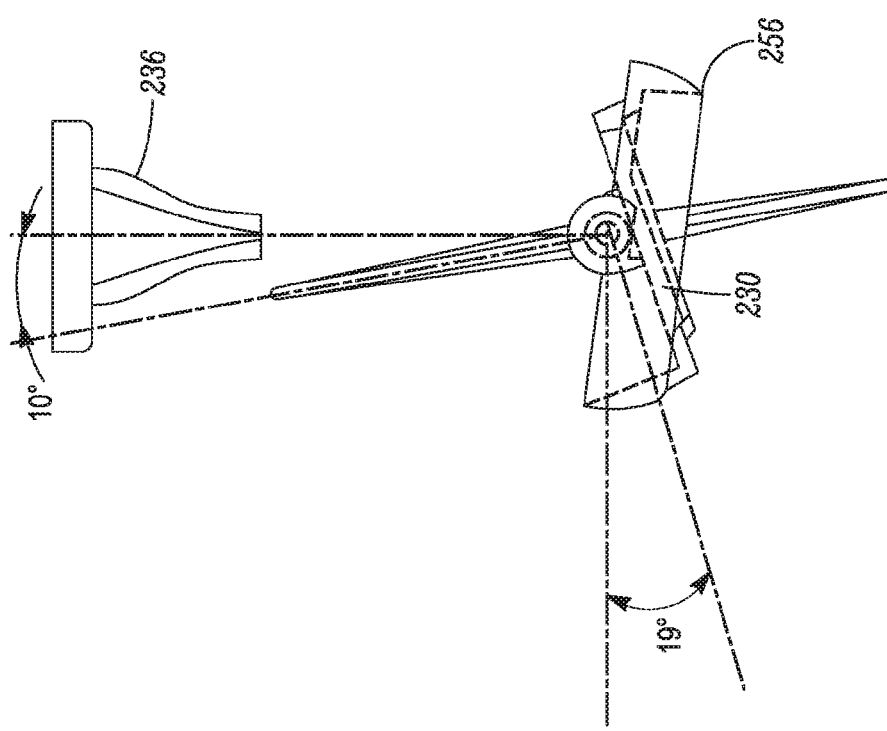

The selective adjustment of the OPEP device 200 will now be described with reference to FIGS. 32A-B, 33A-B, and 34A-B. FIGS. 32A-B are partial cross-sectional views of the OPEP device 200; FIGS. 33A-B are illustrations of the adjustability of the OPEP device 200; and, FIGS. 34A-B are top phantom views of the OPEP device 200. As previously mentioned with regards to the OPEP device 100, it is preferable that the vane 232 and the restrictor member 230 are configured such that when the OPEP device 200 is fully assembled, the angle between a centerline of the variable nozzle 236 and the vane 232 is between 10° and 25° when the restrictor member 230 is in a closed position. However, it should be appreciated that the adjustability of the OPEP device 200 is not limited to the parameters described herein, and that any number of configurations may be selected for purposes of administering OPEP therapy within the ideal operating conditions.

FIG. 32A shows the vane 232 at an angle of 10° from the centerline of the variable nozzle 236, whereas FIG. 32B shows the vane 232 at an angle of 25° from the centerline of the variable nozzle 236. FIG. 33A illustrates the necessary position of the frame 256 (shown in phantom) relative to the variable nozzle 236 such that the angle between a centerline of the variable nozzle 236 and the vane 232 is 10° when the restrictor member 230 is in the closed position. FIG. 33B, on the other hand, illustrates the necessary position of the frame 256 (shown in phantom) relative to the variable nozzle 236 such that the angle between a centerline of the variable nozzle 236 and the vane 232 is 25° when the restrictor member 230 is in the closed position.

Referring to FIGS. 34A-B, side phantom views of the OPEP device 200 are shown. The configuration shown in FIG. 34A corresponds to the illustrations shown in FIGS. 32A and 33A, wherein the angle between a centerline of the variable nozzle 236 and the vane 232 is 10° when the restrictor member 230 is in the closed position. FIG. 34B, on the other hand, corresponds to the illustrations shown in FIGS. 32B and 33B, wherein the angle between a centerline of the variable nozzle 236 and the vane 232 is 25° when the restrictor member 230 is in the closed position. In other words, the frame 256 of the adjustment member 253 has been rotated counter-clockwise 15°, from the position shown in FIG. 34A, to the position shown in FIG. 34B, thereby also increasing the permissible rotation of the vane 232.

In this way, a user is able to rotate the adjustment dial 254 to selectively adjust the orientation of the chamber inlet 204 relative to the restrictor member 230 and the housing 202. For example, a user may increase the frequency and amplitude of the OPEP therapy administered by the OPEP device 200 by rotating the adjustment dial 254, and therefore the frame 256, toward the position shown in FIG. 34A. Alternatively, a user may decrease the frequency and amplitude of the OPEP therapy administered by the OPEP device 200 by rotating the adjustment dial 254, and therefore the frame 256, toward the position shown in FIG. 34B. Furthermore, as shown for example in FIGS. 18 and 30, indicia may be provided to aid the user in the setting of the appropriate configuration of the OPEP device 200.

Operating conditions similar to those described below with reference to the OPEP device 800 may also be achievable for an OPEP device according to the OPEP device 200.

Third OPEP Embodiment

Figure 36:
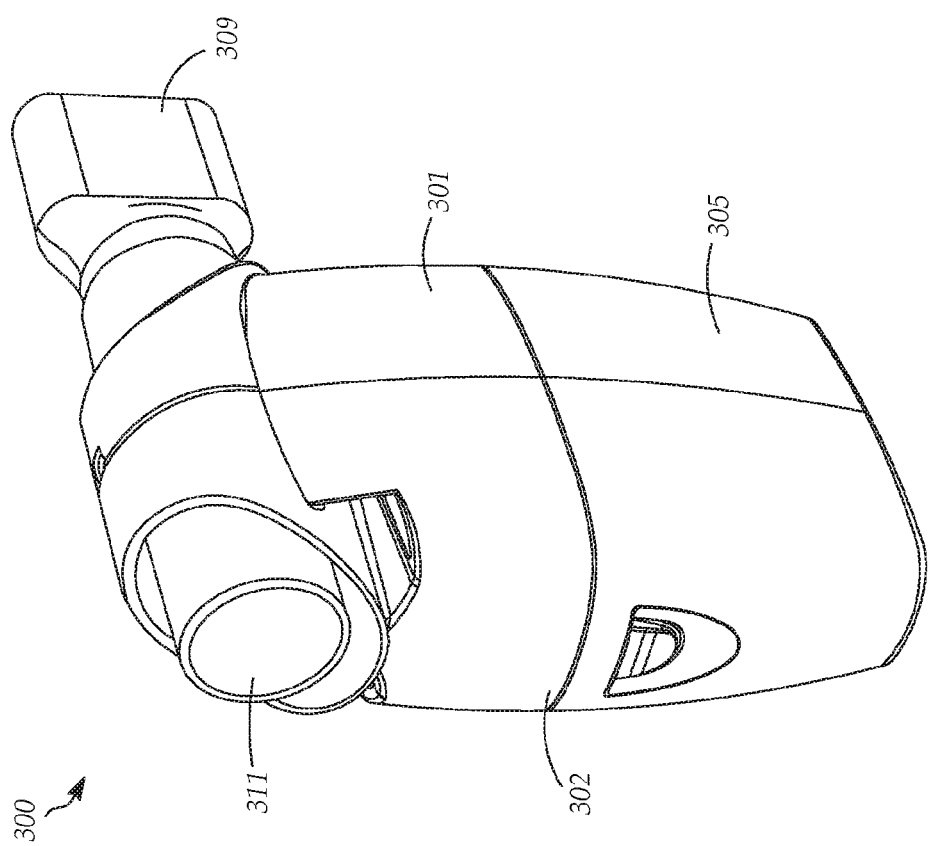
FIG. 36 is a rear perspective view of the OPEP device of FIG. 35.
Figure 37:
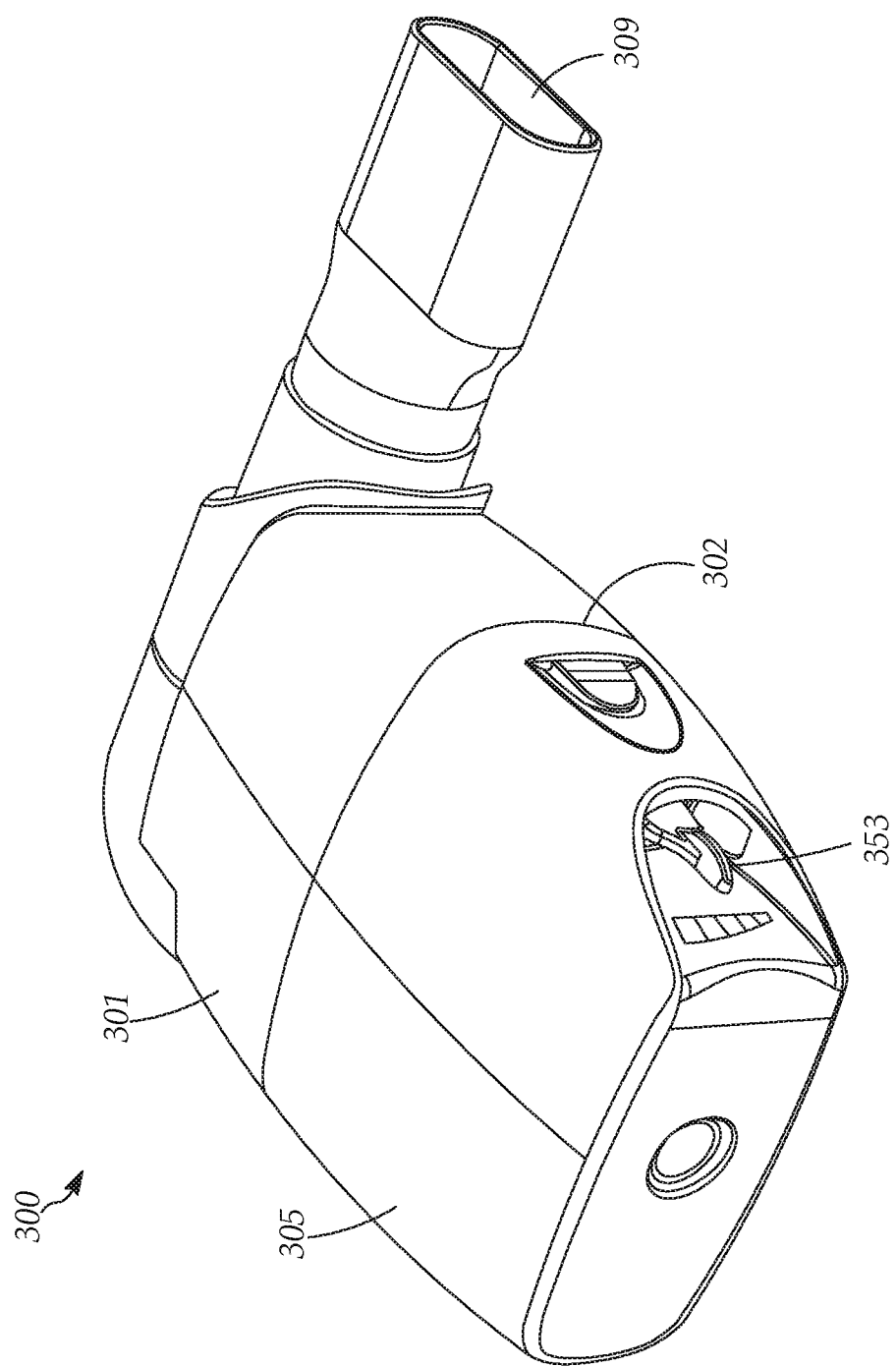
FIG. 37 is a perspective view of the bottom of the OPEP device of FIG. 35.

Turning to FIGS. 35-37, another embodiment of an OPEP device 300 is shown. The OPEP device 300 is similar to that of the OPEP device 200 in that is selectively adjustable. As best seen in FIGS. 35, 37, 40, and 49, the OPEP device 300, like the OPEP device 300, includes an adjustment mechanism 353 adapted to change the relative position of a chamber inlet 304 with respect to a housing 302 and a restrictor member 330, which in turn changes the range of rotation of a vane 332 operatively connected thereto. As previously explained with regards to the OPEP device 200, a user is therefore able to conveniently adjust both the frequency and the amplitude of the OPEP therapy administered by the OPEP device 300 without opening the housing 302 and disassembling the components of the OPEP device 300. The administration of OPEP therapy using the OPEP device 300 is otherwise the same as described above with regards to the OPEP device 100.

The OPEP device 300 comprises a housing 302 having a front section 301, a rear section 305, and an inner casing 303. As with the previously described OPEP devices, the front section 301, the rear section 305, and the inner casing 303 are separable so that the components contained therein can be periodically accessed, cleaned, replaced, or reconfigured, as required to maintain the ideal operating conditions. For example, as shown in FIGS. 35-37, the front section 301 and the rear section 305 of the housing 302 are removably connected via a snap fit engagement.

Figure 38:
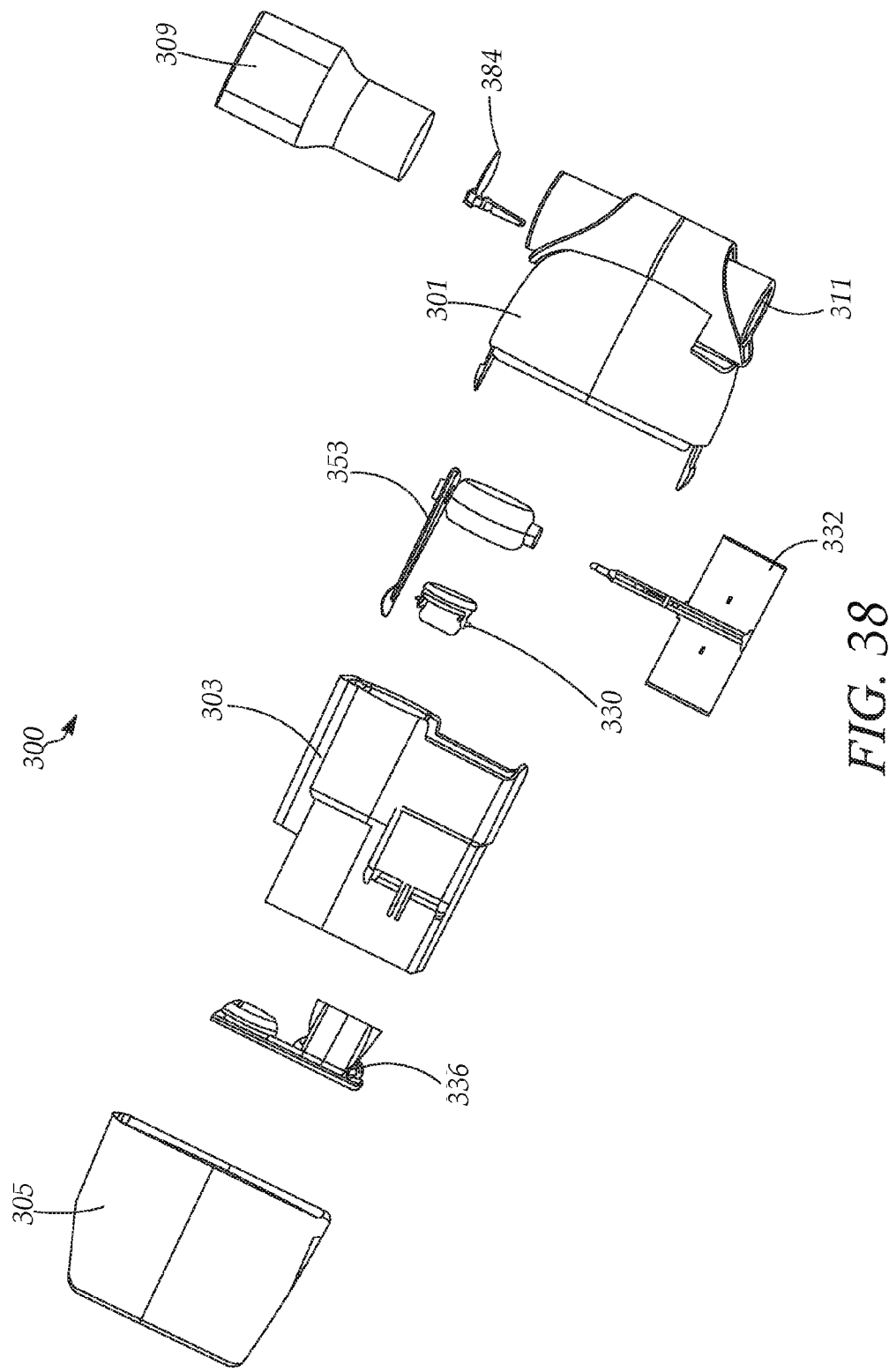
FIG. 38 is an exploded view of the OPEP device of FIG. 35.

The components of the OPEP device 300 are further illustrated in the exploded view of FIG. 38. In general, in addition to the front section 301, the rear section 305, and the inner casing 303, the OPEP device 300 further comprises a mouthpiece 309, an inhalation port 311, a one-way valve 384 disposed therebetween, an adjustment mechanism 353, a restrictor member 330, a vane 332, and a variable nozzle 336.

Figure 39:
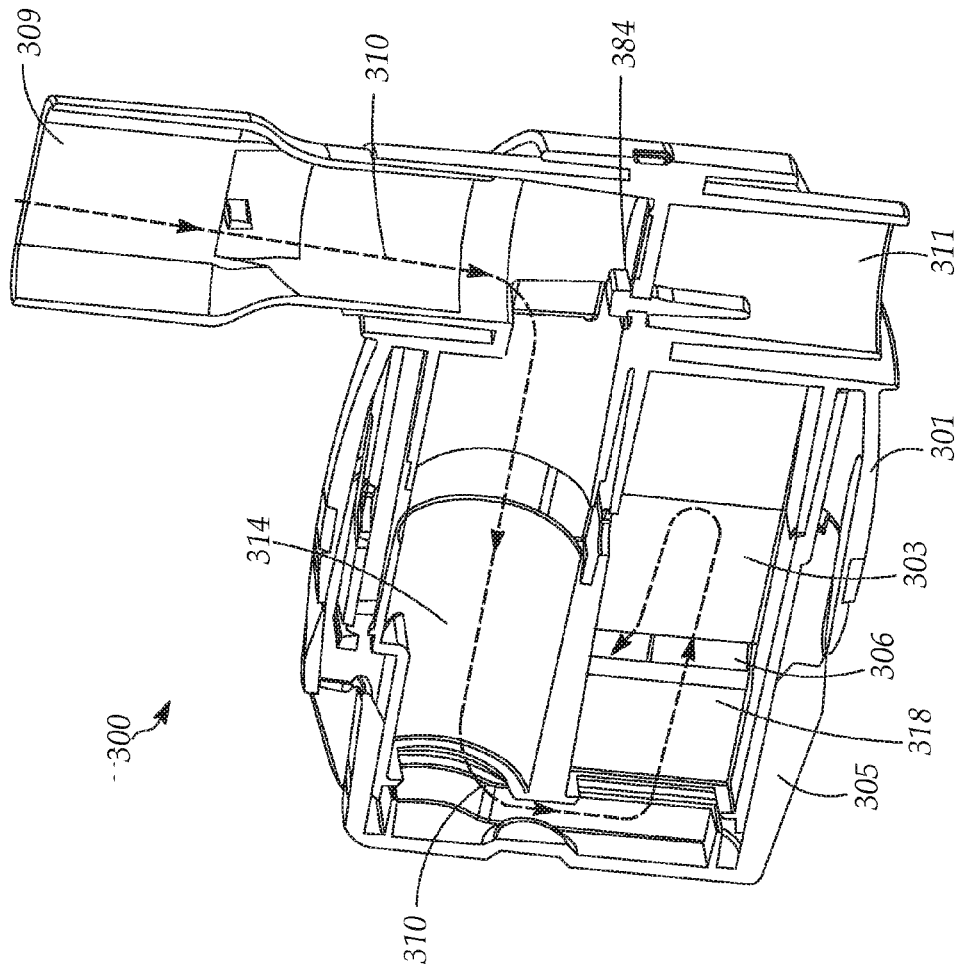
FIG. 39 is a cross-sectional view taken along line I in FIG. 35, shown without the internal components of the OPEP device.
Figure 40:
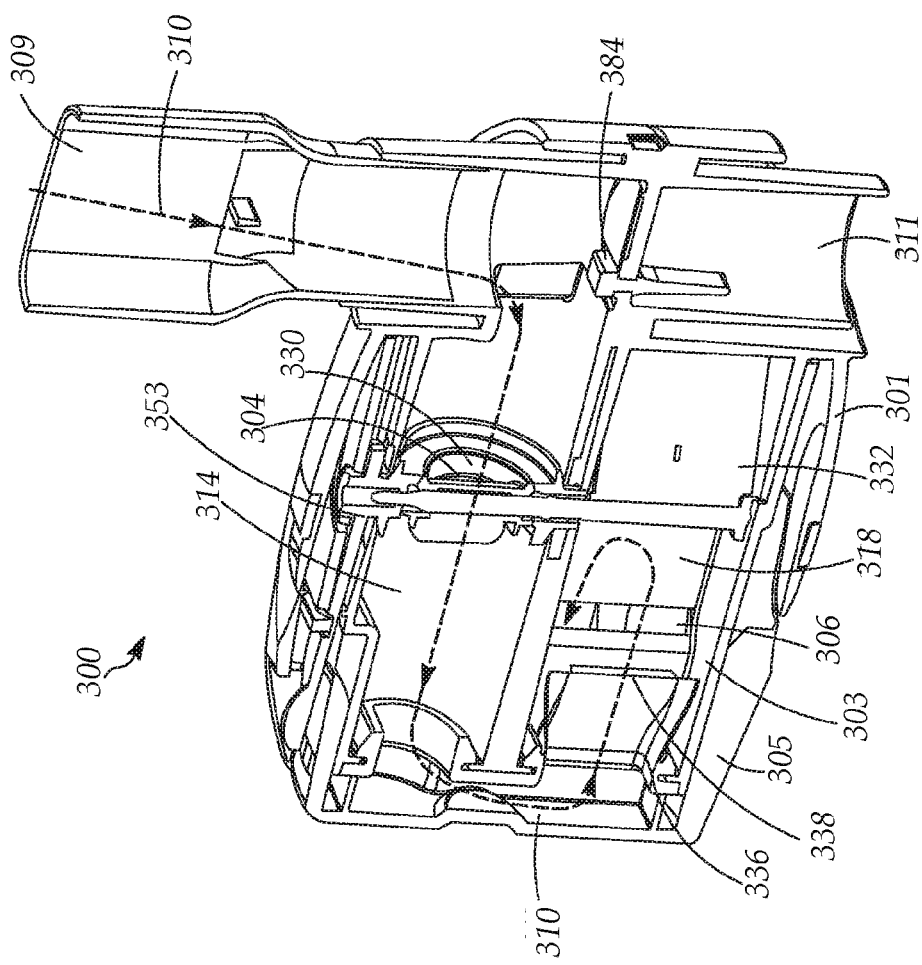
FIG. 40 is a cross-sectional view taken along line I in FIG. 35, shown with the internal components of the OPEP device.
Figure 41:
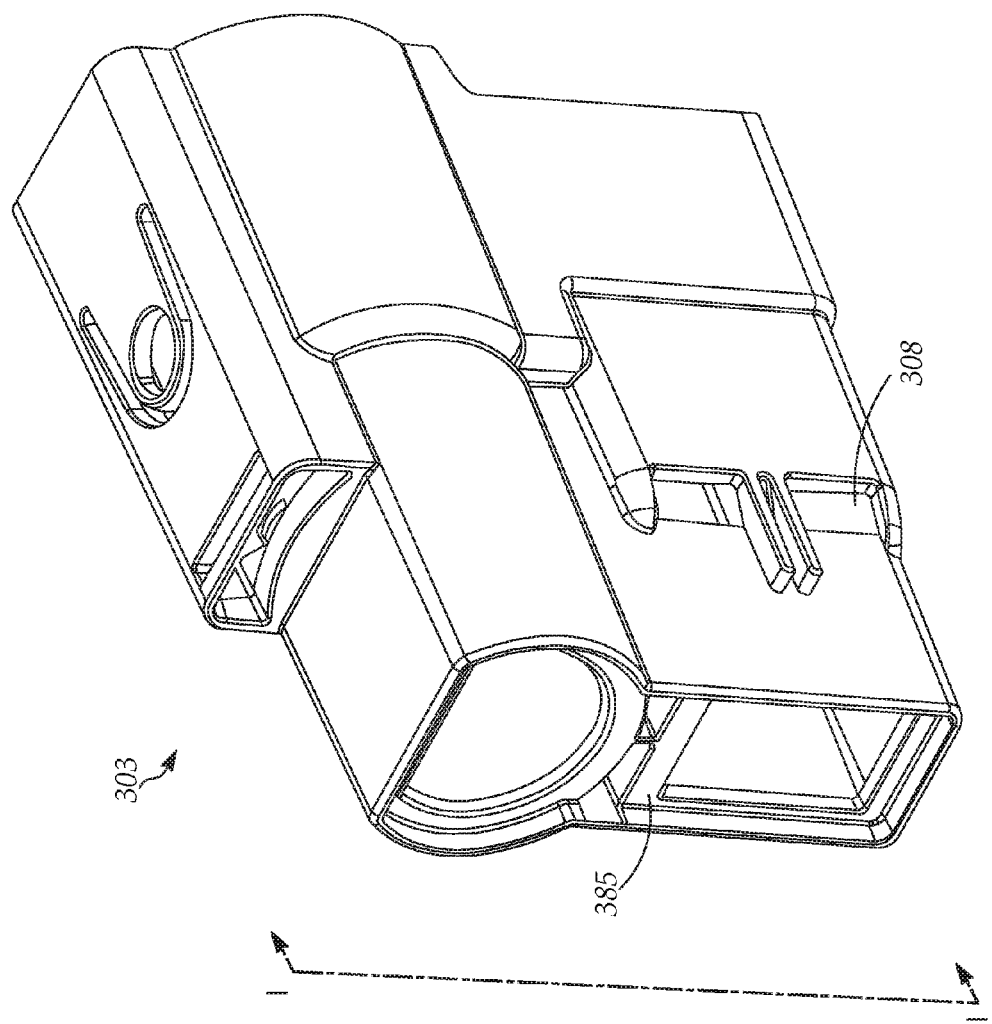
FIG. 41 is a front-perspective view of an inner casing of the OPEP device of FIG. 35.
Figure 42:
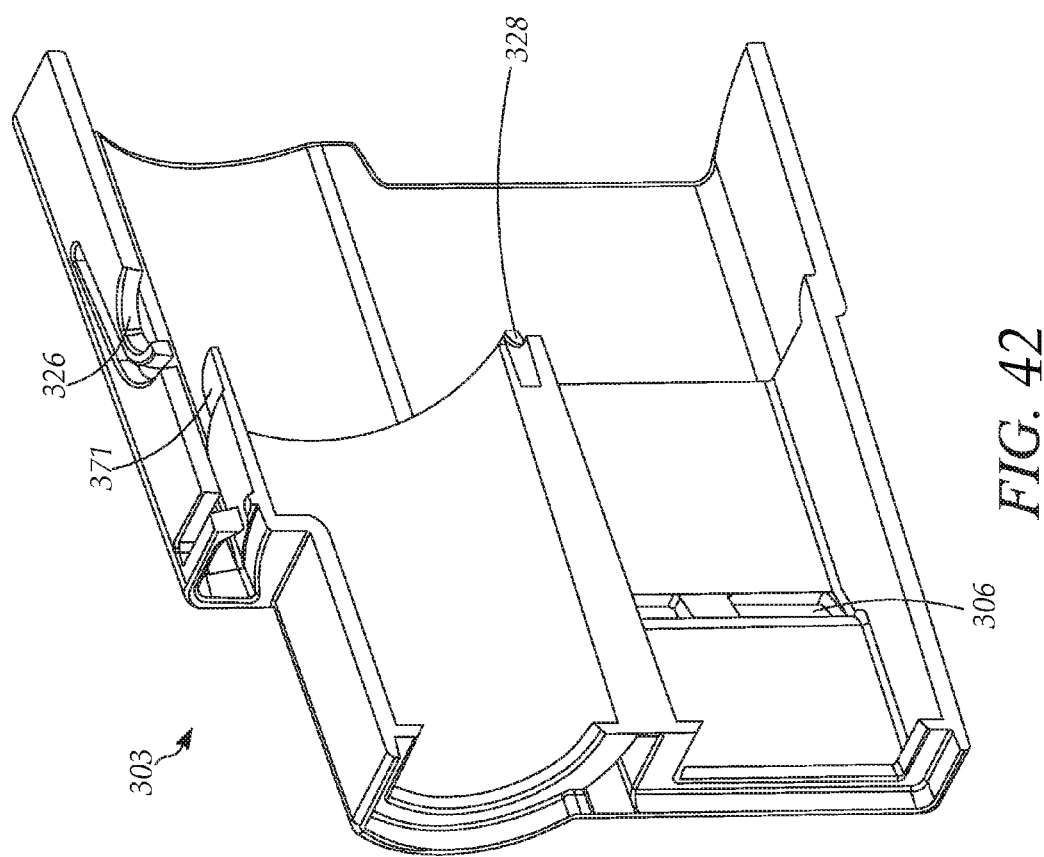
FIG. 42 is a cross-sectional view of the inner casing taken along line I of in FIG. 41.

As seen in FIGS. 39-40, the inner casing 303 is configured to fit within the housing 302 between the front section 301 and the rear section 305, and partially defines a first chamber 314 and a second chamber 318. The inner casing 303 is shown in further detail in the perspective and cross sectional views shown in FIGS. 41-42. A first chamber outlet 306 and a second chamber outlet 308 are formed within the inner casing 303. One end 385 of the inner casing 303 is adapted to receive the variable nozzle 336 and maintain the variable nozzle 336 between the rear section 305 and the inner casing 303. An upper bearing 326 and a lower bearing 328 for supporting the adjustment mechanism 353 is formed, at least in part, within the inner casing 303. Like the flexible cylinder 271 and sealing edge 270 described above with regards to the OPEP device 200, the inner casing 303 also includes a flexible cylinder 371 with a sealing edge 370 for engagement about a frame 356 of the adjustment mechanism 353.

Figure 43:
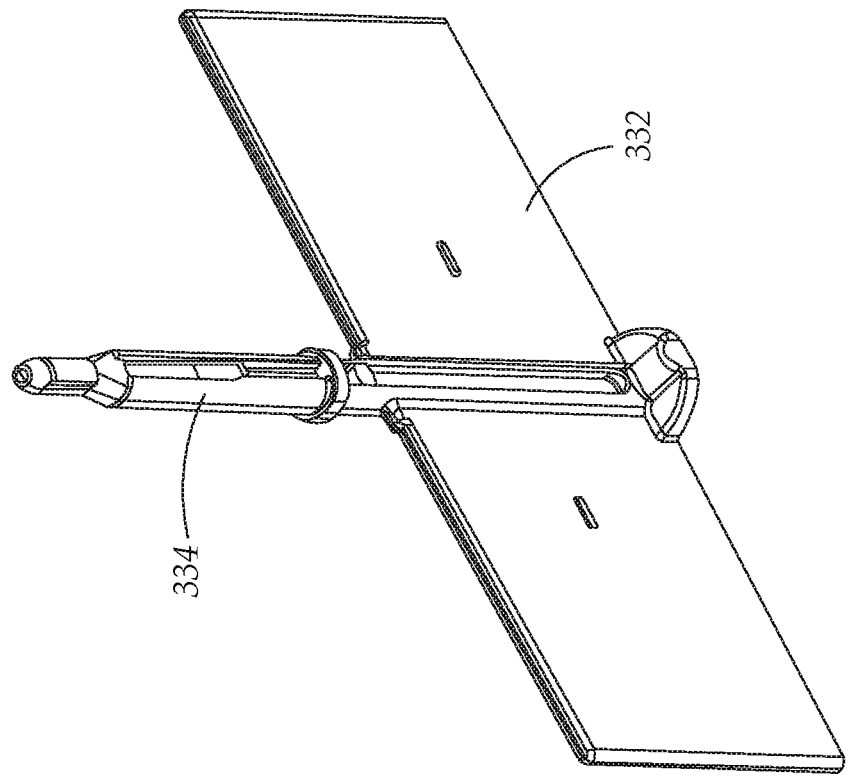
FIG. 43 is a perspective view of a vane of the OPEP device of FIG. 35.

The vane 332 is shown in further detail in the perspective view shown in FIG. 43. A shaft 334 extends from the vane 332 and is keyed to engage a corresponding keyed portion within a bore 365 of the restrictor member 330. In this way, the shaft 334 operatively connects the vane 332 with the restrictor member 330 such that the vane 332 and the restrictor member 330 rotate in unison.

Figure 44:
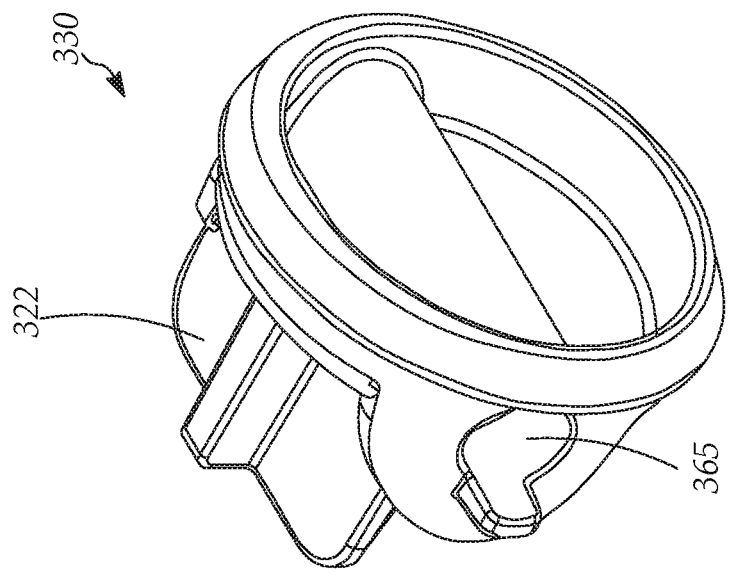
FIG. 44 is a front perspective view of a restrictor member of the OPEP device of FIG. 35.
Figure 46:
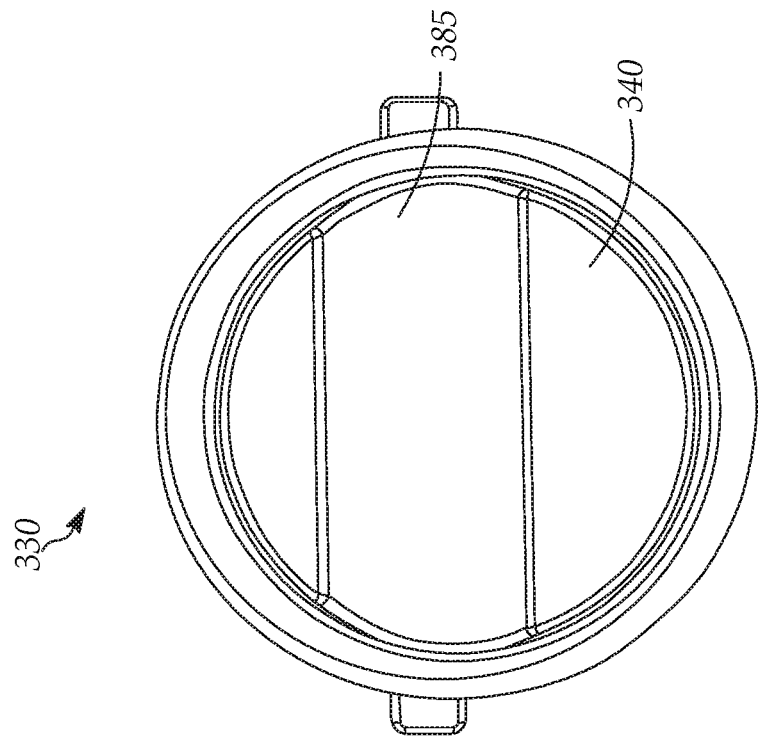
FIG. 46 is a front view of the restrictor member of FIG. 44.
Figure 45:
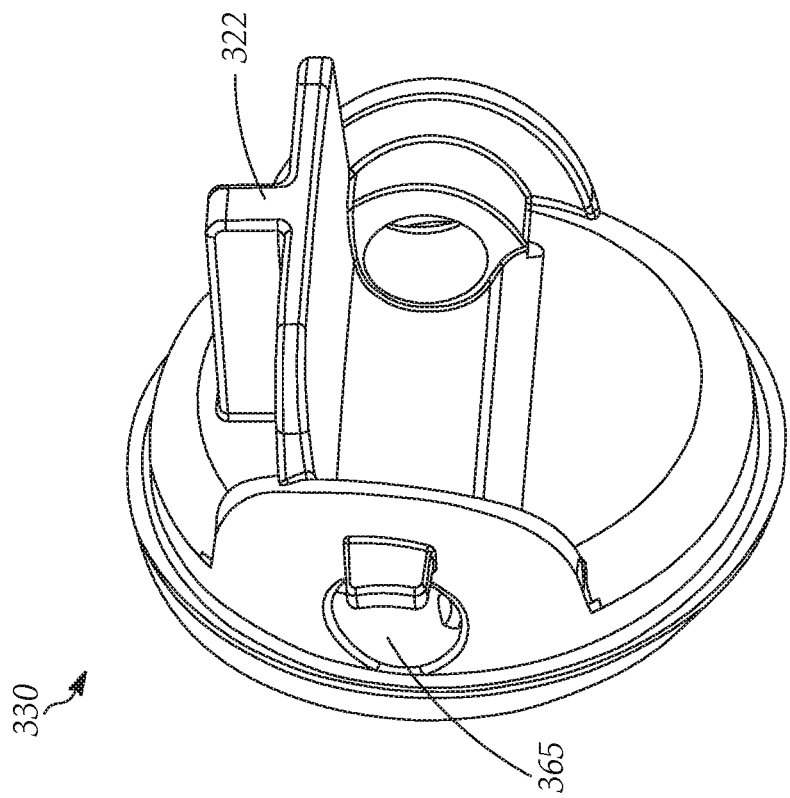
FIG. 45 is a rear perspective view of the restrictor member of the FIG. 44.

The restrictor member 330 is shown in further detail in the perspective views shown in FIGS. 44-45. The restrictor member 330 includes a keyed bore 365 for receiving the shaft 334 extending from the vane 332, and further includes a stop 322 that limits permissible rotation of the restrictor member 330 relative to a seat 324 of the adjustment member 353. As shown in the front view of FIG. 46, like the restrictor member 130, the restrictor member 330 further comprises an offset designed to facilitate movement of the restrictor member 330 between a closed position and an open position. More specifically, a greater surface area of the face 340 of the restrictor member 330 is positioned on one side of the bore 365 for receiving the shaft 334 than on the other side of the bore 365. As described above with regards to the restrictor member 130, this offset produces an opening torque about the shaft 334 during periods of exhalation.

Figure 47:
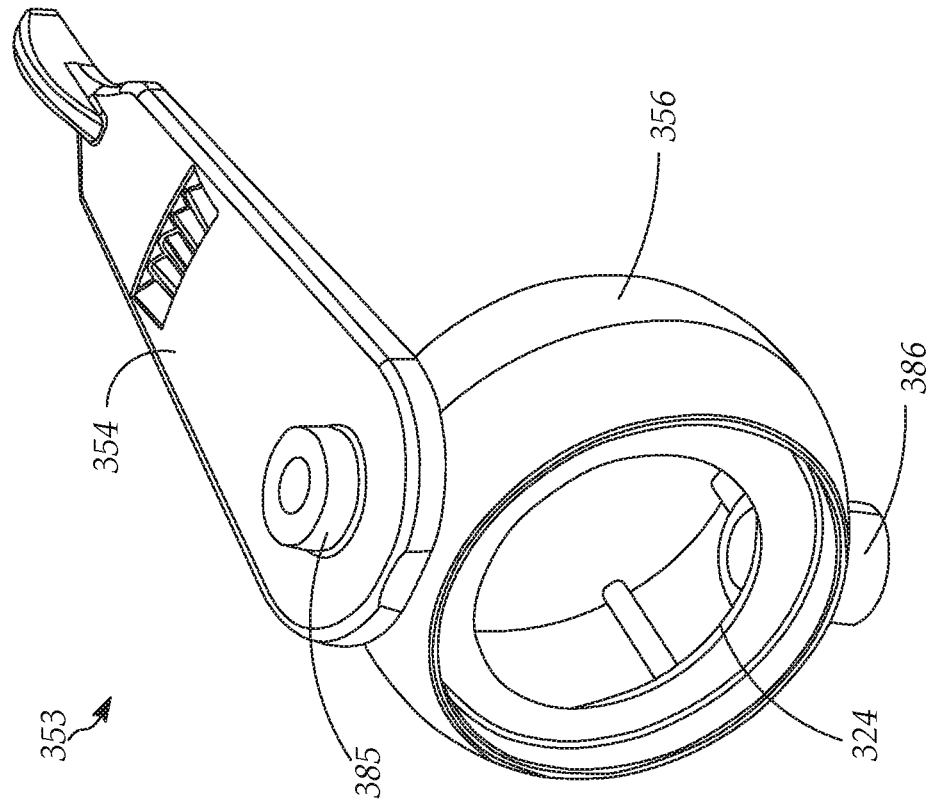
FIG. 47 is a front perspective view of an adjustment mechanism of the OPEP device of FIG. 35.
Figure 48:
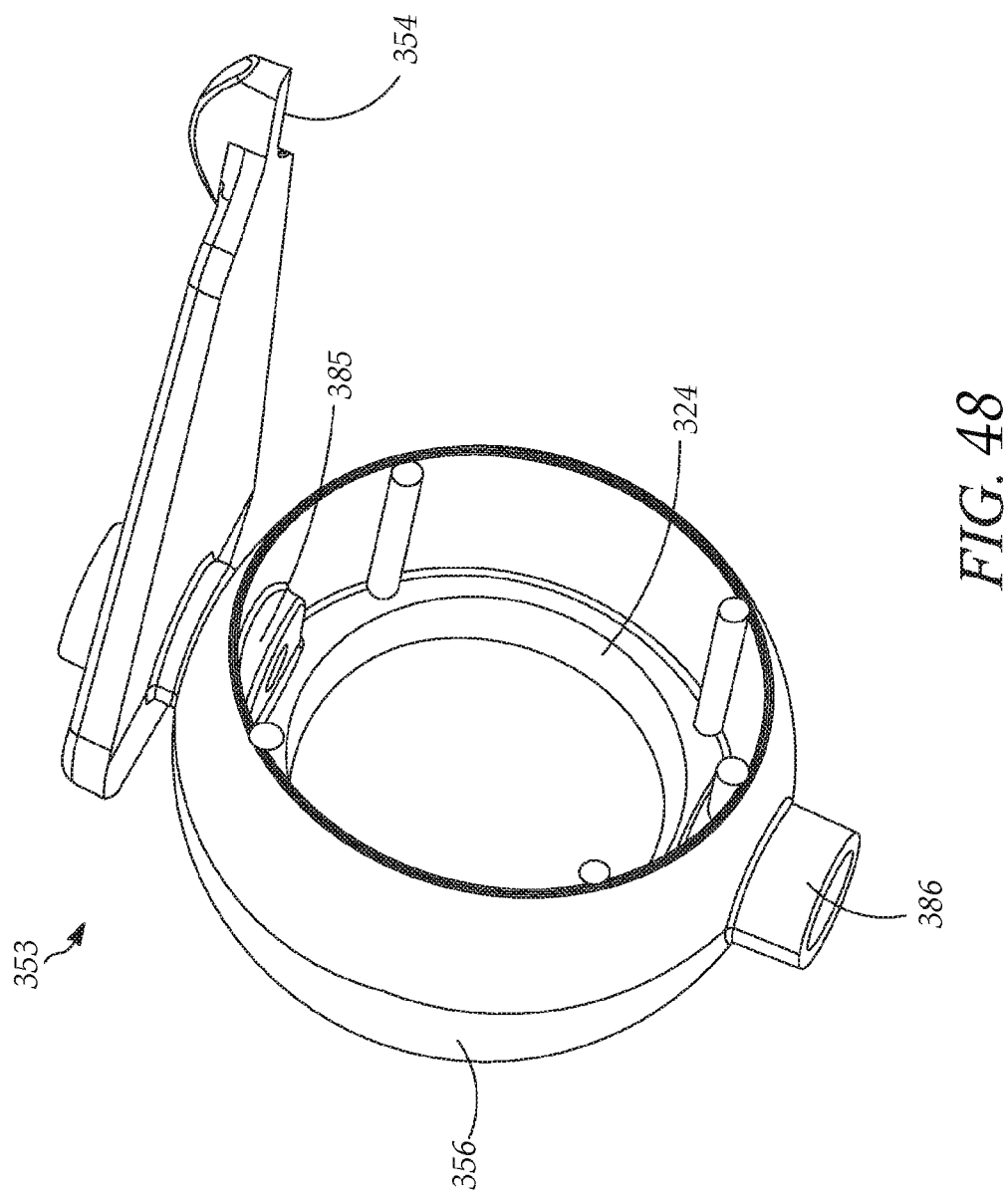
FIG. 48 is a rear perspective view of the adjustment mechanism of FIG. 47.

The adjustment mechanism 353 is shown in further detail in the front and rear perspective views of FIGS. 47 and 48. In general, the adjustment mechanism includes a frame 356 adapted to engage the sealing edge 370 of the flexible cylinder 371 formed on the inner casing 303. A circular opening in the frame 356 forms a seat 324 shaped to accommodate the restrictor member 330. In this embodiment, the seat 324 also defines the chamber inlet 304. The adjustment mechanism 353 further includes an arm 354 configured to extend from the frame 356 to a position beyond the housing 302 in order to permit a user to selectively adjust the orientation of the adjustment mechanism 353, and therefore the chamber inlet 304, when the OPEP device 300 is fully assembled. The adjustment mechanism 353 also includes an upper bearing 385 and a lower bearing 386 for receiving the shaft 334.

Figure 49:
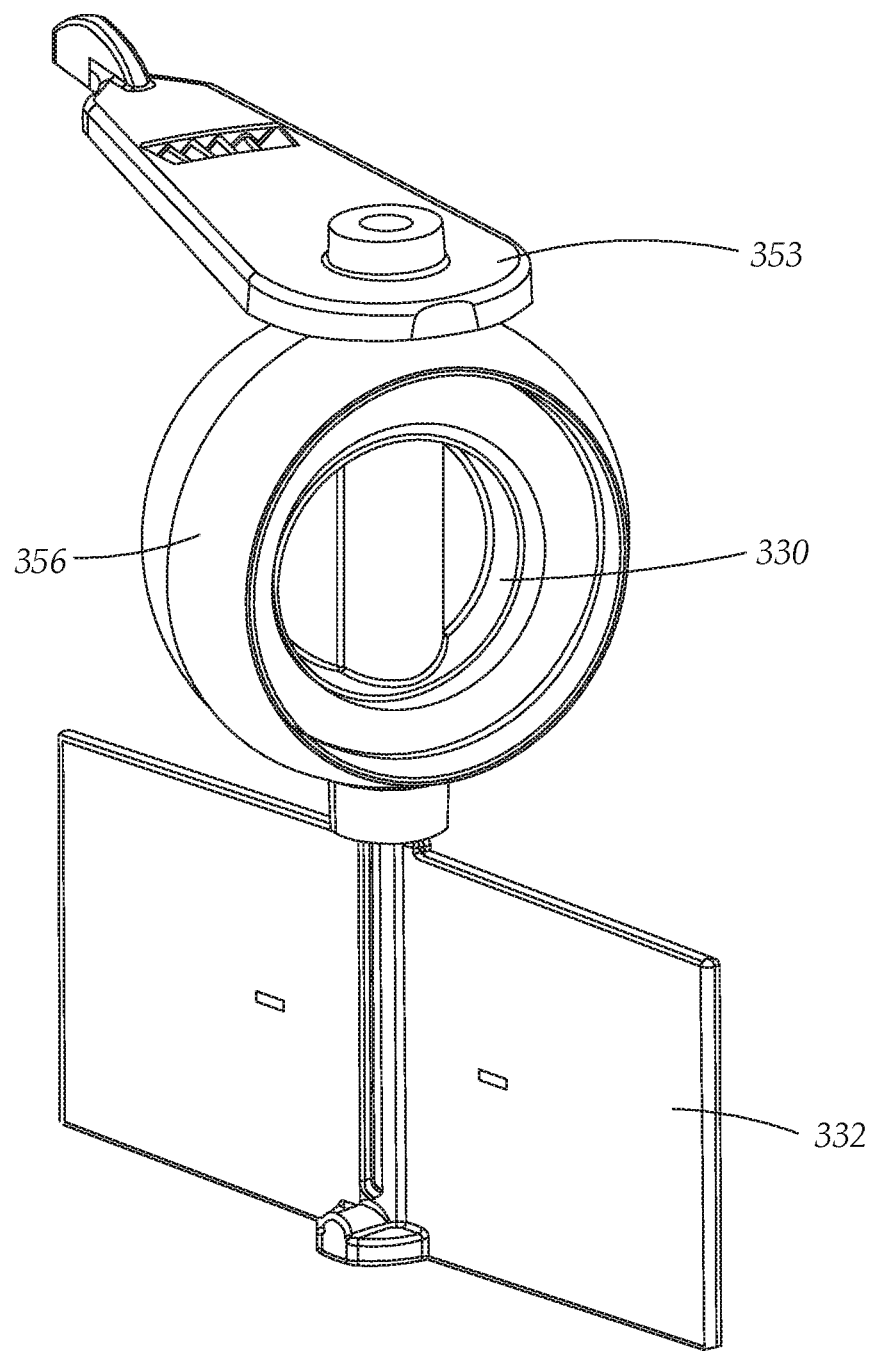
FIG. 49 is a front perspective view of the adjustment mechanism of FIGS. 47-48 assembled with the restrictor member of FIGS. 44-46 and the vane of FIG. 43.

An assembly of the vane 332, the adjustment mechanism 353, and the restrictor member 330 is shown in the perspective view of FIG. 49. As previously explained, the vane 332 and the restrictor member 330 are operatively connected by the shaft 334 such that rotation of the vane 332 results in rotation of the restrictor member 330, and vice versa. In contrast, the adjustment mechanism 353, and therefore the seat 324 defining the chamber inlet 304, is configured to rotate relative to the vane 332 and the restrictor member 330 about the shaft 334. In this way, a user is able to rotate the arm 354 to selectively adjust the orientation of the chamber inlet 304 relative to the restrictor member 330 and the housing 302. For example, a user may increase the frequency and amplitude of the OPEP therapy administered by the OPEP device 800 by rotating the arm 354, and therefore the frame 356, in a clockwise direction. Alternatively, a user may decrease the frequency and amplitude of the OPEP therapy administered by the OPEP device 300 by rotating the adjustment arm 354, and therefore the frame 356, in a counter-clockwise direction. Furthermore, as shown for example in FIGS. 35 and 37, indicia may be provided on the housing 302 to aid the user in the setting of the appropriate configuration of the OPEP device 300.

The variable nozzle 336 is shown in further detail in the front and rear perspective views of FIGS. 50 and 51. The variable nozzle 336 in the OPEP device 300 is similar to the variable nozzle 236 described above with regards to the OPEP device 200, except that the variable nozzle 336 also includes a base plate 387 configured to fit within one end 385 (see FIGS. 41-42) of the inner casing 303 and maintain the variable nozzle 336 between the rear section 305 and the inner casing 303. Like the variable nozzle 236, the variable nozzle 336 and base plate 387 may be made of silicone.

The one-way valve 384 is shown in further detail in the front perspective view of FIG. 52. In general, the one-way valve 384 comprises a post 388 adapted for mounting in the front section 301 of the housing 302, and a flap 389 adapted to bend or pivot relative to the post 388 in response to a force or a pressure on the flap 389. Those skilled in the art will appreciate that other one-way valves may be used in this and other embodiments described herein without departing from the teachings of the present disclosure. As seen in FIGS. 39-40, the one-way valve 384 may be positioned in the housing 302 between the mouthpiece 309 and the inhalation port 311.

As discussed above in relation to the OPEP device 100, the OPEP device 300 may be adapted for use with other or additional interfaces, such as an aerosol delivery device. In this regard, the OPEP device 300 is equipped with an inhalation port 311 (best seen in FIGS. 35-36 and 38-40) in fluid communication with the mouthpiece 309. As noted above, the inhalation port may include a separate one-way valve 384 (best seen in FIGS. 39-40 and 52) configured to permit a user of the OPEP device 300 both to inhale the surrounding air through the one-way valve 384 and to exhale through the chamber inlet 304, without withdrawing the mouthpiece 309 of the OPEP device 300 between periods of inhalation and exhalation. In addition, the aforementioned commercially available aerosol delivery devices may be connected to the inhalation port 311 for the simultaneous administration of aerosol therapy (upon inhalation) and OPEP therapy (upon exhalation).

The OPEP device 300 and the components described above are further illustrated in the cross-sectional views shown in FIGS. 39-40. For purposes of illustration, the cross-sectional view of FIG. 39 is shown without all the internal components of the OPEP device 300.

The front section 301, the rear section 305, and the inner casing 303 are assembled to form a first chamber 314 and a second chamber 318. As with the OPEP device 100, an exhalation flow path 310, identified by a dashed line, is defined between the mouthpiece 309 and at least one of the first chamber outlet 306 (best seen in FIGS. 39-40 and 42) and the second chamber outlet 308 (best seen in FIG. 41), both of which are formed within the inner casing 303. As a result of the inhalation port 311 and the one-way valve 348, the exhalation flow path 310 begins at the mouthpiece 309 and is directed toward the chamber inlet 304, which in operation may or may not be blocked by the restrictor member 330. After passing through the chamber inlet 304, the exhalation flow path 310 enters the first chamber 314 and makes a 180° turn toward the variable nozzle 336. After passing through an orifice 338 of the variable nozzle 336, the exhalation flow path 310 enters the second chamber 318. In the second chamber 318, the exhalation flow path 310 may exit the second chamber 318, and ultimately the housing 302, through at least one of the first chamber outlet 306 or the second chamber outlet 308. Those skilled in the art will appreciate that the exhalation flow path 310 identified by the dashed line is exemplary, and that air exhaled into the OPEP device 300 may flow in any number of directions or paths as it traverses from the mouthpiece 309 or chamber inlet 304 to the first chamber outlet 306 or the second chamber outlet 308. As previously noted, the administration of OPEP therapy using the OPEP device 300 is otherwise the same as described above with regards to the OPEP device 100.

Solely by way of example, the follow operating conditions, or performance characteristics, may be achieved by an OPEP device according to the OPEP device 300, with the adjustment dial 354 set for increased frequency and amplitude:

| Flow Rate (lpm) | 10 | 30 |
| Frequency (Hz) | 7 | 20 |
| Upper Pressure (cm H2O) | 13 | 30 |
| Lower Pressure (cm H2O) | 1.5 | 9 |
| Amplitude (cm H2O) | 11.5 | 21 |

The frequency and amplitude may decrease, for example, by approximately 20% with the adjustment dial 354 set for decreased frequency and amplitude. Other frequency and amplitude targets may be achieved by varying the particular configuration or sizing of elements, for example, increasing the length of the vane 332 results in a slower frequency, whereas, decreasing the size of the orifice 338 results in a higher frequency. The above example is merely one possible set of operating conditions for an OPEP device according to the embodiment described above.

Fourth OPEP Embodiment

Turning to FIGS. 53-56, another embodiment of a respiratory treatment device 400 is shown. Unlike the previously described OPEP devices, the respiratory treatment device 400 is configured to administer oscillating pressure therapy upon both exhalation and inhalation. Those skilled in the art will appreciate that the concepts described below with regards to the respiratory treatment device 400 may be applied to any of the previously described OPEP devices, such that oscillating pressure therapy may be administered upon both exhalation and inhalation. Likewise, the respiratory treatment device 400 may incorporate any of the concepts above regarding the previously described OPEP devices, including for example, a variable nozzle, an inhalation port adapted for use with an aerosol delivery device for the administration of aerosol therapy, an adjustment mechanism, etc.

Figure 53:
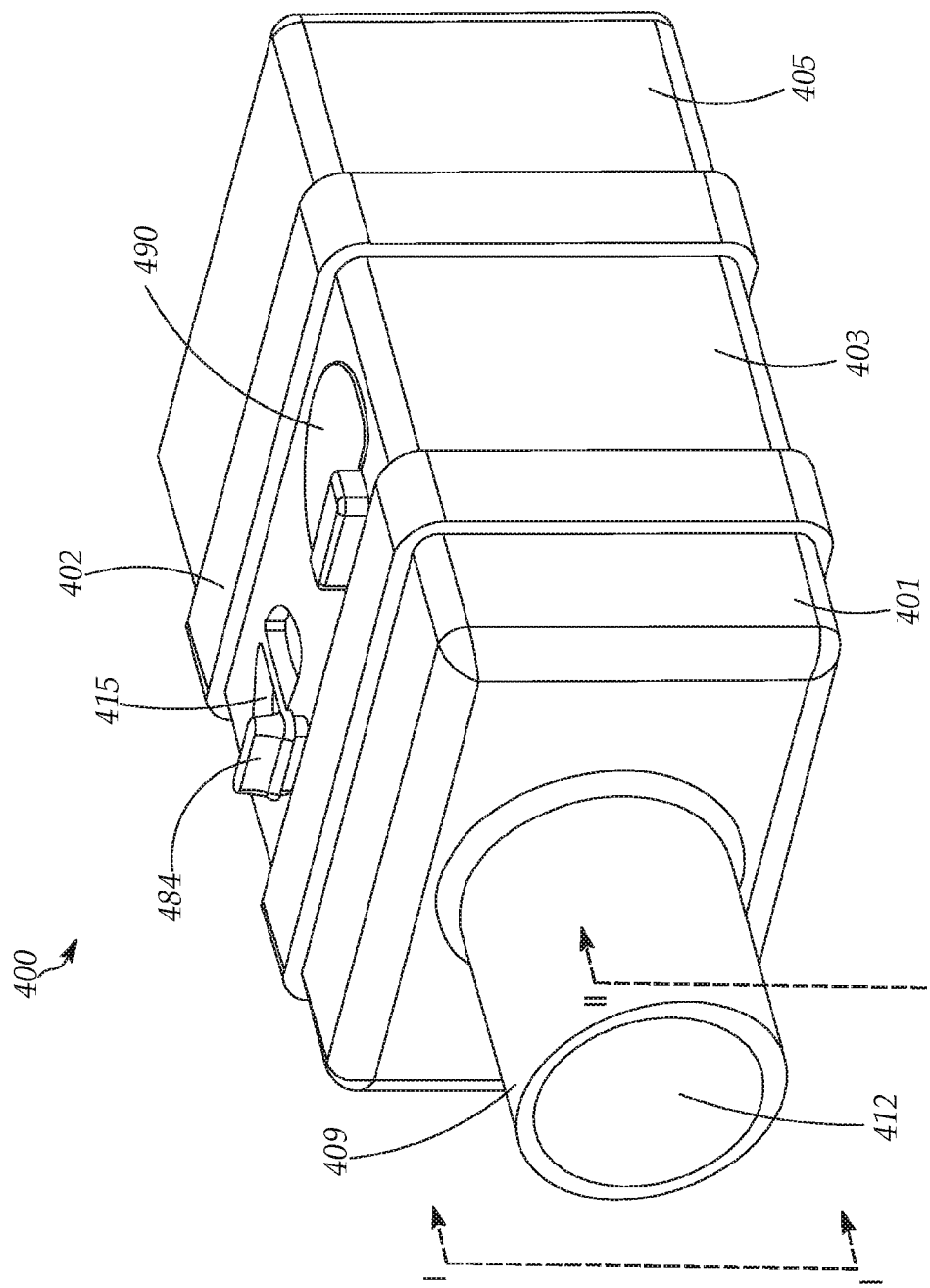
FIG. 53 is a perspective view of another embodiment of a respiratory treatment device.
Figure 54:
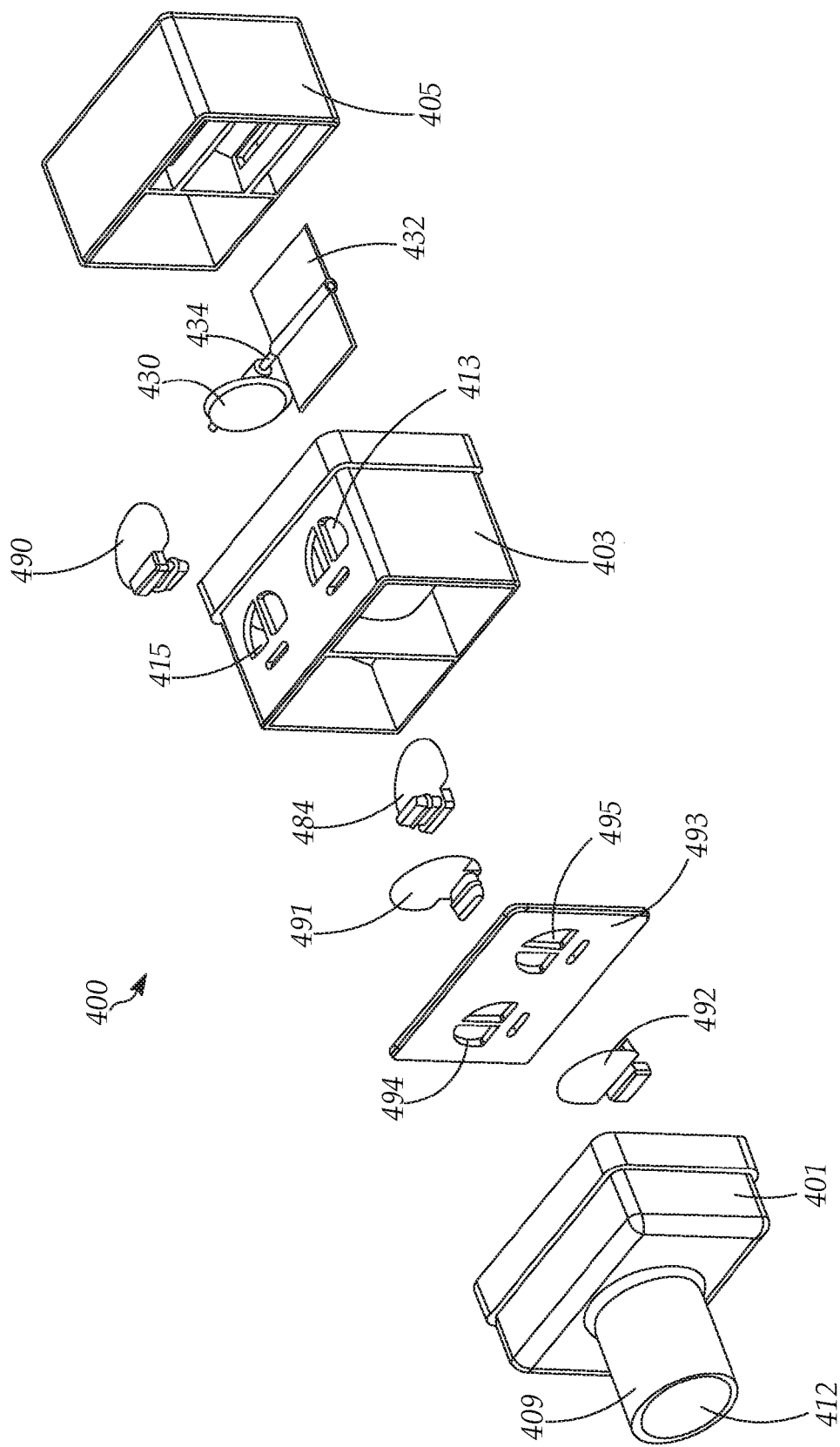
FIG. 54 is an exploded view of the respiratory treatment device of FIG. 53.

As shown in FIGS. 53 and 54, the respiratory treatment device 400 includes a housing 402 having a front section 401, a middle section 403, and a rear section 405. As with the OPEP devices described above, the housing 402 is openable so that the contents of the housing 402 may be accessed for cleaning and/or selective replacement or adjustment of the components contained therein to maintain ideal operating conditions. The housing 402 further includes a first opening 412, a second opening 413, and a third opening 415.

Although the first opening 412 is shown in in FIGS. 53 and 54 in association with a mouthpiece 409, the first opening 412 may alternatively be associated with other user interfaces, for example, a gas mask or a breathing tube. The second opening 413 includes a one-way exhalation valve 490 configured to permit air exhaled into the housing 402 to exit the housing 402 upon exhalation at the first opening 412. The third opening 415 includes a one-way inhalation valve 484 configured to permit air outside the housing 402 to enter the housing 402 upon inhalation at the first opening 412. As shown in greater detail in FIG. 54, the respiratory treatment device 400 further includes a manifold plate 493 having an exhalation passage 494 and an inhalation passage 495. A one-way valve 491 is adapted to mount to within the manifold plate 493 adjacent to the exhalation passage 494 such that the one-way valve 491 opens in response to air exhaled into the first opening 412, and closes in response to air inhaled through the first opening 412. A separate one-way valve 492 is adapted to mount within the manifold pate 493 adjacent to the inhalation passage 495 such that the one-way valve 492 closes in response to air exhaled into the first opening 412, and opens in response to air inhaled through the first opening 412. The respiratory treatment device 400 also includes a restrictor member 430 and a vane 432 operatively connected by a shaft 434, the assembly of which may operate in the same manner as described above with regards to the disclosed OPEP devices.

Figure 55:
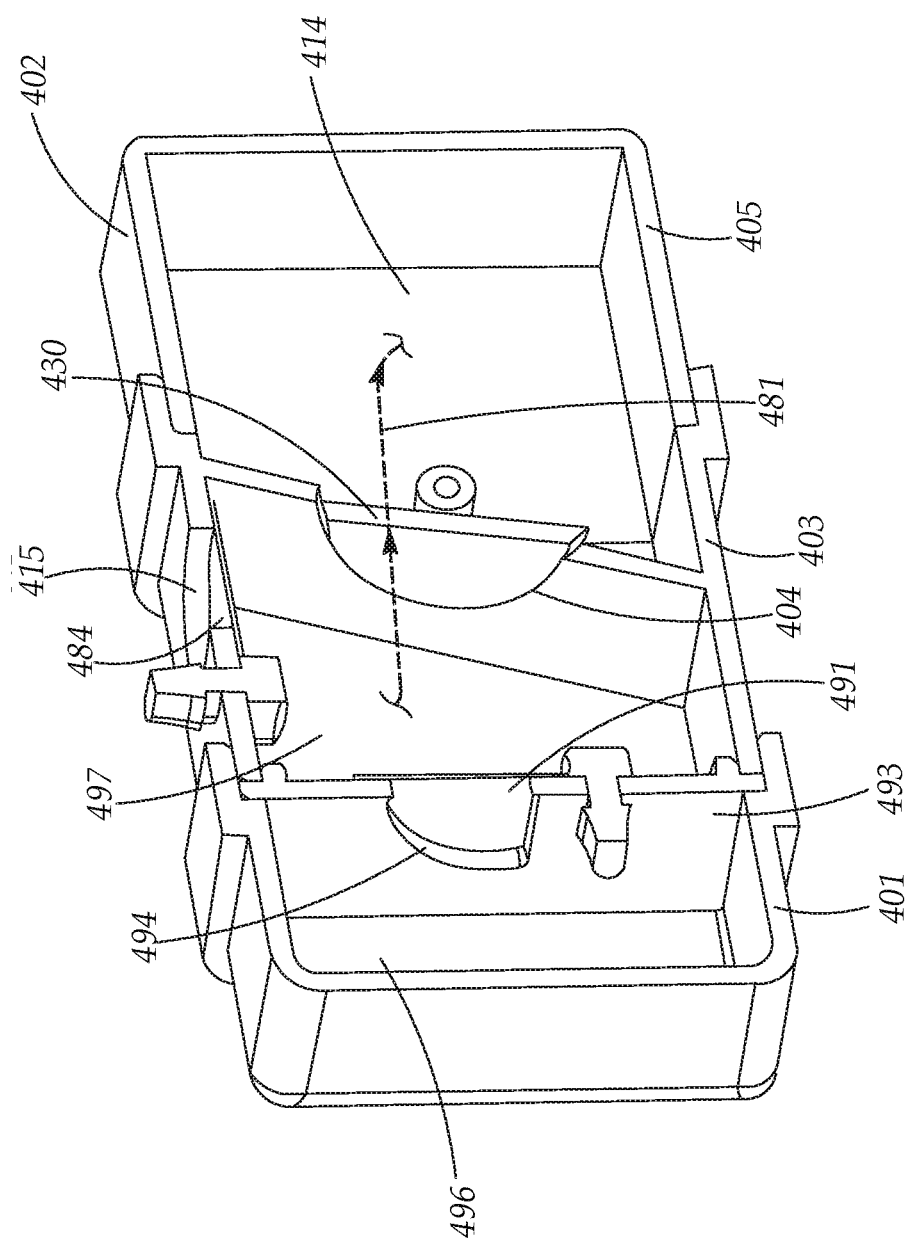
FIG. 55 is a cross-sectional perspective view taken along line I in FIG. 53 of the respiratory treatment device shown with the internal components of the device.
Figure 56:
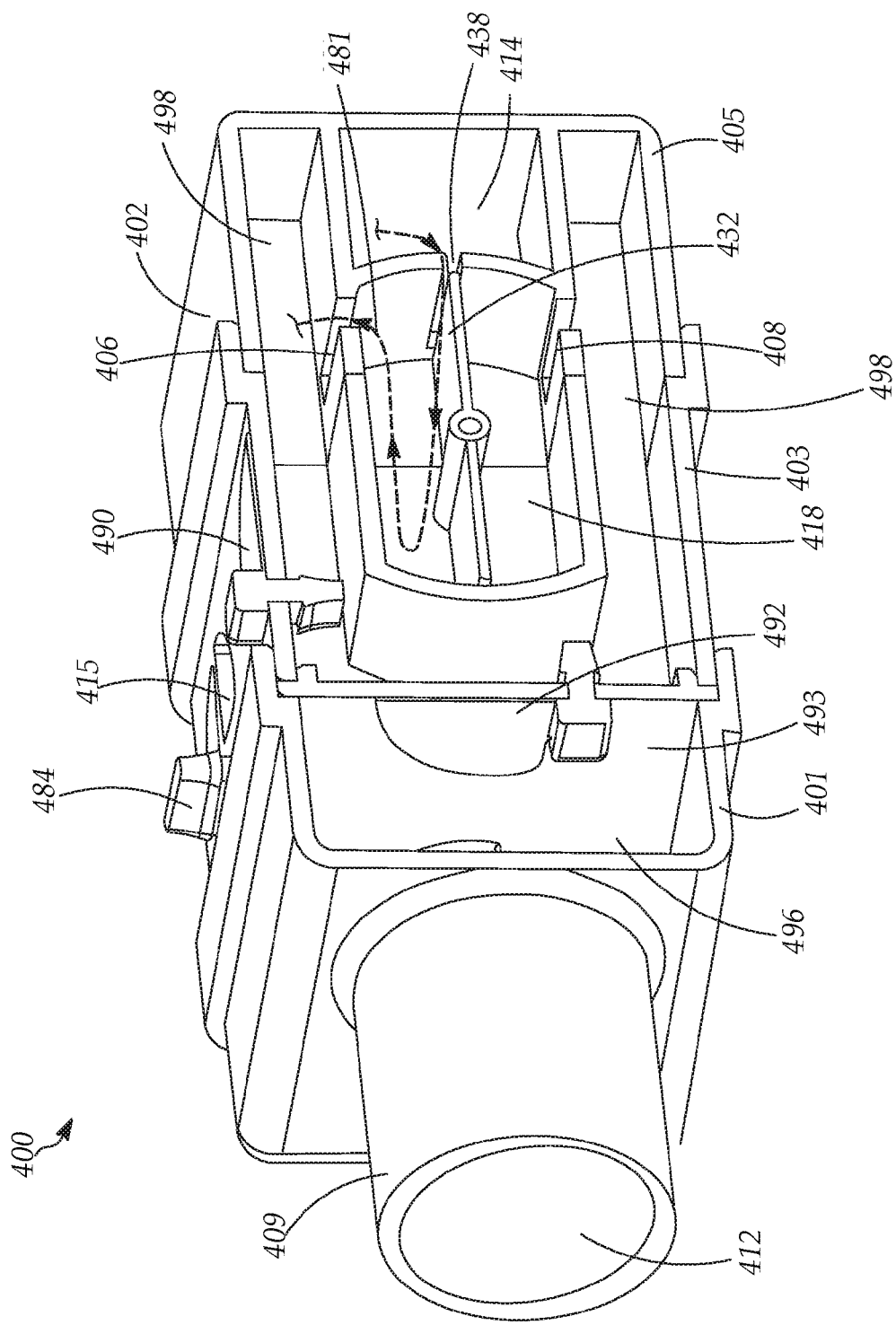
FIG. 56 is a cross-sectional perspective view taken along line II in FIG. 53 of the respiratory treatment device shown with the internal components of the device.

Referring now to FIGS. 55 and 56, cross-sectional perspective views are shown taken along lines I and II, respectively, in FIG. 53. The respiratory treatment device 400 administers oscillating pressure therapy upon both inhalation and exhalation in a manner similar to that shown and described above with regards to the OPEP devices. As described in further detail below, the OPEP device 400 includes a plurality of chambers (i.e., more than one). Air transmitted through the first opening 412 of the housing 402, whether inhaled or exhaled, traverses a flow path that passes, at least in part, past a restrictor member 430 housed in a first chamber 414, and through a second chamber 418 which houses a vane 432 operatively connected to the restrictor member 430. In this regard, at least a portion of the flow path for both air exhaled into or inhaled from the first opening 412 is overlapping, and occurs in the same direction.

For example, an exemplary flow path 481 is identified in FIGS. 55 and 56 by a dashed line. Similar to the previously described OPEP devices, the restrictor member 430 is positioned in the first chamber 414 and is movable relative to a chamber inlet 404 between a closed position, where the flow of air through the chamber inlet 404 is restricted, and an open position, where the flow of air through the chamber 404 inlet is less restricted. After passing through the chamber inlet 404 and entering the first chamber 414, the exemplary flow path 481 makes a 180-degree turn, or reverses longitudinal directions (i.e., the flow path 481 is folded upon itself), whereupon the exemplary flow path 481 passes through an orifice 438 and enters the second chamber 418. As with the previously described OPEP devices, the vane 432 is positioned in the second chamber 418, and is configured to reciprocate between a first position and a second position in response to an increased pressure adjacent the vane, which in turn causes the operatively connected restrictor member 430 to repeatedly move between the closed position and the open position. Depending on the position of the vane 432, air flowing along the exemplary flow path 481 is directed to one of either a first chamber outlet 406 or a second chamber outlet 408. Consequently, as inhaled or exhaled air traverses the exemplary flow path 481, pressure at the chamber inlet 404 oscillates.

The oscillating pressure at the chamber inlet 404 is effectively transmitted back to a user of the respiratory treatment device 400, i.e., at the first opening 412, via a series of chambers. As seen in FIGS. 55 and 56, the respiratory treatment device includes a first additional chamber 496, a second additional chamber 497, and a third additional chamber 498, which are described in further detail below.

The mouthpiece 409 and the first additional chamber 496 are in communication via the first opening 412 in the housing 402. The first additional chamber 496 and the second additional chamber 497 are separated by the manifold plate 493, and are in communication via the exhalation passage 494. The one-way valve 491 mounted adjacent to the exhalation passage 494 is configured to open in response to air exhaled into the first opening 412, and close in response to air inhaled through the first opening 412.

The first additional chamber 496 and the third additional chamber 498 are also separated by the manifold plate 493, and are in communication via the inhalation passage 495. The one-way valve 492 mounted adjacent to the inhalation passage 495 is configured to close in response to air exhaled into the first opening 412, and open in response to air inhaled through the first opening 412.

Air surrounding the respiratory treatment device 400 and the second additional chamber 497 are in communication via the third opening 415 in the housing 402. The one-way valve 484 is configured to close in response to air exhaled in to the first opening 412, and open in response to air inhaled through the first opening 412.

Air surrounding the respiratory treatment device 400 and the third additional chamber 498 are in communication via the second opening 413 in the housing 402. The one way-valve 490 mounted adjacent the second opening 413 is configured to open in response to air exhaled into the first opening 412, and close in response to air inhaled through the first opening 412. The third additional chamber 498 is also in communication with the second chamber 418 via the first chamber outlet 406 and the second chamber outlet 408.

Figure 57:
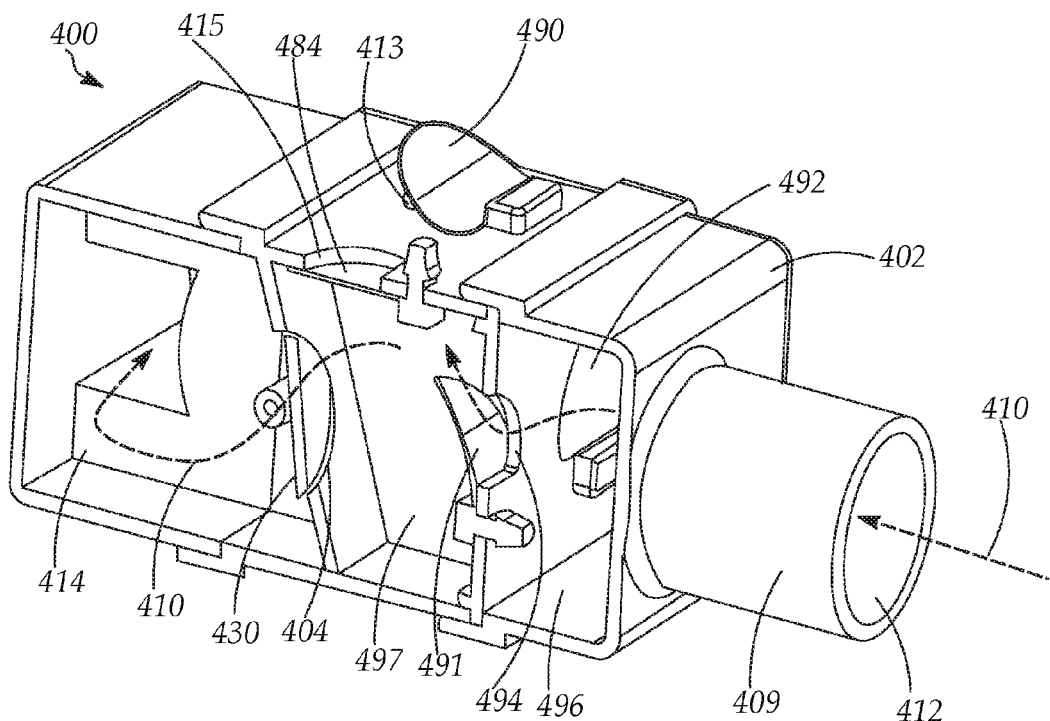
FIG. 57 is a different cross-sectional perspective view taken along line I in FIG. 53 of the respiratory treatment device, showing a portion of an exemplary exhalation flow path.
Figure 58:
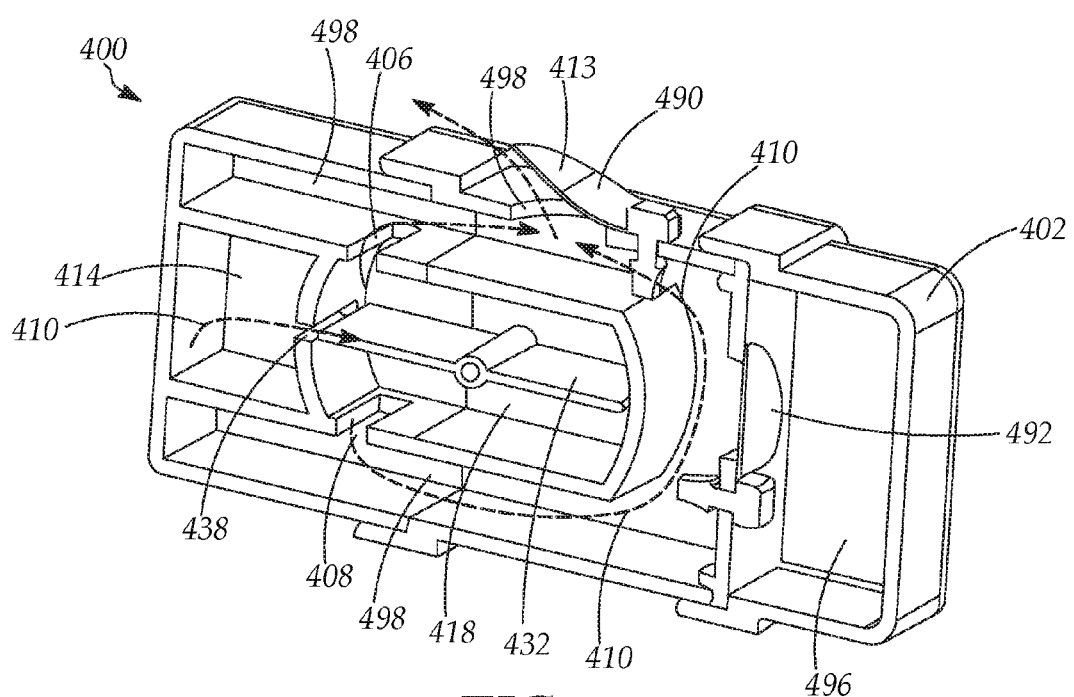
FIG. 58 is a different cross-sectional perspective view taken along line II in FIG. 53, showing a portion of an exemplary exhalation flow path.

Referring now to FIGS. 57-58, cross-sectional perspective views taken along lines I and II, respectively, of FIG. 53, illustrate an exemplary exhalation flow path 410 formed between the first opening 412, or the mouthpiece 409, and the second opening 413. In general, upon exhalation by a user into the first opening 412 of the housing 402, pressure builds in the first additional chamber 496, causing the one-way valve 491 to open, and the one-way valve 492 to close. Exhaled air then enters the second additional chamber 497 through the exhalation passage 494 and pressure builds in the second additional chamber 497, causing the one-way valve 484 to close and the restrictor member 430 to open. The exhaled air then enters the first chamber 414 through the chamber inlet 404, reverses longitudinal directions, and accelerates through the orifice 438 separating the first chamber 414 and the second chamber 418. Depending on the orientation of the vane 432, the exhaled air then exits the second chamber 418 through one of either the first chamber outlet 406 or the second chamber outlet 408, whereupon it enters the third additional chamber 498. As pressure builds in the third additional chamber 498, the one-way valve 490 opens, permitting exhaled air to exit the housing 402 through the second opening 413. Once the flow of exhaled air along the exhalation flow path 410 is established, the vane 432 reciprocates between a first position and a second position, which in turn causes the restrictor member 430 to move between the closed position and the open position, as described above with regards to the OPEP devices. In this way, the respiratory treatment device 400 provides oscillating therapy upon exhalation.

Figure 59:
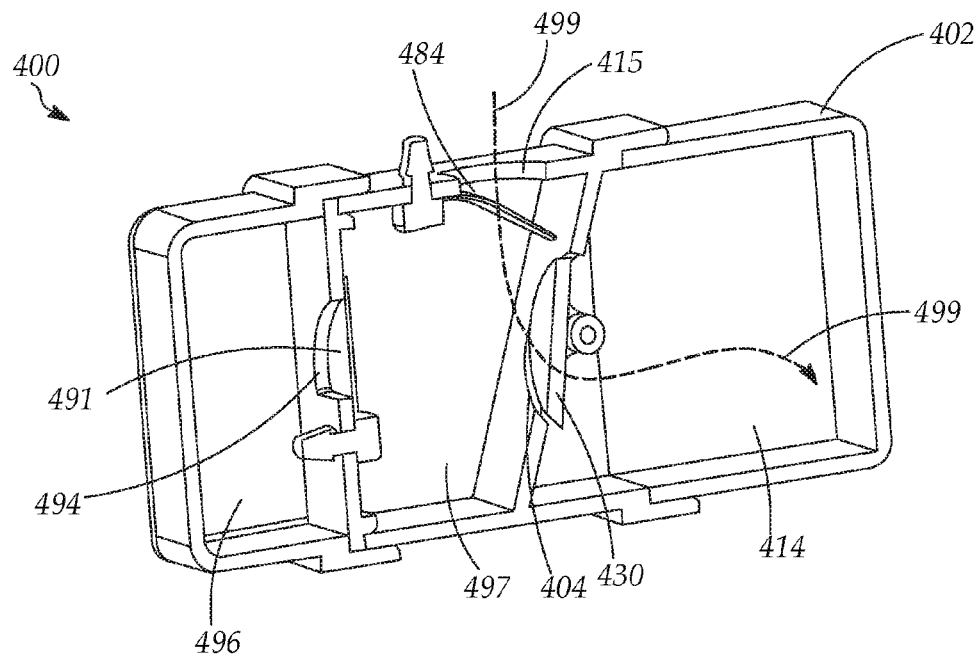
FIG. 59 is another cross-sectional perspective view taken along line I in FIG. 53, showing a portion of an exemplary inhalation flow path.
Figure 60:
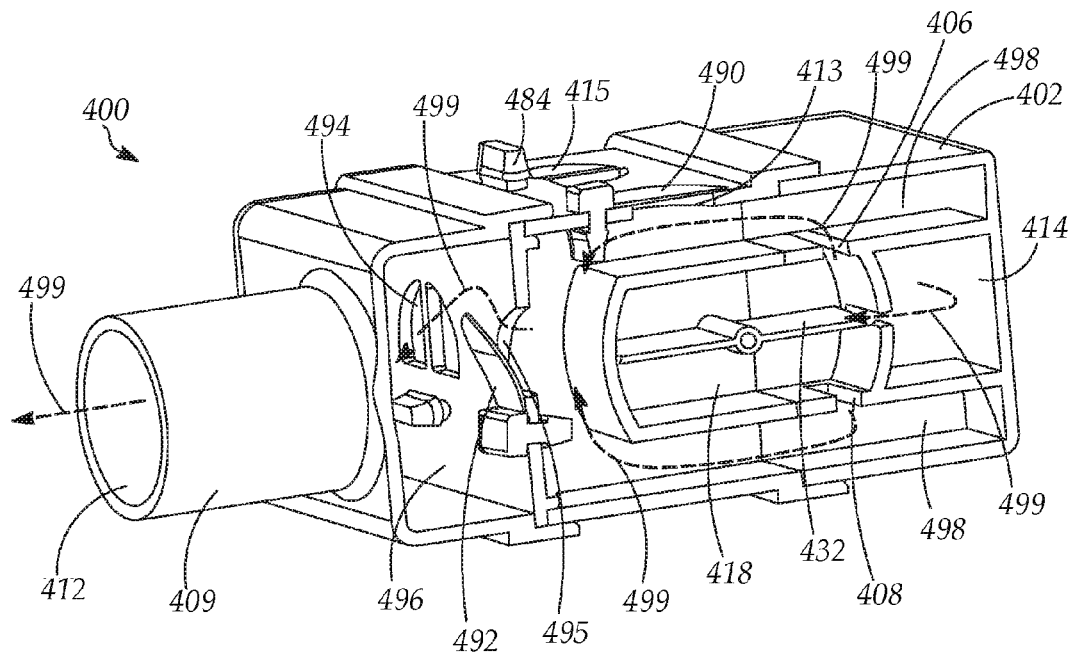
FIG. 60 is another cross-sectional perspective view taken along line II in FIG. 53, showing a portion of an exemplary inhalation flow path.

Referring now to FIGS. 59-60, different cross-sectional perspective views taken along lines I and II, respectively, of FIG. 53, illustrate an exemplary inhalation flow path 499 formed between the third opening 415 and the first opening 412, or the mouthpiece 409. In general, upon inhalation by a user through the first opening 412, pressure drops in the first additional chamber 496, causing the one-way valve 491 to close, and the one-way valve 492 to open. As air is inhaled from the third additional chamber 498 into the first additional chamber 496 through the inhalation passage 495, pressure in the third additional chamber 498 begins to drop, causing the one-way valve 490 to close. As pressure continues to drop in the third additional chamber 498, air is drawn from the second chamber 418 through the first chamber outlet 406 and the second camber outlet 408. As air is drawn from the second chamber 918, air is also drawn from the first chamber 414 through the orifice 438 connecting the second chamber 418 and the first chamber 414. As air is drawn from the first chamber 414, air is also drawn from the second additional chamber 497 through the chamber inlet 404, causing the pressure in the second additional chamber 497 to drop and the one-way valve 484 to open, thereby permitting air to enter the housing 402 through third opening 415. Due to the pressure differential between the first additional chamber 496 and the second additional chamber 497, the one-way valve 491 remains closed. Once the flow of inhaled air along the inhalation flow path 499 is established, the vane 432 reciprocates between a first position and a second position, which in turn causes the restrictor member 430 to move between the closed position and the open position, as described above with regards to the OPEP devices. In this way, the respiratory treatment device 400 provides oscillating therapy upon inhalation.

Respiratory Muscle Training

RMT includes pressure threshold resistance. A pressure threshold resistor requires a user to achieve and maintain a set pressure in order to inhale or exhale through the pressure threshold resistor and/or the attached respiratory device. In general, a pressure threshold resistor includes a one way valve that is biased toward a closed position. As a pressure force created by a user inhaling through or exhaling into the device overcomes the biasing force, the valve opens and permits inhalation or exhalation. In order to continue with inhalation or exhalation, the user must generate and maintain a pressure that matches or exceeds the pressure threshold that overcomes the biasing force on the valve. A pressure threshold resistor may be use during inhalation to generate a negative pressure for administration of RMT, and during exhalation to generate a positive pressure for administration of RMT.

RMT also include flow resistance. A flow resistor limits the flow of air during inhalation or exhalation through the flow resistor and/or the attached respiratory device in order to generate negative or positive pressure for administration RMT. In general, a flow resistor restricts the flow of air through an orifice. The pressure generated by the flow restrictor may be controlled by changing the size of the orifice and/or an inhalation or exhalation flow rate.

Pressure Threshold Resistors

Figure 61A:
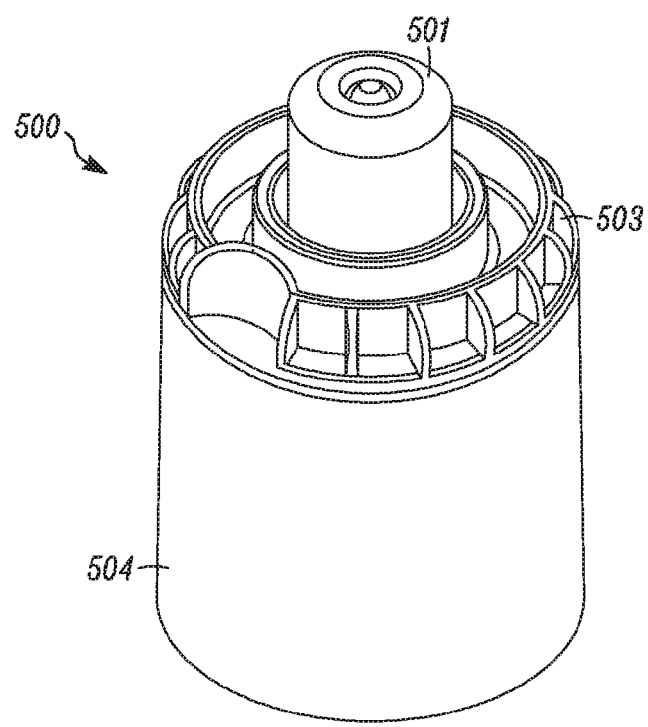
FIGS. 61A-E includes perspective, side, top, cross-sectional, and exploded views of a pressure threshold resistor.
Figure 61B:
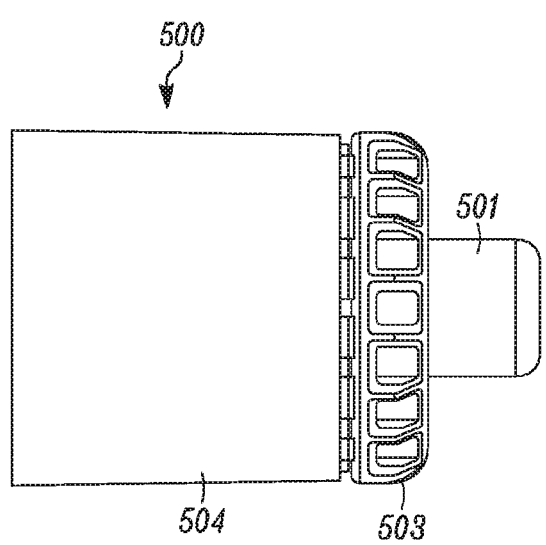
Figure 61C:
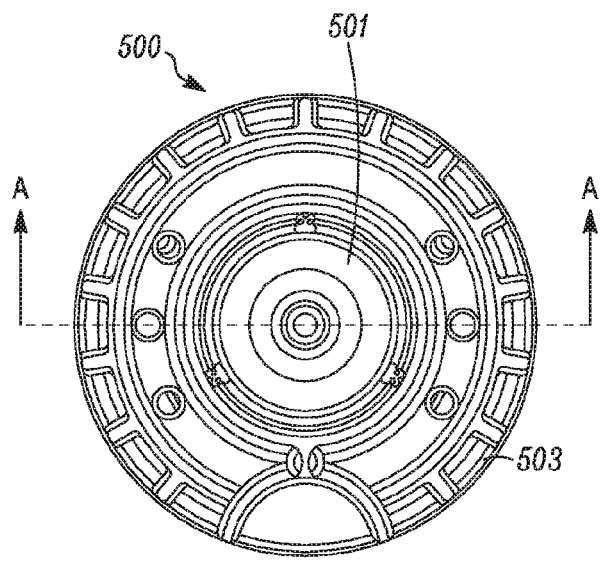
Figure 61D:
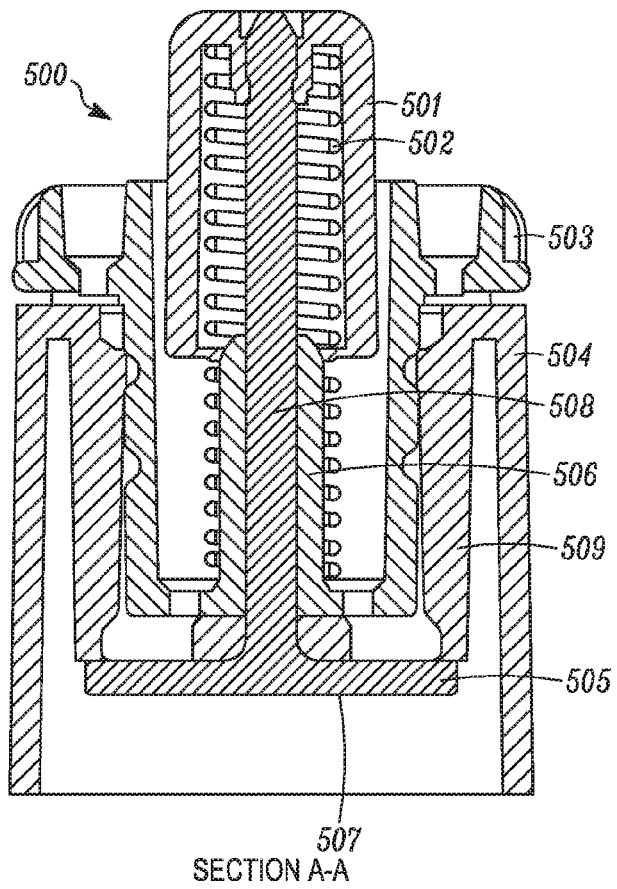
Figure 61E:
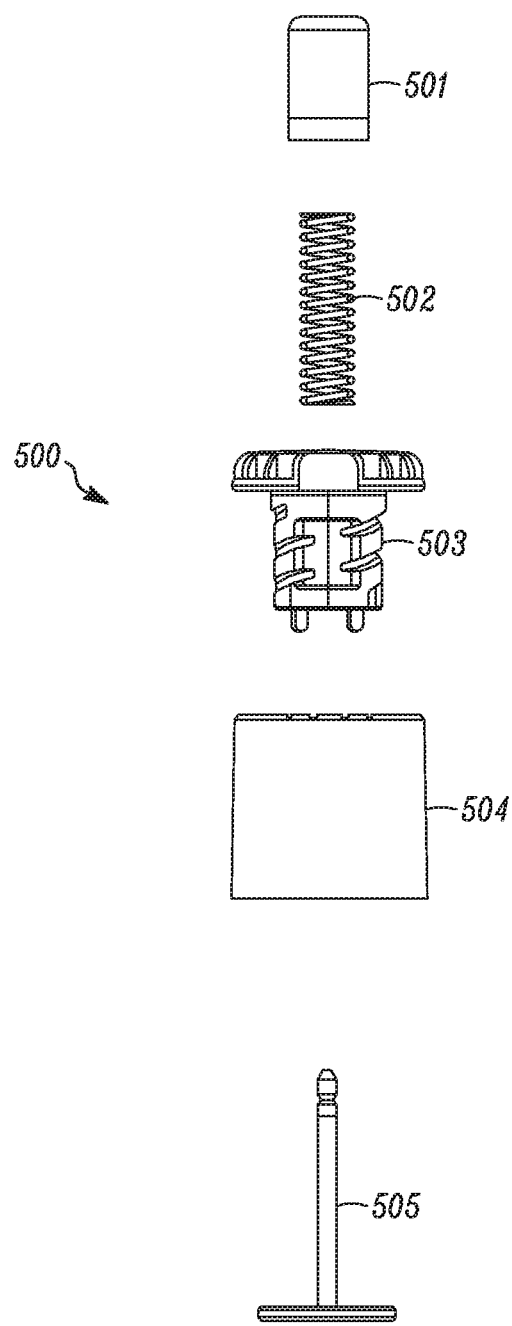

Turning to FIGS. 61A-E, perspective, side, top, cross-sectional, and exploded views of a pressure threshold resistor 500 are shown. In general, as shown in FIG. 61D and 61E, the pressure threshold resistor 500 includes a spring seat 501, a spring 502, an adjuster 503, a connector 504, and a valve 505.

The connector 504 may be shaped and size to be removably connectable to the inhalation port of any number of respiratory devices, including for example, the inhalation port 311 of OPEP device 300. The connector 504 may be removably connectable to respiratory devices by any suitable means, including a friction fit, threaded engagement, a snap fit, or the like.

A center cylinder 509 of the connector 504 is configured to receive the adjuster 503 via a threaded engagement. An end of the center cylinder 509 also functions as a seat for the valve 505.

The adjuster 503 functions as a thumb screw and is configured for threaded engagement with the connector 504. In this way, the adjuster 503 may be rotated by a user relative to the connector 504 to raise or lower the position of the adjuster 503 relative to the connector 504. As discussed below, the adjuster 503 may be selectively rotated by a user to increase or decrease the threshold pressure required to open the valve 505. The adjuster 503 also includes a center cylinder 506 sized for sliding engagement with the spring 502. The center cylinder 506 also includes an interior portion sized for sliding engagement with a post 508 of the valve 505. The base of the center cylinder 506 acts as stop for the spring 502.

The valve 505 includes a valve face 507 and a post 508. The valve face 507 is configured to engage the seat defined by an end of the cylinder 509 of the connector 504. As stated above, the post 508 is configured to fit within and be in sliding engagement with the center cylinder 506 of the adjuster 503. An end of the post 508 is connected to the spring seat 501. In an alternative embodiment, the end of the post 508 may be removably connected to the spring seat 501.

The spring seat 501 is shaped and sized to fit within the adjuster 503. In general, the spring seat 501 is cylindrical and includes an interior portion that receives the spring 502 and the post 508 of the valve 505. A base of the interior portion of the spring seat 501 also acts as stop for the spring 502.

The spring 502 may be a coil spring. Springs of different lengths and spring constants (k) may be selected and/or replaced, as desired, to increase or decrease the threshold pressures required to open the valve 505. When assembled in the pressure threshold resistor 500 as shown, the spring 502 is under compression.

In operation, the pressure threshold resistor 500 is connected to an inhalation port of a respiratory device via the connector 504. When a user inhales through the respiratory device, a negative pressure is created at the inhalation port. Consequently, the negative pressure creates a force that pulls on the valve face 507 of the valve 505. However, the valve 505 and the valve face 507 are also biased by the spring 502 (via the post 508 and spring seat 501) toward a closed position, and therefore, remain closed until the pressure threshold required to open the valve 505 is reached. As a user continues to inhale, or inhale with greater strength, the negative pressure created at the inhalation port increases, until the pressure threshold is reached, at which point the valve face 507 is pulled away from the seat formed by the center cylinder 509 of the connector 504, and the valve 505 opens. Once the valve 505 is opened, a user is able to inhale air surrounding the pressure threshold resistor 500 and the respiratory device, so long as the negative pressure generated at the inhalation port by the user's inhalation maintains or exceeds the threshold pressure required to open the valve 505. If the user stops inhaling, or if the negative pressure generated by the user's inhalation drops below the threshold pressure, the biasing force of the spring 502 closes the valve 505.

Figure 62A:
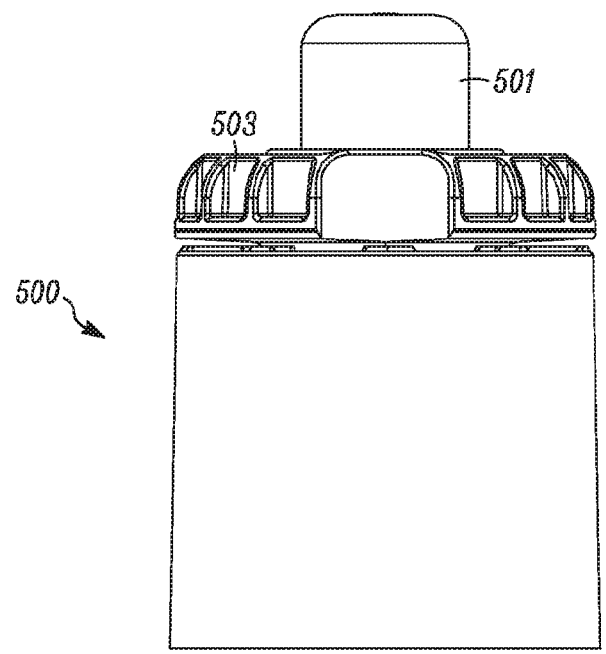
FIGS. 62A-B are side views of the pressure threshold resistor of FIGS. 61A-E, illustrating the adjustability of the threshold pressure required to open the valve of the pressure threshold resistor.
Figure 62B:
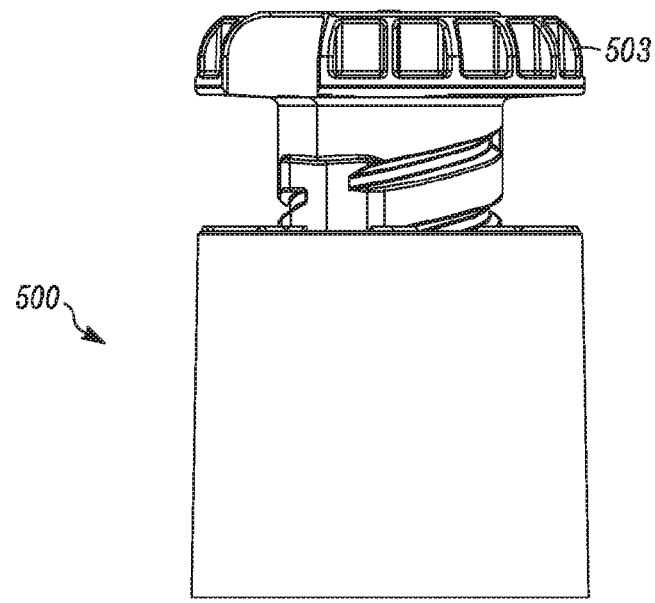
Figure 63A:
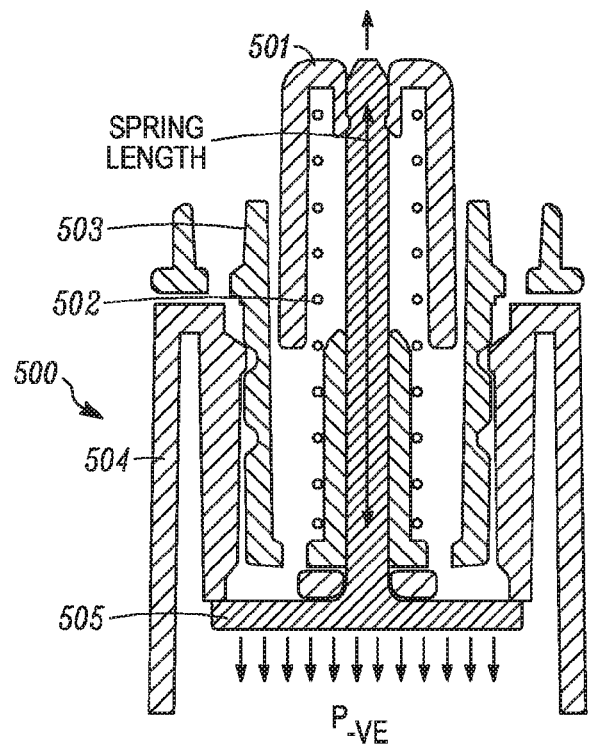
FIGS. 63A-B are cross-sectional views of the pressure threshold resistor of FIGS. 61A-E, illustrating the adjustability of the threshold pressure required to open the valve of the pressure threshold resistor.
Figure 63B:
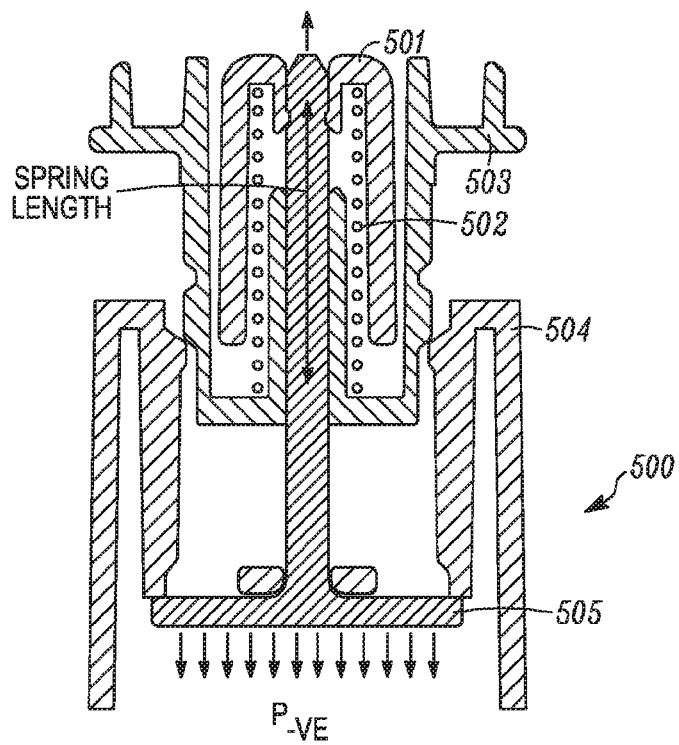

FIGS. 62A-B and 63A-B are side and cross-sectional views of the pressure threshold resistor 500, further illustrating selective adjustment of the pressure threshold required to open the valve 505. FIGS. 62A and 63A illustrate the pressure threshold resistor 500 at a "low setting," while FIGS. 62B and 63B illustrate the pressure threshold resistor 500 at a "high setting." The pressure threshold resistor 500 may be selectively adjusted between a low setting, as shown in FIG. 62A, and a high setting, as shown in FIG. 62B, by rotating the adjuster 503 relative to the connector 504. As shown in FIGS. 63A and 63B, rotation of the adjuster 503 effectively increases the compression of the spring 502, which in turn increases the bias of the spring 502 acting on the valve 505. Consequently, the pressure threshold required to open the valve 505 also increases. In this way, the pressure threshold is selectively adjustable by a user.

Figure 64A:
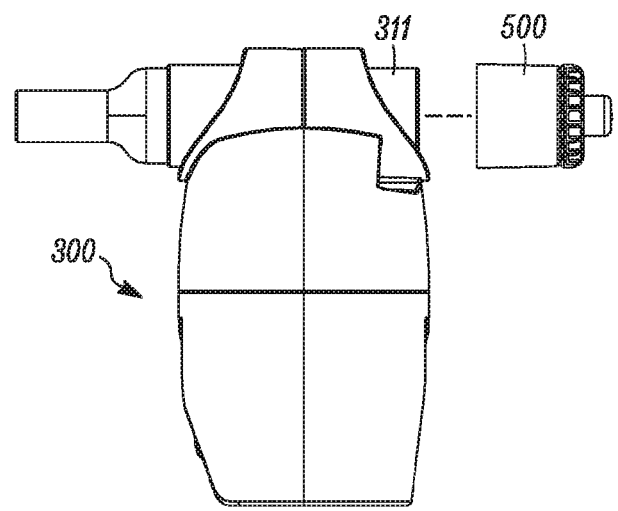
FIGS. 64A-D are side, perspective, and partial cross-sectional views of the pressure threshold resistor of FIGS. 61A-E connected to the OPEP device of FIG. 35.
Figure 64B:
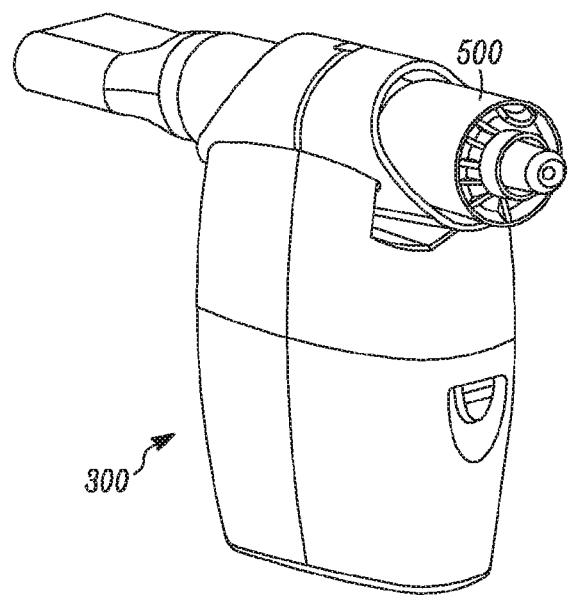
Figure 64C:
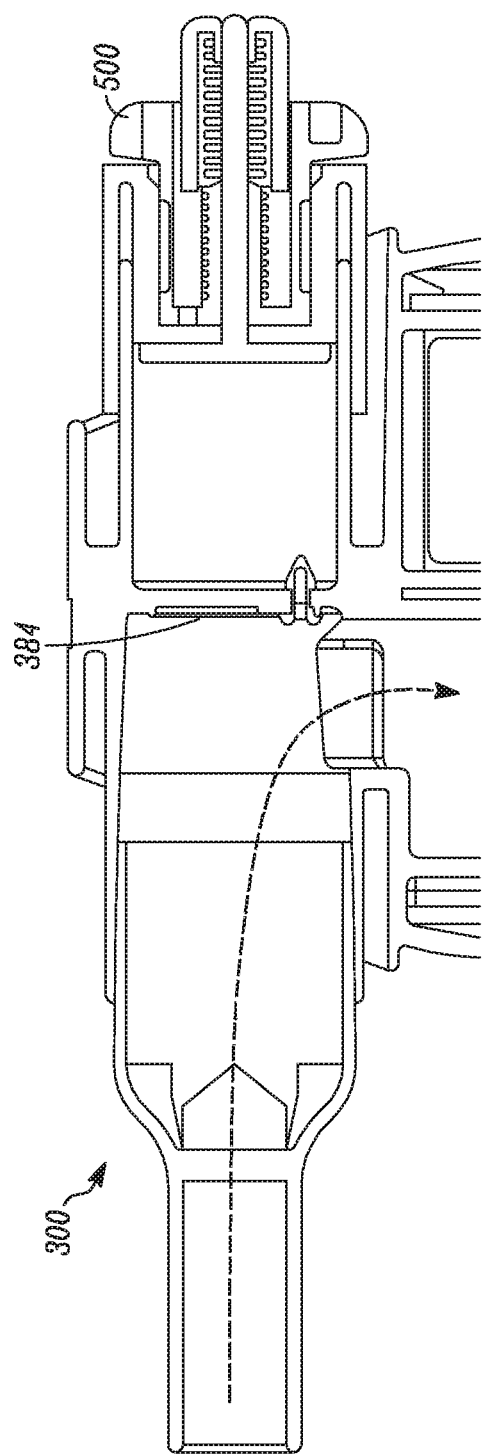
Figure 64D:
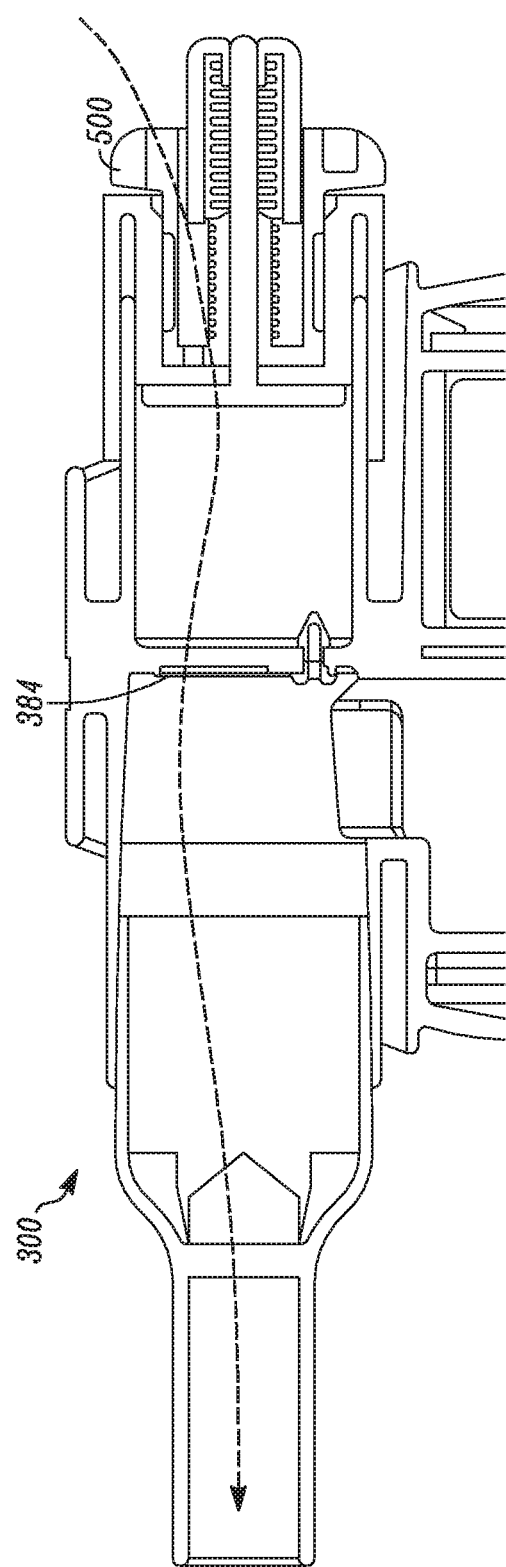

As previously noted, the pressure threshold resistor 500 is connectable to the inhalation port of any number of respiratory devices, including for example, the inhalation port 311 of OPEP device 300, as shown in FIGS. 64A-D. Operation of the OPEP device 300 with the pressure threshold resistor 500 is illustrated in FIGS. 64C-D. In general, when a user exhales into the OPEP device 300, the one way valve 384 remains closed due to positive exhalation pressure, forcing exhaled air along the exemplary flow path identified by dashed line in FIG. 64C through the OPEP device 300 for administration of OPEP therapy. On the other hand, when a user inhales, the one way valve 384 opens due to negative inhalation pressure. At the same time, the orifice of the variable nozzle 336 described above in relation to the OPEP device 300 closes due to the negative inhalation pressure. With the orifice of the variable nozzle 336 closed and the one-way valve 384 open, as the user continues to inhale, or inhale with greater strength, a negative pressure created at the inhalation port 311 increases until the pressure threshold is reached, at which point the valve 505 of the threshold pressure resistor 500 opens, allowing air surrounding the pressure threshold resistor 500 and the OPEP device 300 to flow along the exemplary flow path identified by dashed line in FIG. 64D.

Figure 65A:
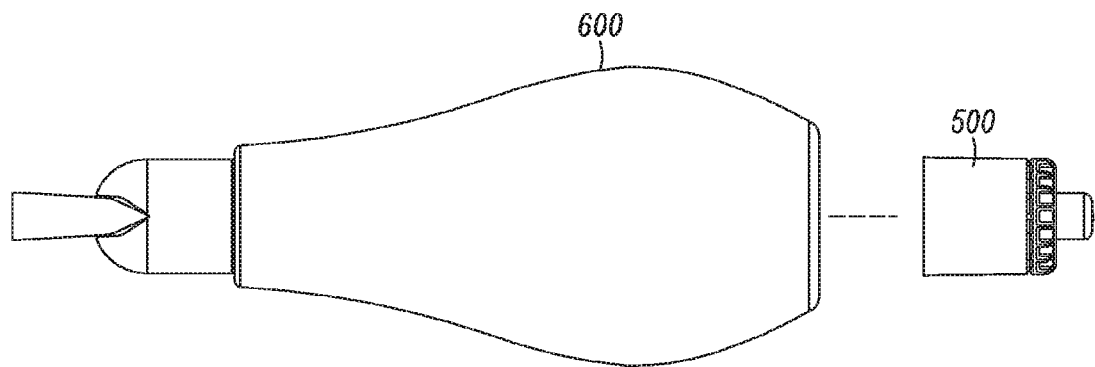
FIGS. 65A-B are side and perspective views of the pressure threshold resistor of FIGS. 61A-E connected to another commercially available OPEP device.
Figure 65B:
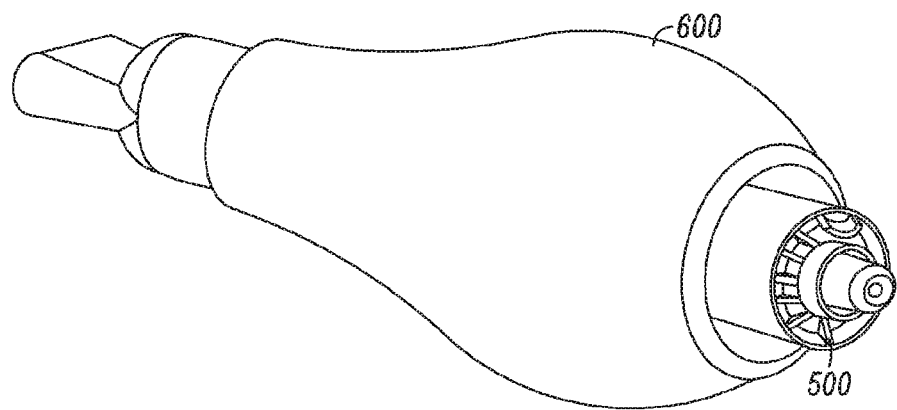

The pressure threshold resistor 500, as well as the other RMT devices disclosed herein, may also be sized and shaped for use on other respiratory treatment devices. Solely by way of example, FIGS. 65A-B show the pressure threshold resistor 500 connected to an inhalation port an OPEP device 599 described in U.S. Pat. Nos. 6,776,159 and 7,059,324, the entireties of which are herein incorporated by reference, and commercially available under the trade name ACAPELLA® from Smiths Medical of St. Paul, Minn. The RMT devices disclosed herein may also be used with the OPEP devices described in U.S. patent application Ser. No. 13/489,894, filed on Jun. 6, 2012, now U.S. Pat. No. 9,358,417, and U.S. patent application Ser. No. 14/092,091, filed on Nov. 27, 2013, pending, the entireties of which are herein incorporated by reference.

Turning to FIGS. 66A-E, side and cross-sectional views of another embodiment of a pressure threshold resistor 520 are shown. The pressure threshold resistor 520 is shaped and sized to be removably connectable to an inhalation port of a respiratory device including, for example the inhalation port 311 of OPEP device 300. The pressure threshold resistor 520 may also be shaped and sized to be removably connectable to an exhalation port of a respiratory treatment device, including for example, as shown and described below with regard to the OPEP device 700. The pressure threshold resistor 520 may be removably connectable to respiratory devices by any suitable means, including a friction fit, threaded engagement, a snap fit, or the like. In general, the pressure threshold resistor 520 includes a housing 521 comprising a first section 522 and a second section 523, a spring seat 524, a spring 525, and a valve 526 having a valve face 528.

The first section 522 and the second section 523 of the housing 521 are removably connected to one another by a threaded engagement. The relative positon of the first section 522 to the second section 523 may also be selectively increased or decreased by rotating the first section 522 relative to the second section 523. As discussed below, one section of the housing 521 may be rotated relative to the other section of the housing 521 to selectively increase or decrease the threshold pressure required to open the valve 526 of the pressure threshold resistor 520. The first section 521 also includes a valve seat 527, while the second section 523 also includes a spring seat 524 that functions as a stop for the spring 525.

The pressure threshold resistor 520 functions in a manner similar to the pressure threshold resistor 500, except that the pressure threshold resistor 520 is configured to provide RMT upon exhalation or inhalation. As previously noted, the pressure threshold resistor 520 is connectable to an exhalation port of any number of respiratory devices. To provide RMT upon exhalation, the first section 522 of the pressure threshold resistor 520 is connected to an exhalation port of a respiratory device.

Figure 66C:
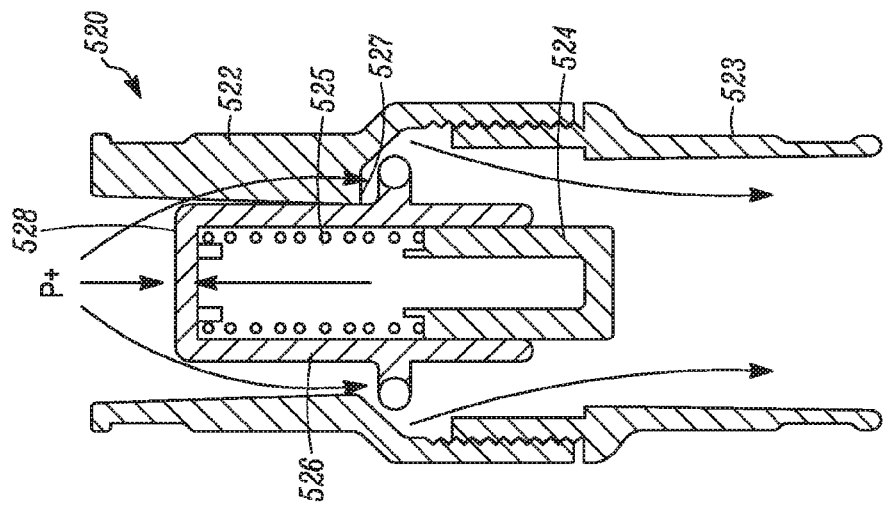
FIGS. 66A-E are side and cross-sectional views of another pressure threshold resistor.
Figure 66B:
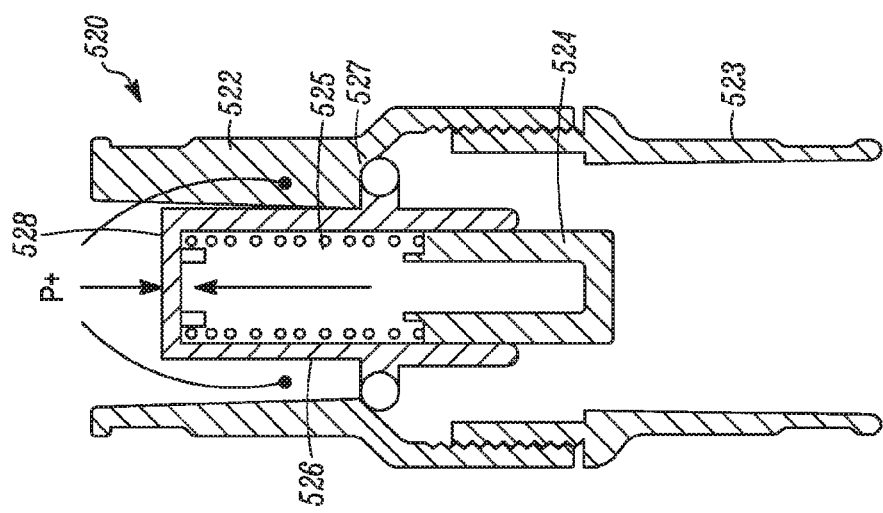
Figure 66A:
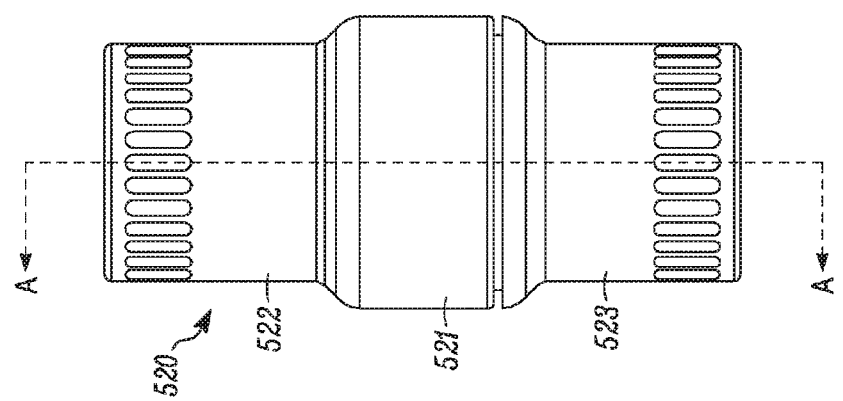

As shown in FIG. 66B, when a user exhales into a respiratory device such that a positive exhalation pressure is created at an exhalation port of the respiratory device, the positive pressure creates a force that pushed on the valve face 528 of the valve 526. However, the valve 526 and the valve face 528 are also biased by the spring 525 toward a closed position, and therefore, remain closed until the pressure threshold required to open the valve 526 is reached. As a user continues to exhale, or exhale with greater strength, the positive pressure created at the exhalation port increases, until the pressure threshold is reached, at which point the valve 526 is pushed off the valve seat 527 formed in the first section 522 of the housing 521, and the valve 526 opens, as shown in FIG. 66C. Once the valve 526 is opened, a user is able to exhale through the pressure threshold resistor 520 and the respiratory device, so long as the positive pressure generated at the exhalation port by the user's exhalation maintains or exceeds the threshold pressure required to open the valve 526. If the user stops exhaling, or if the positive pressure generated by the user's exhalation drops below the threshold pressure, the biasing force of the spring 525 closes the valve 526, as shown in FIG. 66B.

Figure 66E:
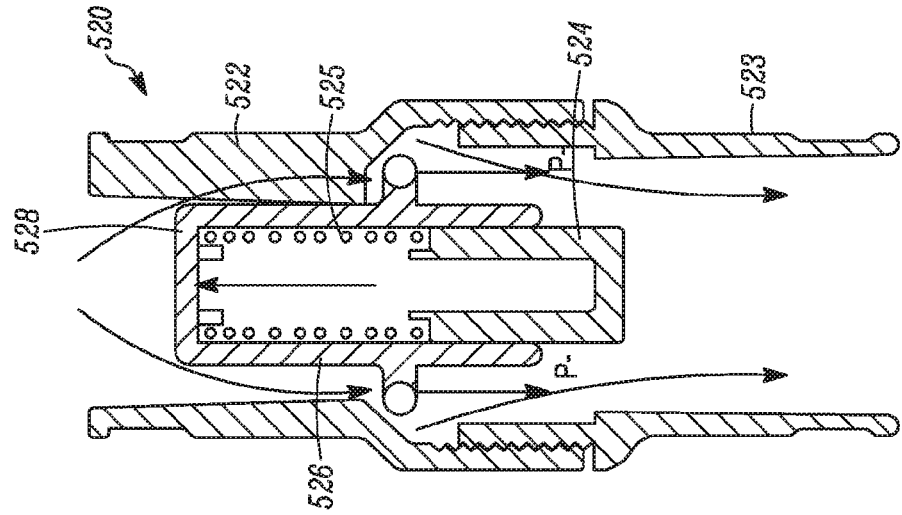
Figure 66D:
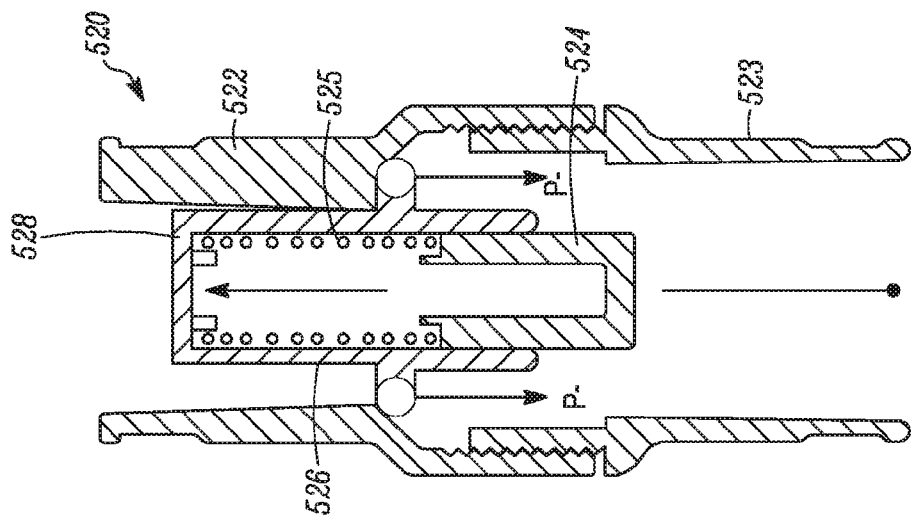

The pressure threshold resistor 520 is also connectable to an inhalation port of any number of respiratory devices. To provide RMT upon inhalation, the second section 523 of the pressure threshold resistor 520 is connected to the inhalation port of a respiratory device. As shown in FIG. 66D, when a user inhales into a respiratory device such that a negative inhalation pressure is created at an inhalation port of the respiratory device, the negative pressure creates a force that pulls on the valve 526. However, the valve 526 is also biased by the spring 525 toward a closed position, and therefore, remain closed until the pressure threshold required to open the valve 526 is reached. As a user continues to inhale, or inhale with greater strength, the negative pressure created at the inhalation port increases, until the pressure threshold is reached, at which point the valve 526 is pulled off the valve seat 527 formed in the first section 522 of the housing 521, and the valve 526 opens, as shown in FIG. 66E. Once the valve 526 is opened, a user is able to inhale air surrounding the respiratory device through the pressure threshold resistor 526 and the respiratory device, so long as the negative pressure generated at the inhalation port by the user's inhalation maintains or exceeds the threshold pressure required to open the valve 526. If the user stops inhaling, or if the negative pressure generated by the user's inhalation drops below the threshold pressure, the biasing force of the spring 525 closes the valve 526, as shown in FIG. 66D.

Figure 67B:
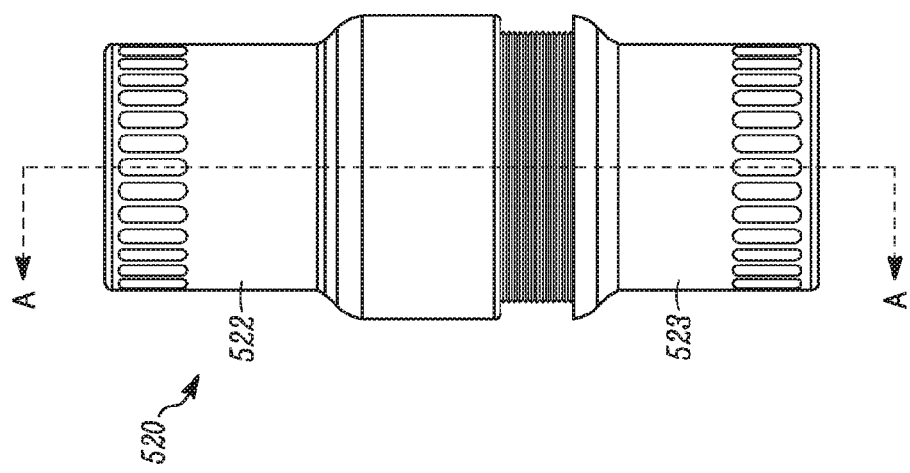
FIGS. 67A-B are side views of the pressure threshold resistor of FIGS. 66A-E illustrating the adjustability of the threshold pressure required to open the valve of the pressure threshold resistor.
Figure 67A:
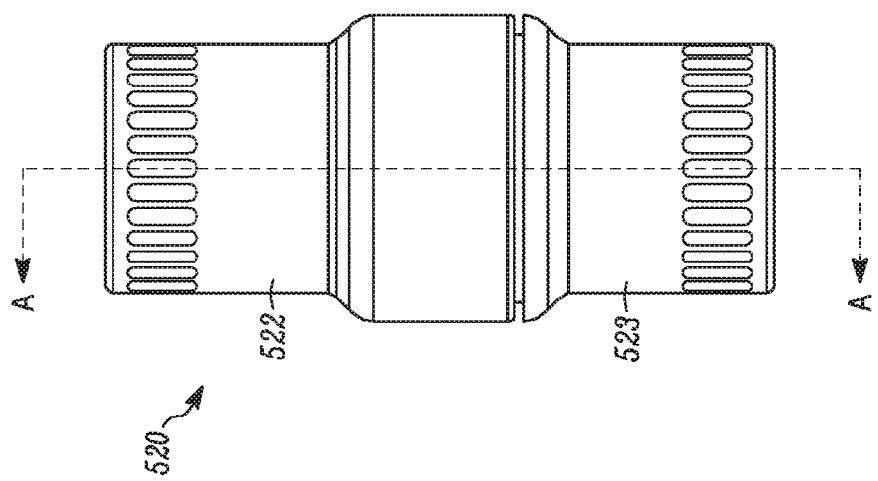
Figure 68B:
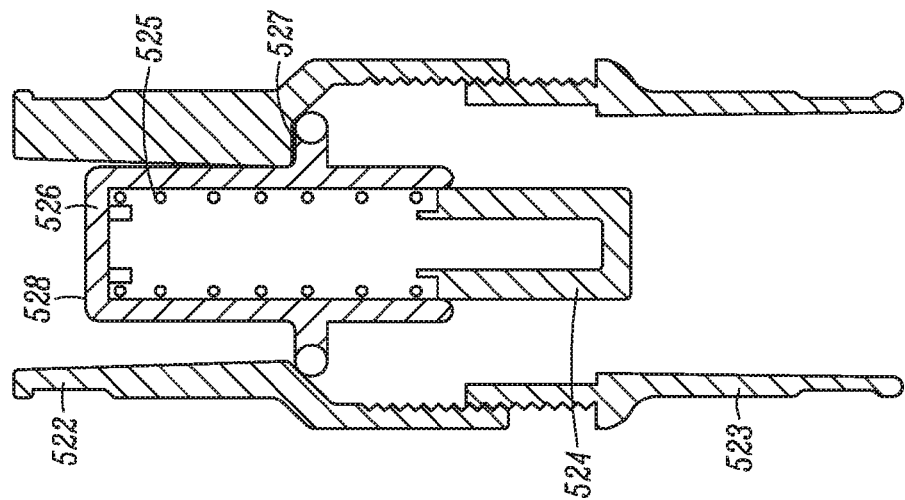
FIGS. 68A-B are cross-sectional views of the pressure threshold resistor of FIGS. 66A-E illustrating the adjustability of the threshold pressure required to open the valve of the pressure threshold resistor.
Figure 68A:
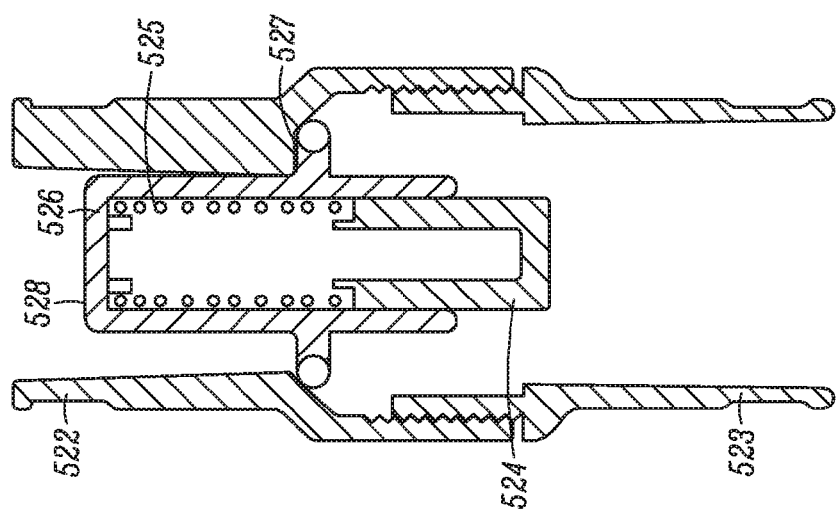

FIGS. 67A-B and 68A-B are side and cross-sectional views of the pressure threshold resistor 520, further illustrating selective adjustment of the pressure threshold required to open the valve 526. FIGS. 67A and 68A illustrate the pressure threshold resistor 520 at a "high setting," while FIGS. 67B and 68B illustrate the pressure threshold resistor 520 at a "low setting," The pressure threshold resistor 500 may be selectively adjusted between a high setting, as shown in FIG. 67A, and a low setting, as shown in FIG. 67B, by rotating the first section 522 of the housing 521 relative to the second section 523 of the housing 521. As shown in FIGS. 68A and 68B, rotation of the first section 522 of the housing 521 relative to the second section 523 of the housing 521 effectively decreases the compression of the spring 525, which in turn decreases the bias of the spring 525 acting on the valve 526. Consequently, the pressure threshold required to open the valve 526 also decreases. In this way, the pressure threshold is selectively adjustable by a user.

Flow Resistors

Turning to FIGS. 69A-E, a perspective and cross-sectional views of a flow resistor 550 are shown. As with the pressure threshold resistor 520, the flow resistor 550 may be shaped and size to be removably connectable to the inhalation port or the exhalation port of any number of respiratory devices, including, for example, the inhalation port 311 of the OPEP device 300. The flow resistor 550 may be removably connectable to respiratory devices by any suitable means, including a friction fit, threaded engagement, a snap fit, or the like.

Figure 69C:
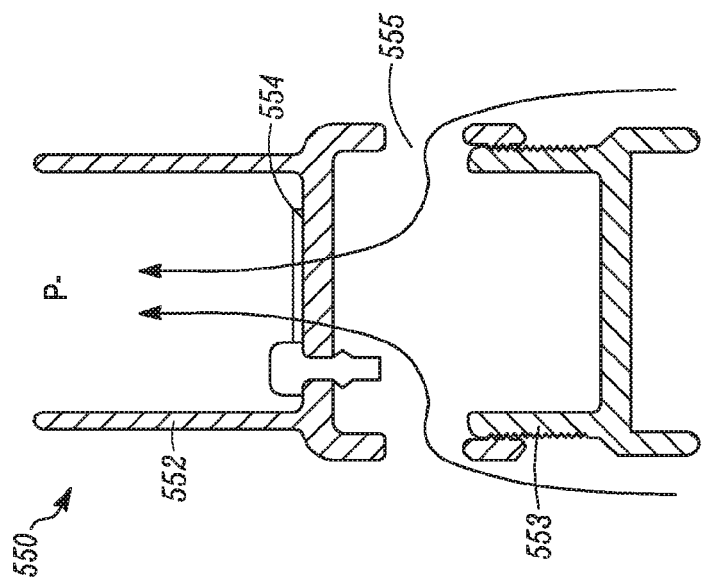
Figure 69B:
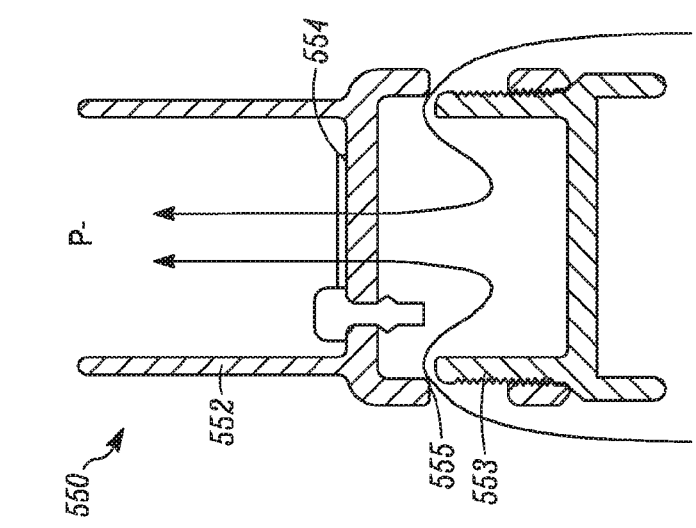
Figure 69A:
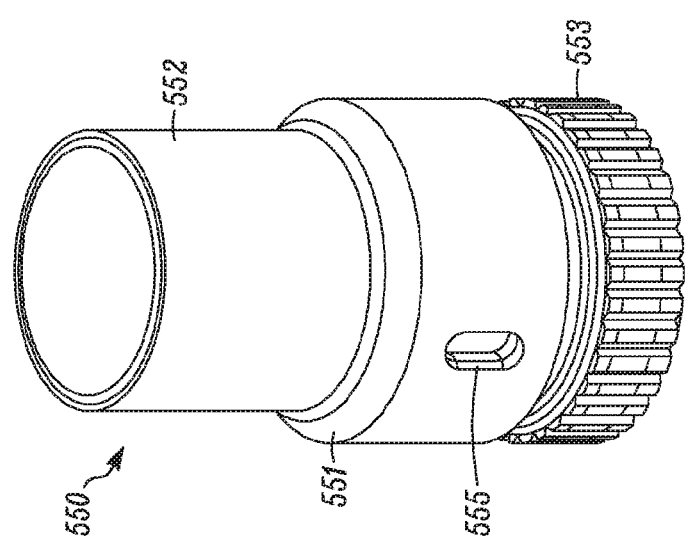

In general, the flow resistor 550 includes a housing 551 having a first section 552 and a second section 553, a one-way valve 554, and at least one orifice 555. The first section 552 of the housing 551 is connectable to the respiratory device. The one-way valve 554 is positioned in the first section 552 of the housing 551. If the flow resistor 550 is to be used during inhalation, as shown in FIGS. 69B-C, the one-way valve 554 may be positioned to open upon inhalation toward the first section 552 of the housing 551. If the flow resistor 550 is to be used during exhalation, as shown in FIGS. 69D-E, the one-way valve 554 may be positioned to open upon exhalation toward the second section 553 of the housing 551. One or more orifices 555 are formed in the first section 552 of the housing 551.

The first section 552 of the housing 551 is removably connected to the second section 553 of the housing 551 via a threaded engagement. The positon of the first section 552 relative to the second section 553 may be selectively increased or decreased by rotating the first section 552 relative to the second section 553. As discussed below, one section of the housing 551 may be rotated relative to the other section of the housing 551 to selectively increase or decrease the resistance to the flow of air through the flow resistor 550.

In operation the flow resistor 550 restricts the flow of air through the orifice(s) 555 of the flow resistor 550. As shown in FIG. 69B, during inhalation, a negative pressure is generated in the first section 552 of the housing 551, causing the one-way valve 554 to open toward the first section 552, and permitting air surrounding the flow resistor 550 and the attached respiratory device through the one or more orifices 555. Restriction of the flow of air through the flow restrictor 550, and therefore the attached respiratory device, results in a greater negative inhalation pressure within the attached respiratory device. As shown in FIG. 69C, the flow resistor 550 may be selectively adjusted to increase or decrease the restriction on the flow of air through the one or more orifices 550, and therefore the negative inhalation pressure in the attached respiratory device, by rotating the first section 552 of the housing 551 relative to the second section 553 of the housing 551, thereby causing the cross-sectional area of the orifice(s) 550 to gradually increase or decrease. In FIG. 69B, the flow resistor 550 is configured for low air flow and high inhalation pressure. In FIG. 69C, the flow resistor 550 is configured for high air flow and low inhalation pressure.

As shown in FIG. 69D, during exhalation, a positive pressure is generated in the first section 552 of the housing 551, causing the one-way valve 554 to open toward the second section 553, and permitting air in the attached respiratory device to flow through the flow resistor 550 and out the one or more orifices 555. Restriction of the flow of air through the flow restrictor 550, and therefore the attached respiratory device, results in a greater positive exhalation pressure within the attached respiratory device. As shown in FIG. 69E, the flow resistor 550 may be selectively adjusted to increase or decrease the restriction on the flow of air through the one or more orifices 555, and therefore the positive exhalation pressure in the attached respiratory device, by rotating the first section 552 of the housing 551 relative to the second section 553 of the housing 551, thereby causing the cross-sectional area of the orifice(s) 555 to gradually increase or decrease. In FIG. 69D, the flow resistor 550 is configured for low air flow and high exhalation pressure. In FIG. 69E, the flow resistor 550 is configured for high air flow and low exhalation pressure.

Figure 70A:
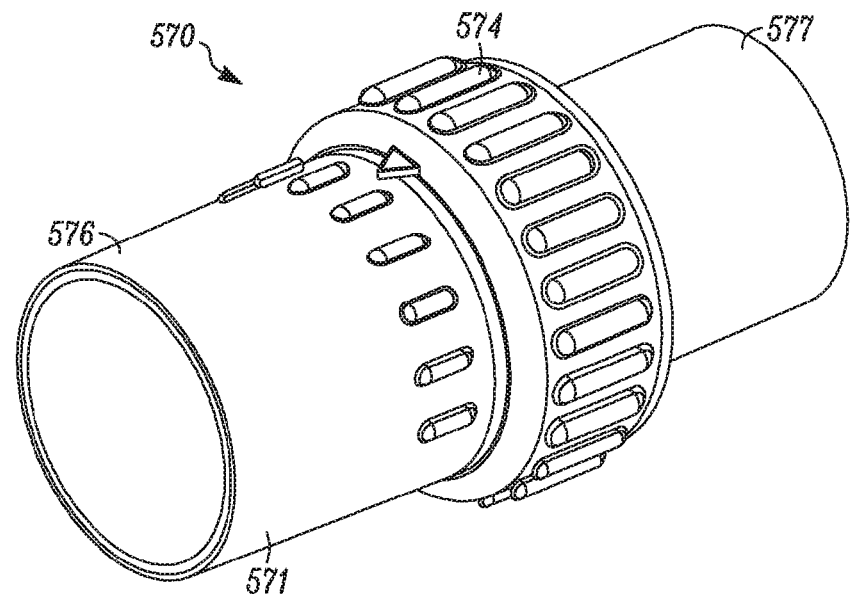
FIGS. 70A-C are perspective, cross-sectional, and front views of another flow resistor.
Figure 70B:
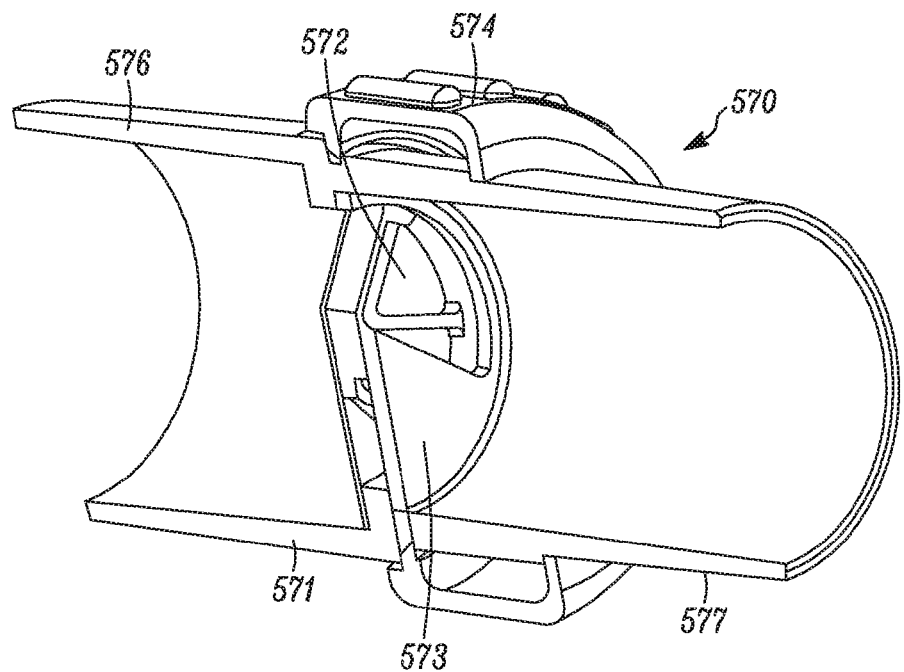
Figure 70C:
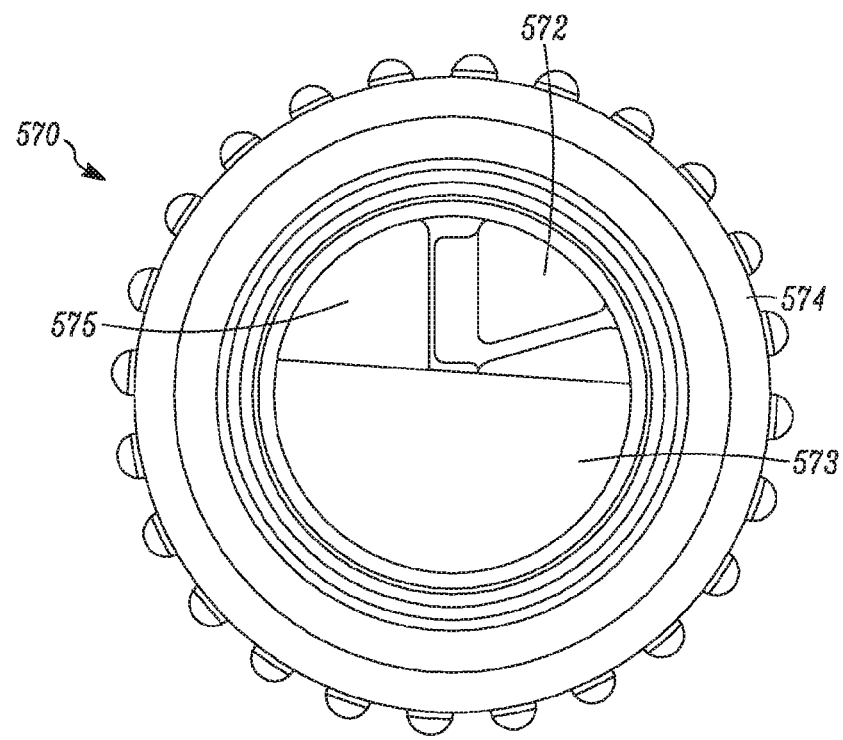

Turning to FIGS. 70A-C, perspective, cross-sectional, and front views of another embodiment of a flow resistor 570 are shown. In general, the flow resistor 570 includes a housing 571 having a first section 576 and a second section 577, a one-way valve 572, a restrictor plate 573, and an adjustment ring 574. The housing 571 is generally tubular. The one way valve 572, like the one-way valve 384, includes a flap configured to open in response to negative or positive pressure, depending on the direction of air flow. The one way valve 572 is different than the one-way valve 384 in that the flap is shaped and sized to cover only a portion of the internal cross-sectional area of the tubular housing 571. As shown, the flap may be shaped as a semi-circle. The restrictor plate 573 is positioned in the housing 571 adjacent the one-way valve 572 and is shaped and sized to cover only a portion of the internal cross-sectional area of the tubular housing 571. As shown, the restrictor plate 573 may also be shaped as a semi-circle. The restrictor plate 573 is connected to the adjustment ring 574, both of which may be selectively rotated relative to the housing 571. In this way, the adjustment ring 574 and the restrictor plate 573 may be rotated relative to the housing 571 to increase or decrease the cross sectional area of an orifice 575 formed in the tubular housing 571. In the embodiment shown in FIGS. 70B-C, because the one way valve 572 and the restrictor plate 573 are both shaped as semi-circles, the cross-sectional area of the orifice 575 may be selectively adjusted from a low setting, where the one-way valve 572 and the restrictor plate 573 are fully aligned, leaving a semi-circular orifice 575, to a high setting, where the one-way valve 572 and the restrictor plate 573 are opposite one another, completely covering the internal cross-sectional area of the tubular housing 571, and therefore altogether closing the orifice 575.

Like the flow resistor 550, the flow resistor 570 may be connected to an inhalation port or an exhalation port of a respiratory device, including for example, the inhalation port 311 of the OPEP device 300. The flow resistor 570 may be removably connectable to respiratory devices by any suitable means, including a friction fit, threaded engagement, a snap fit, or the like. The first section 576 of the housing 571 may be connected to an inhalation port of a respiratory device, whereas the second section 577 of the housing 571 may be connected to an exhalation port of a respiratory device. The flow resistor 570 otherwise operates in the same manner as described above with regard to the flow resistor 550.

Figure 71:
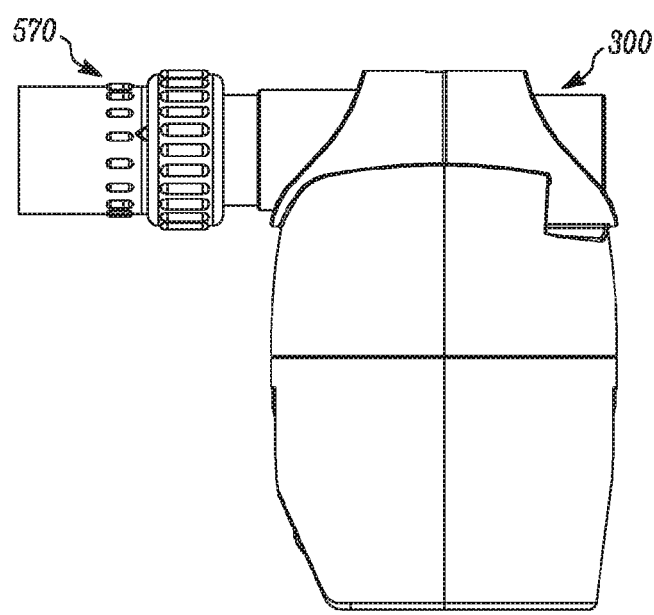
FIG. 71 is a side view of the flow resistor of FIGS. 70A-C connected to the OPEP device of FIG. 35.
Figure 73A:
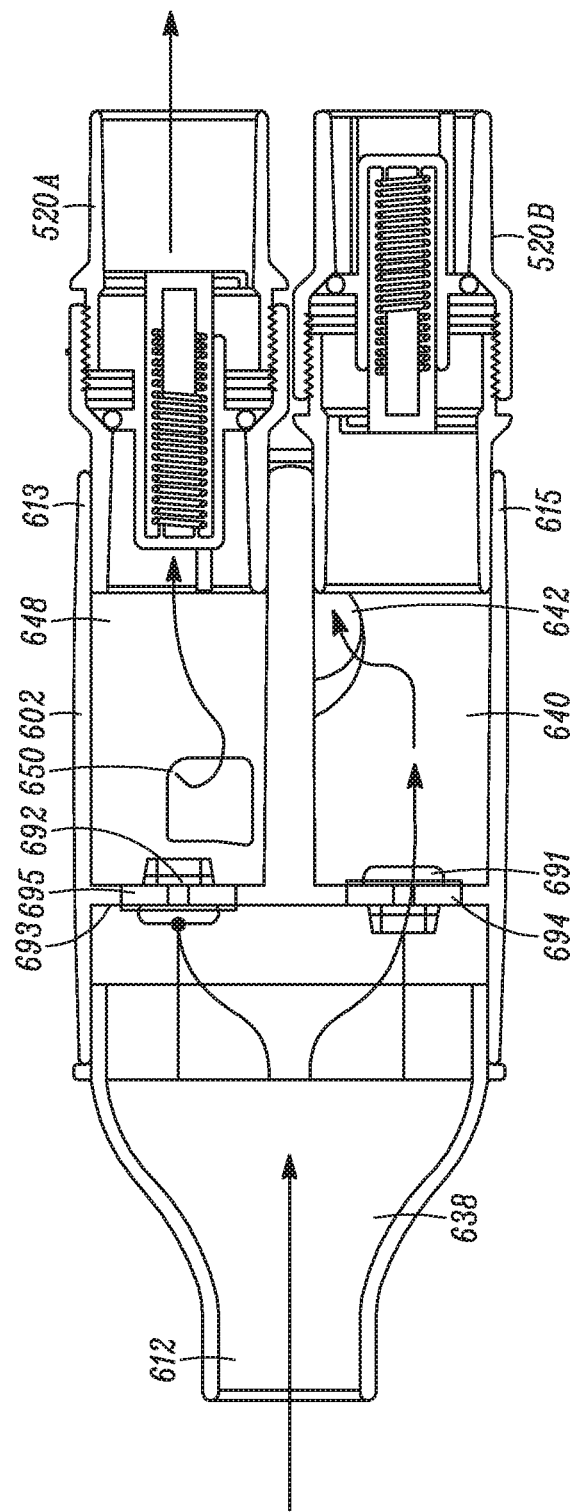
FIGS. 73A-F are full and partial cross-sectional views of the combined RMT and OPEP device of FIGS. 72A-C, illustrating administration of RMT and OPEP therapy upon exhalation; and, FIGS. 74A-E are full and partial cross-sectional views of the combined RMT and OPEP device of FIGS. 72A-C, illustrating administration of RMT and OPEP therapy upon inhalation.
Figure 73B:
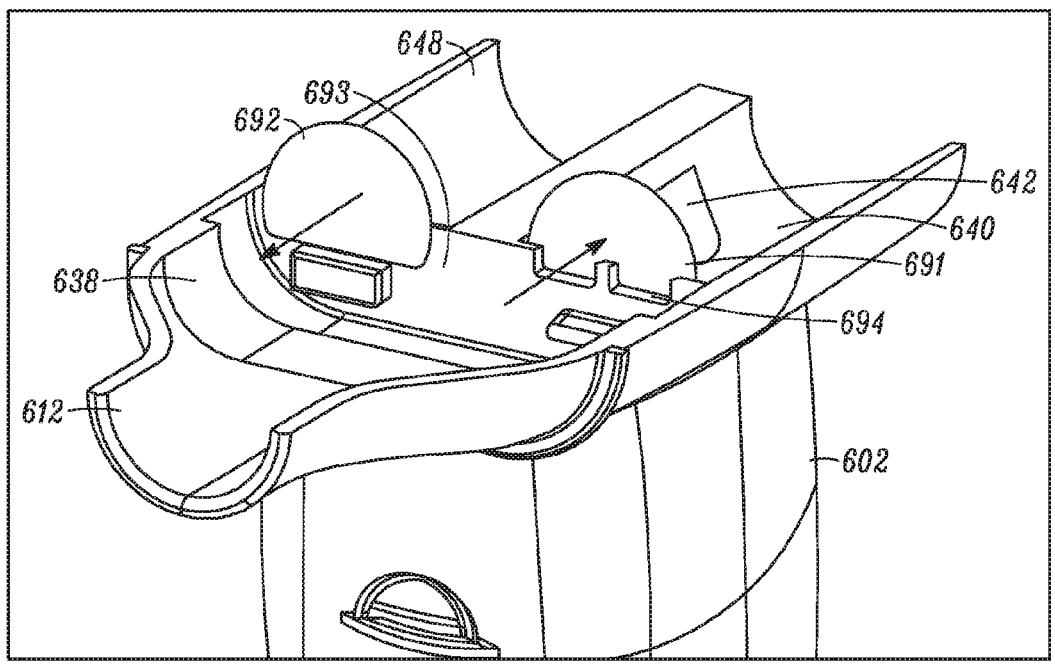
Figure 73C:
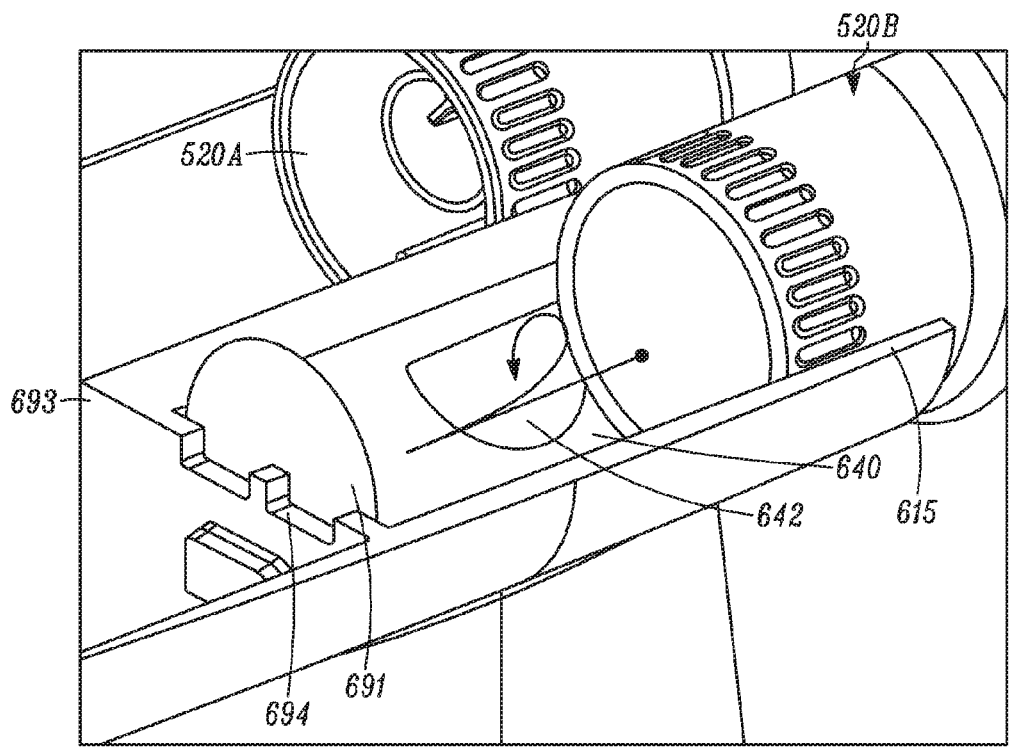
Figure 73D:
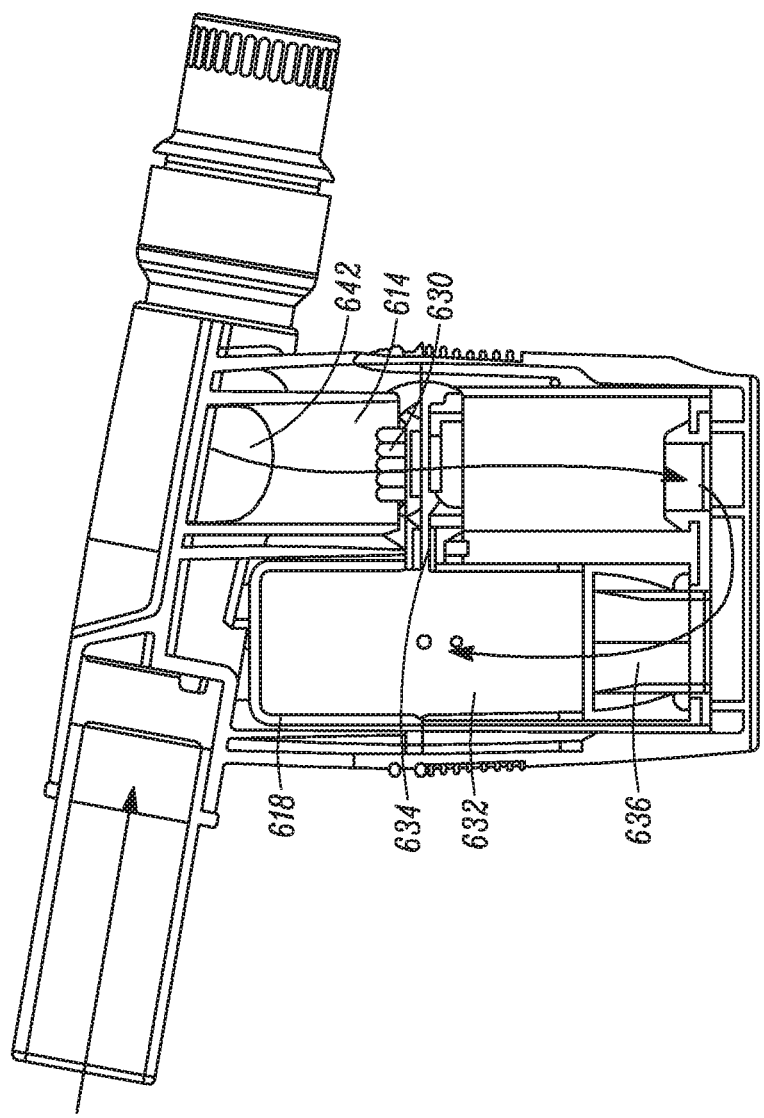
Figure 73E:
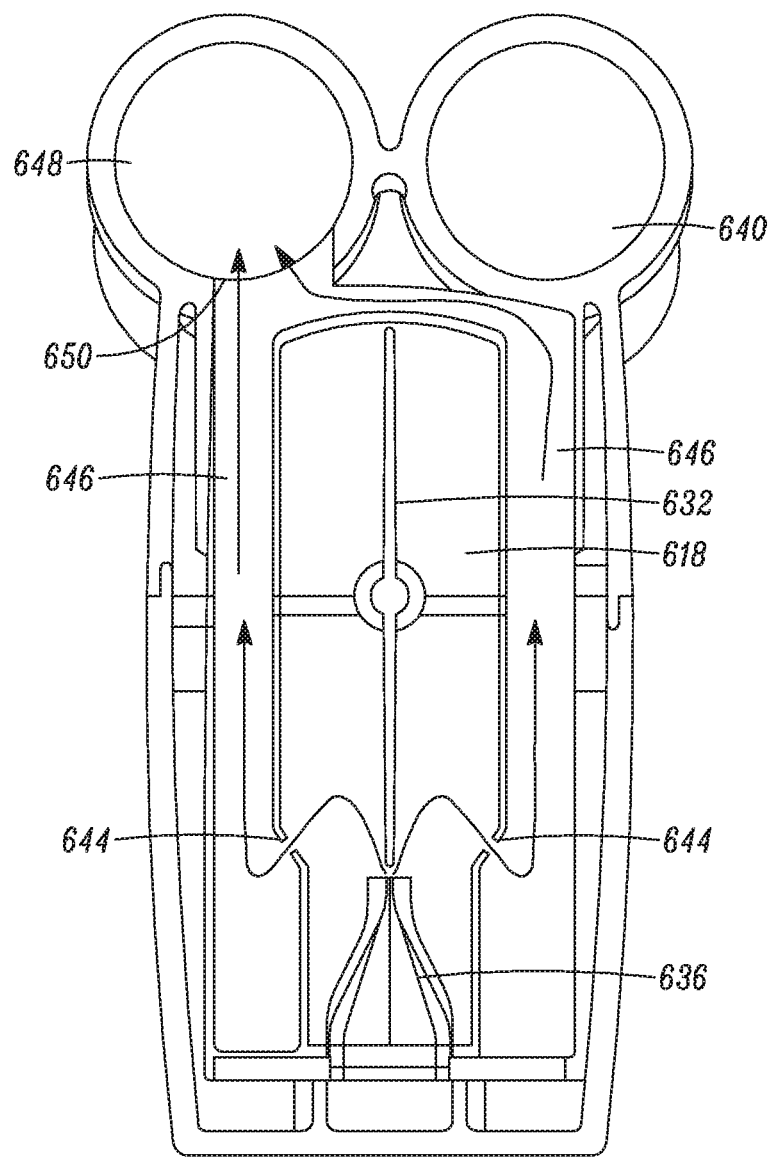
Figure 73F:
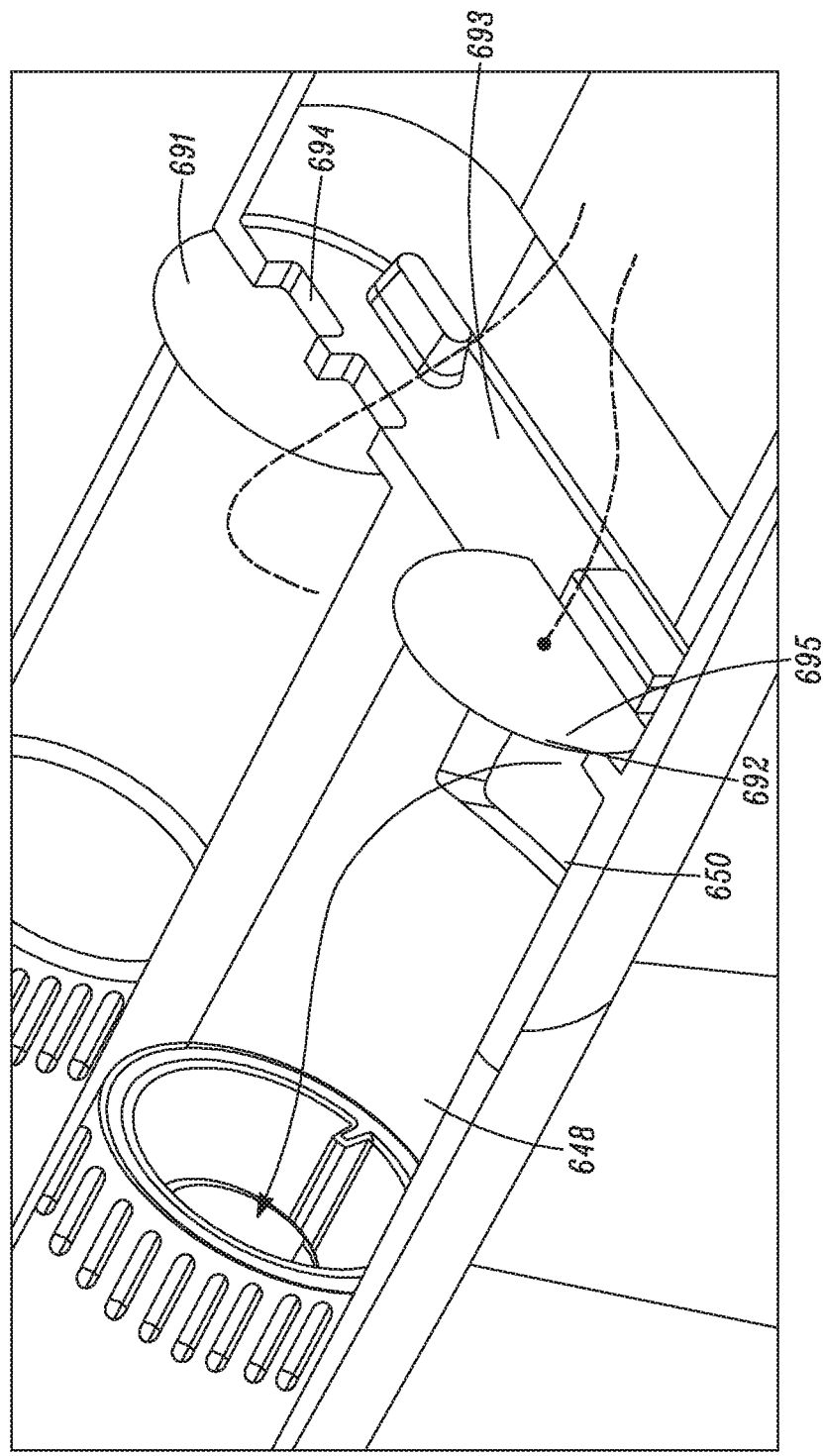
Figure 74A:
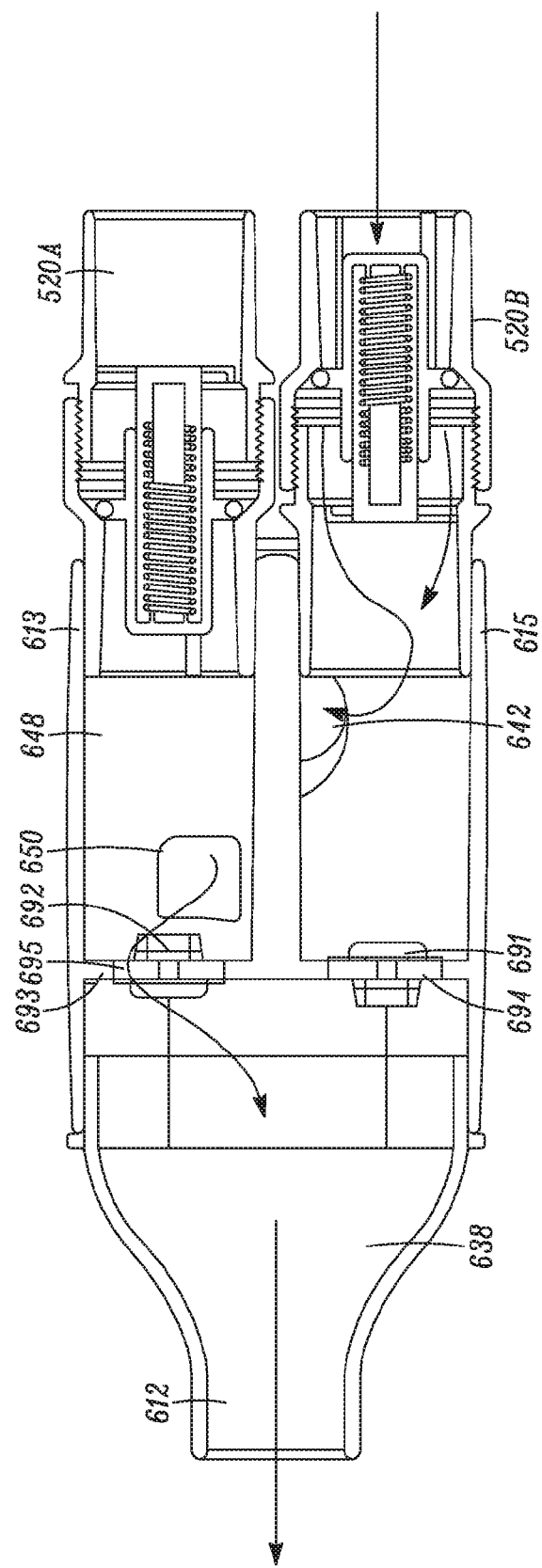
Figure 74B:
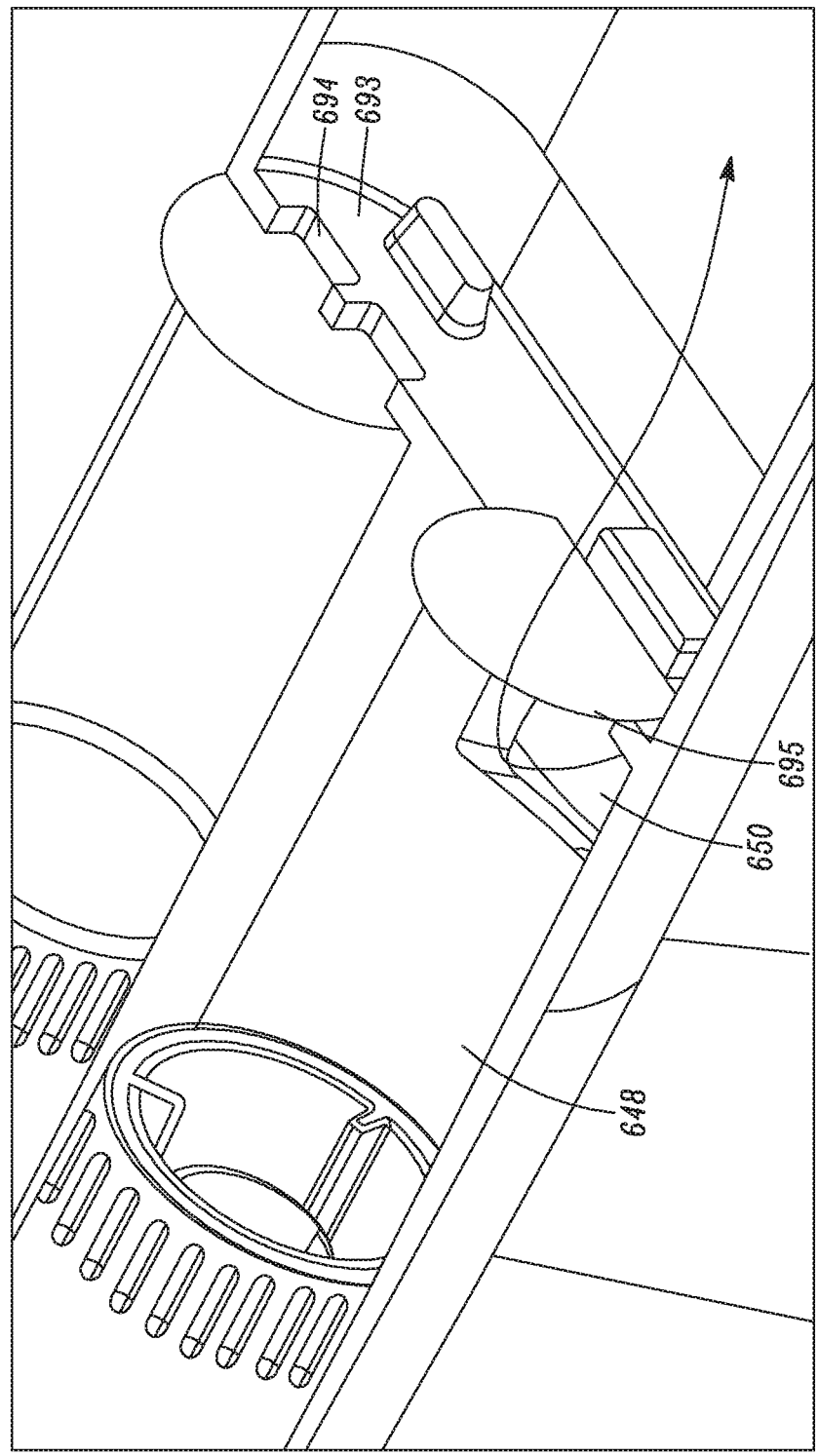
Figure 74C:
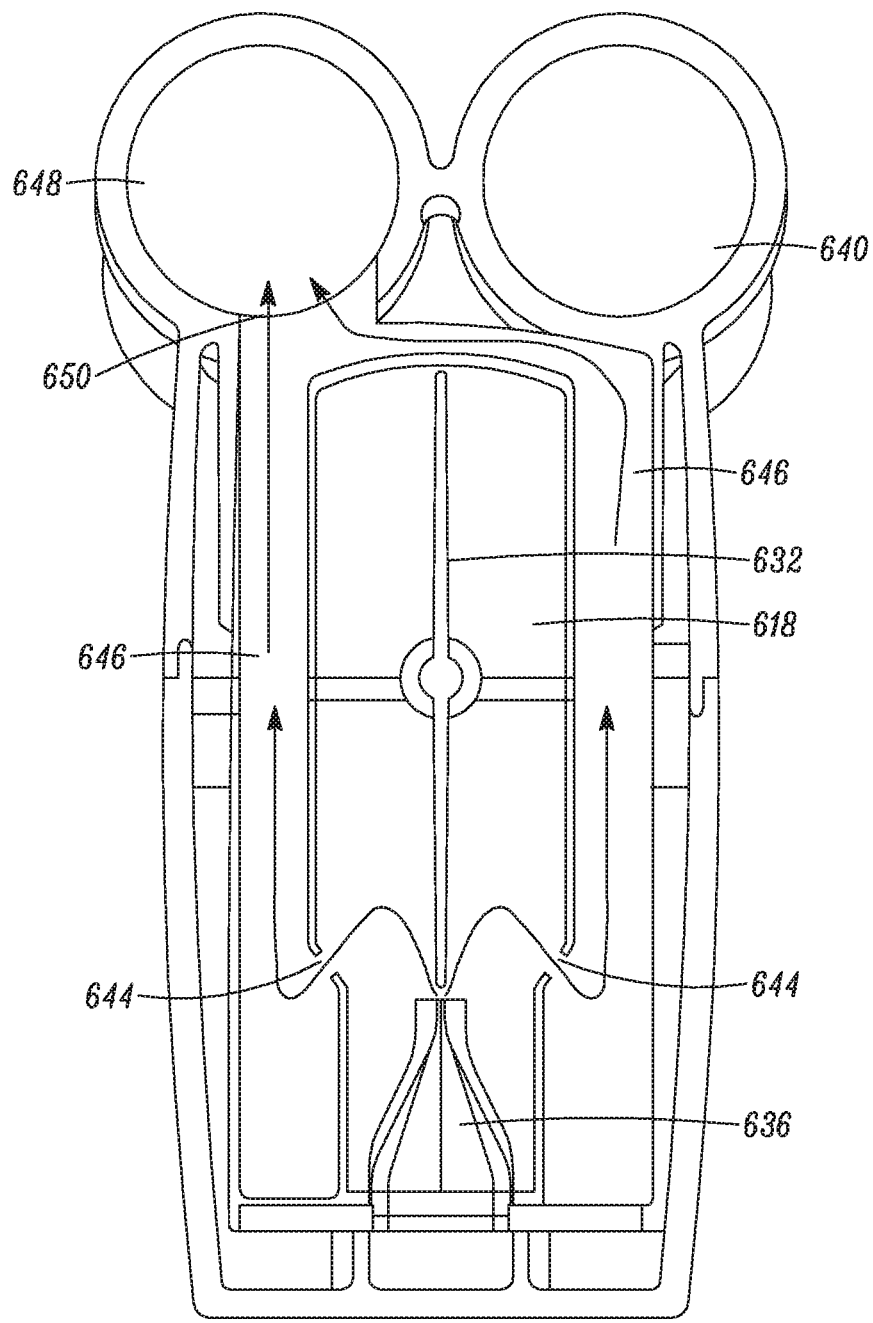
Figure 74D:
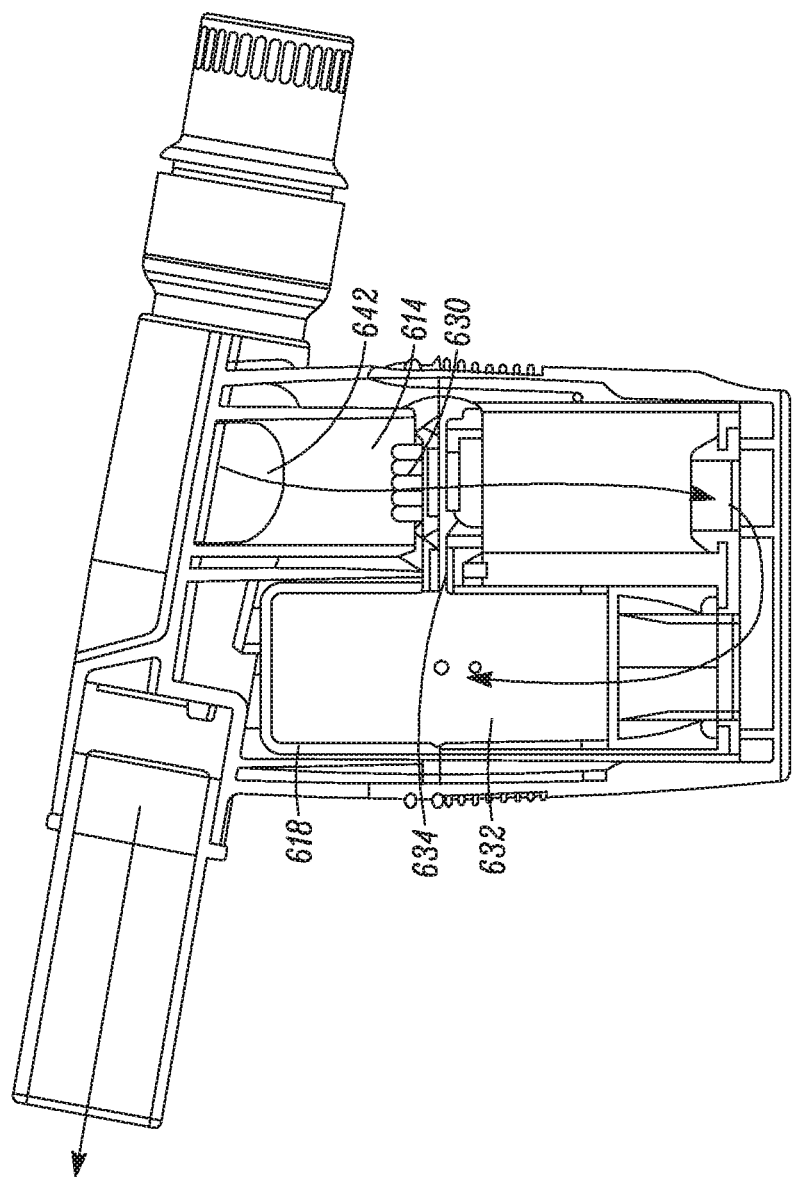
Figure 74E:
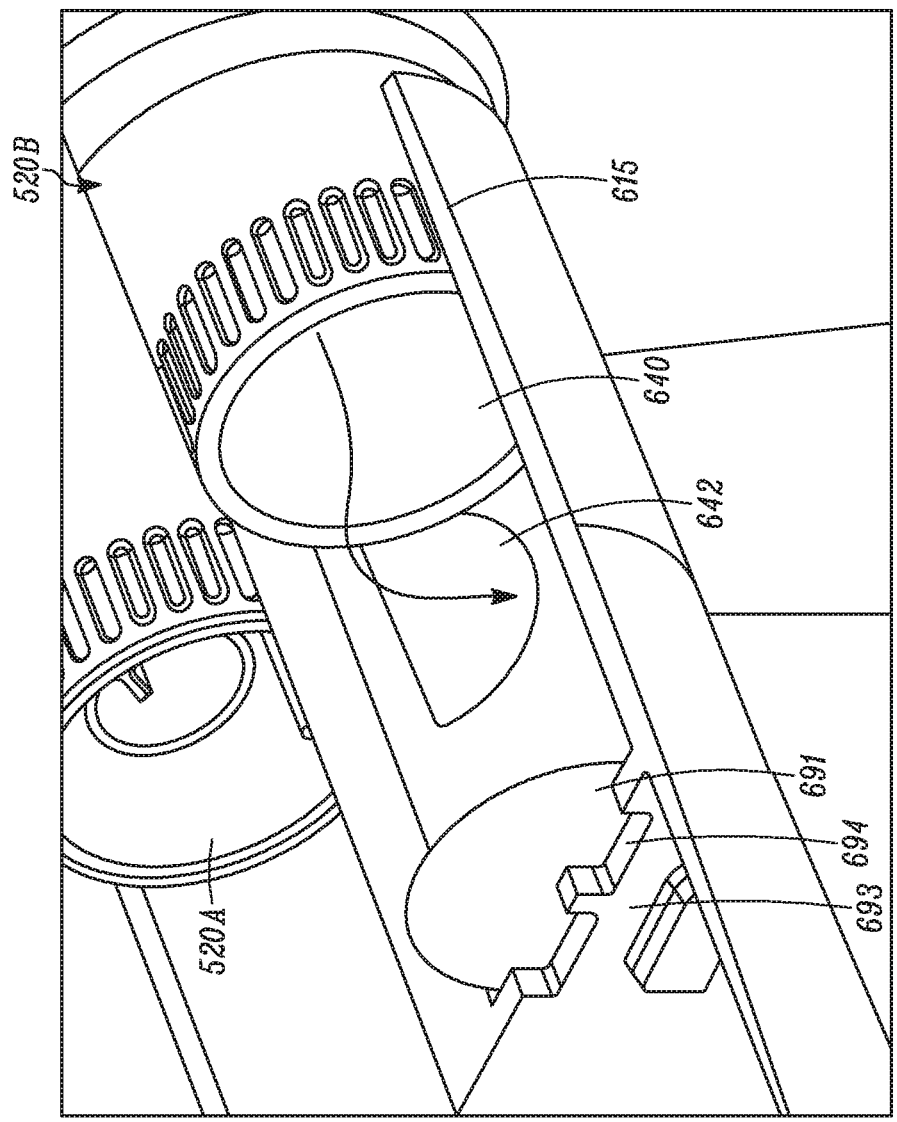

The flow resistor 570 differs from the flow resistor 550, however, in that it may also be attached to the mouthpiece or inlet of a respiratory treatment device, including for example, the OPEP device 300, as shown in FIG. 71. Because the flow resistor 550 may be selectively adjusted to maintain an orifice 575 unobstructed by the one-way valve 572 or the restrictor plate 573, the flow resistor 550 may be used at the mouthpiece or inlet of a respiratory treatment device to perform RMT upon both inhalation or exhalation. If, however, the flow resistor 550 is selectively adjusted such that the one-way valve 572 and the restrictor plate 573 are opposite one another, completely covering the cross-sectional area of the tubular housing 571, thereby eliminating the orifice 575, exhalation may be entirely prevented, thus preventing use of the attached respiratory device.

Combined RMT and OPEP Embodiment

Turning to FIGS. 72A-C, 73A-F, and 74A-E, a combined RMT and OPEP device 600 is shown. FIGS. 72A-C are perspective, front, and side views of the device 600. FIGS.

73A-F are full and partial cross-sectional views of the device 600, illustrating combined administration of RMT and OPEP therapy during exhalation. FIGS. 74A-E are full and partial cross-sectional views of the device 600, illustrating combined administration of RMT and OPEP therapy during inhalation.

The device 600 is similar to the OPEP device 400 in that the device 600 is configured to administer OPEP therapy upon both exhalation and inhalation. While the shape and configuration of the device 600 differs from that of the OPEP device 400, the general components for performing OPEP therapy are otherwise the same. The device 600, however, substitutes the one-way exhalation valve 490 in in the OPEP device 400 with a pressure threshold resistor 520A configured to provide RMT upon exhalation, and substitutes the one-way inhalation valve 484 with a pressure threshold resistor 520B configured to provide RMT upon inhalation. Alternatively, the pressure threshold resistors 520A and 520B may be replaced with flow resistors, such as for example, the flow resistor 550.

Like the OPEP device 400, the device 600 includes a housing 602 including a first opening 612 (a mouthpiece), a second opening 613 (an exhalation port), and a third opening 615 (an inhalation port). Although the first opening 612 is shown as a mouthpiece, the first opening 612 may alternatively be associated with other user interfaces, for example, a gas mask or a breathing tube. As stated above, a pressure threshold resistor 520A is connected to the device 600 at the second opening 613 (an exhalation port) to provide RMT upon exhalation at the first opening 612, while a pressure threshold resistor 520B is connected to the device 600 at the third opening 615 (an inhalation port) to provide RMT upon inhalation at the first opening 612.

The device 600 further includes a manifold plate 693 having an exhalation passage 694 and an inhalation passage 695. A one-way valve 691 is adapted to mount within the manifold plated 693 adjacent to the exhalation passage 694 such that the one-way valve opens in response to air exhaled into the first opening 612, and closes in response to air inhaled through the first opening 612. A separate one-way valve 692 is adapted to mount within the manifold plate 693 adjacent to the inhalation passage 695 such that the one-way valve 692 closes in response to air exhaled into the first opening 612, and opens in response to air inhaled through the first opening 612. Although the one-way valve 691 and one-way valve 692 are shown as separate components, it should be appreciated that they could be designed as a single part with two flaps adapted to fit within the manifold plate 693.

The device 600 further includes a restrictor member 630 and a vane 632 operatively connected by a shaft 634, the assembly of which may operate in the same manner as described above with regard to the previously disclosed OPEP devices, as well as a variable nozzle 636. The device also includes a plurality of chambers. Air transmitted through the first opening 612 of the housing 602, whether inhaled or exhaled, traverses a flow path that passes, at least in part, past the restrictor member 630 housed in a first chamber 614, and through a second chamber 618 which houses the vane 632 operatively connected to the restrictor member 630. In this regard, at least a portion of the flow path for both air exhaled into or inhaled from the first opening 612 is overlapping, and occurs in the same direction.

Turning to FIGS. 73A-F, operation of the device 600 will now be described during a period of exhalation. As a user exhales into the first opening 612, exhaled air enters a diverter chamber 638. In the diverter chamber 638, a positive exhalation pressure generated by the exhaled air maintains the one-way valve 692 in a closed position, while forcing the one-way valve 691 open, allowing exhaled air to enter a third chamber 640. The third chamber 640 is in fluid communication with the third opening 615 (an inhalation port), and via an opening 642, the first chamber 614. In the third chamber 640, exhaled air is forced to flow through the opening 642 into the first chamber 614, since the pressure threshold resistor 520B is inserted in the third opening 615 and configured to provide RMT on inhalation. As the exhaled air flows through the first chamber 614, past the restrictor member 630, through the variable nozzle 636, and past the vane 632 in the second chamber 618, rotation of the vane 632 causes rotation of the restrictor member 630 for administration of OPEP therapy, as described above with regard to the previously described OPEP devices.

Exhaled air then exits the second chamber 618 through a pair of openings 644 and flows into a forth chamber 646, which is also in fluid communication with a fifth chamber 648 via an opening 650. The fifth chamber itself is in fluid communication with the one-way valve 629 and the pressure threshold resistor 520A connected to the device 600 via the second opening 613 (an exhalation port). At this point, the positive exhalation pressure in the diverter chamber 638 is greater than the positive exhalation pressure in the fifth chamber 648, keeping the one-way valve 692 closed, and preventing exhaled air from re-entering the diverter chamber 638. As such, the exhaled air in the fifth chamber 648 is forced to exit the device 600 through the second opening 613 and the pressure threshold resistor 520A for the administration of RMT.

Turning to FIGS. 74A-F, operation of the device 600 will now be described during a period of inhalation. As a user inhales through the device 600 through the first opening 612, a negative inhalation pressure is generated in the diverter chamber 638, maintaining the one-way valve 691 in a closed position, while pulling the one-way valve 692 open. As a user continues to inhale with the one-way valve 692 open, a negative inhalation pressure is generated in the fifth chamber 648. The fifth chamber is in fluid communication with the pressure threshold resistor 520A connected to the device 600 via the second opening 613 (exhalation port) and the forth chamber 646 via opening 650. Since the pressure threshold resistor 520A is configured for administration of RMT on exhalation, the negative inhalation pressure is transmitted to the forth chamber 646 via the opening 650, and consequently, the second chamber 618. The negative inhalation pressure in the second chamber 618 draws open the variable nozzle 636, thereby transmitting the negative pressure to the first chamber 614, past the restrictor member 630, and into the third chamber 640 via the opening 642. The third chamber 640 is in fluid communication with the one-way valve 691 and the pressure threshold resistor 520B. At this point, the negative exhalation pressure in the diverter chamber 638 is greater than the negative exhalation pressure in the third chamber 640, keeping the one-way valve 691 closed, and preventing inhaled air from re-entering the diverter chamber 638. As such, the negative inhalation pressure in third chamber 640 is forced to draw air into the device 600 through the third opening 615 and the pressure threshold resistor 520B for the administration of RMT.

As a user continues to inhale and the pressure threshold is reached, air flows through the pressure threshold resistor 520B and into the device 600, along the follow inhalation flow path: inhaled air first flows into the third chamber 640, then through the opening 642 into the first chamber 614, past the restrictor member 630, through the variable nozzle 636 into the second chamber 618, past the vane 632, into the forth chamber 646, through the opening 650 into the fifth chamber 648, through the inhalation passage 695 into the diverter chamber 638, then out the first opening 612. As inhaled air flows through the first chamber 614, past the restrictor member 630, through the variable nozzle 636, and through the second chamber 618, past the vane 632, rotation of the vane 632 causes rotation of the restrictor member 630 for administration of OPEP therapy, as described above with regard to the previously described OPEP devices. In this way, the device 600 provides RMT and OPEP therapy during both inhalation and exhalation.

The foregoing description has been presented for purposes of illustration and description, and is not intended to be exhaustive or to limit the inventions to the precise forms disclosed. It will be apparent to those skilled in the art that the present inventions are susceptible of many variations and modifications coming within the scope of the following claims.

What is claimed is:

1. A respiratory treatment device comprising:
   a housing enclosing a plurality of chambers;
   a first opening in the housing configured to transmit air exhaled into and air inhaled from the housing;
   a second opening in the housing configured to permit air exhaled into the first opening to exit the housing;
   a third opening in the housing configured to permit air outside the housing to enter the housing upon inhalation at the first opening;
   an exhalation flow path defined between the first opening and the second opening, and an inhalation flow path defined between the third opening and the first opening; and,
   a restrictor member positioned along the exhalation flow path and the inhalation flow path, the restrictor member movable between a closed position, where a flow of air along the exhalation flow path or the inhalation flow path is restricted, and an open position, where the flow of exhaled air along the exhalation flow path or the inhalation flow path is less restricted;
   wherein the second opening comprises a one-way exhalation valve configured to permit air exhaled into the housing to exit the housing upon exhalation at the first opening; and,
   wherein a cross-sectional area of the second opening is selectively adjustable to control a resistance to the flow of air therethrough.

2. The respiratory treatment device of claim 1, wherein the one-way exhalation valve is configured to open in response to a positive threshold pressure.

3. The respiratory treatment device of claim 2, wherein the threshold pressure is selectively adjustable.

4. The respiratory treatment device of claim 1, wherein the one-way exhalation valve comprises a spring configured to bias the one-way valve toward a closed position.

5. The respiratory treatment device of claim 4, wherein a level of bias is selectively adjustable.

6. The respiratory treatment device of claim 1, further comprising a vane in fluid communication with the exhalation flow path and the inhalation flow path, the vane operatively connected to the restrictor member and configured to reciprocate between a first position and a second position in response to a flow of exhaled air along the exhalation flow path or the inhalation flow path.

7. The respiratory treatment device of claim 1, wherein the second opening is associated with a dial rotatable to selectively adjust the cross-sectional area of the second opening.

8. A respiratory treatment device comprising:
   a housing enclosing a plurality of chambers;
   a first opening in the housing configured to transmit air exhaled into and air inhaled from the housing;
   a second opening in the housing configured to permit air exhaled into the first opening to exit the housing;
   a third opening in the housing configured to permit air outside the housing to enter the housing upon inhalation at the first opening;
   an exhalation flow path defined between the first opening and the second opening, and an inhalation flow path defined between the third opening and the first opening; and,
   a restrictor member positioned along the exhalation flow path and the inhalation flow path, the restrictor member movable in response to a flow of air along the exhalation flow path, during a single period of exhalation, or the inhalation flow path, during a single period of inhalation, repeatedly between a closed position, where the flow of air along the exhalation flow path or the inhalation flow path is restricted, and an open position, where the flow of exhaled air along the exhalation flow path or the inhalation flow path is less restricted;
   wherein the third opening comprises a one-way inhalation valve configured to permit air outside the housing to enter the housing upon inhalation at the first opening; and,
   wherein a cross-sectional area of the third opening is selectively adjustable to control a resistance to the flow of air therethrough.

9. The respiratory treatment device of claim 8, wherein the one-way inhalation valve is configured to open in response to a negative threshold pressure.

10. The respiratory treatment device of claim 9, wherein the threshold pressure is selectively adjustable.

11. The respiratory treatment device of claim 8, wherein the one-way inhalation valve comprises a spring configured to bias the one-way valve toward a closed position.

12. The respiratory treatment device of claim 11, wherein a level of bias is selectively adjustable.

13. The respiratory treatment device of claim 8, further comprising a vane in fluid communication with the exhalation flow path and the inhalation flow path, the vane operatively connected to the restrictor member and configured to reciprocate between a first position and a second position in response to the flow of exhaled air along the exhalation flow path or the inhalation flow path.

14. The respiratory treatment device of claim 8, wherein the third opening is associated with a dial rotatable to selectively adjust the cross-sectional area of the third opening.

15. A respiratory treatment device comprising:
   a housing enclosing a plurality of chambers;
   a first opening in the housing configured to transmit air exhaled into and air inhaled from the housing;
   a second opening in the housing configured to permit air exhaled into the first opening to exit the housing;
   a third opening in the housing configured to permit air outside the housing to enter the housing upon inhalation at the first opening;

an exhalation flow path defined between the first opening and the second opening, and an inhalation flow path defined between the third opening and the first opening; and, a restrictor member positioned along the exhalation flow path, the restrictor member movable in response to a flow of air along the exhalation flow path, during a single period of exhalation, or the inhalation flow path, during a single period of inhalation, repeatedly between a closed position, where the flow of air along the exhalation flow path is restricted, and an open position, where the flow of exhaled air along the exhalation flow path is less restricted;

wherein the third opening comprises a one-way inhalation valve configured to permit air outside the housing to enter the housing upon inhalation at the first opening; and, wherein a cross-sectional area of the third opening is selectively adjustable to control a resistance to the flow of air therethrough.

16. The respiratory treatment device of claim 15, wherein the one-way inhalation valve is configured to open in response to a negative threshold pressure.

17. The respiratory treatment device of claim 16, wherein the threshold pressure is selectively adjustable.

18. The respiratory treatment device of claim 15, wherein the one-way inhalation valve comprises a spring configured to bias the one-way valve toward a closed position.

19. The respiratory treatment device of claim 18, wherein a level of bias is selectively adjustable.

20. The respiratory treatment device of claim 15, further comprising a vane in fluid communication with the exhalation flow path, the vane operatively connected to the restrictor member and configured to reciprocate between a first position and a second position in response to the flow of exhaled air along the exhalation flow path.

21. The respiratory treatment device of claim 15, wherein the third opening is associated with a dial rotatable to selectively adjust the cross-sectional area of the third opening.

* * * * *

UNITED STATES PATENT AND TRADEMARK OFFICE
CERTIFICATE OF CORRECTION

PATENT NO. : 10,449,324 B2
APPLICATION NO. : 15/223564
DATED : October 22, 2019
INVENTOR(S) : Adam Meyer et al.

Page 1 of 1

It is certified that error appears in the above-identified patent and that said Letters Patent is hereby corrected as shown below:

In the Claims

In Column 35, Claim 15, Lines 8-9, delete "or the inhalation flow path, during a single period of inhalation,"

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*